(12) United States Patent
Becker et al.

(10) Patent No.: US 9,289,427 B2
(45) Date of Patent: *Mar. 22, 2016

(54) POLYMORPHIC FORMS OF 3-(1-{3-[5-(1-METHYL-PIPERIDIN-4-YLMETHOXY)-PYRIMIDIN-2-YL]-BENZYL}-6-OXO-1,6-DIHYDRO-PYRIDAZIN-3-HYDROCHLORIDE SALT AND PROCESSES OF MANUFACTURING THEREOF

(71) Applicant: Merck Patent GmbH, Darmstadt (DE)

(72) Inventors: Axel Becker, Darmstadt (DE); Clemens Kuehn, Darmstadt (DE); Christoph Saal, Otzberg (DE); Oliver Schadt, Rodenbach (DE); Dieter Dorsch, Ober-Ramstadt (DE); Heinz-Hermann Bokel, Darmstadt (DE); Frank Stieber, Heidelberg (DE); Cristina Donini, Geneva (IT)

(73) Assignee: MERCK PATENT GMBH, Darmstadt (DE)

( * ) Notice: Subject to any disclaimer, the term of this patent is extended or adjusted under 35 U.S.C. 154(b) by 20 days.

This patent is subject to a terminal disclaimer.

(21) Appl. No.: 14/158,182

(22) Filed: Jan. 17, 2014

(65) Prior Publication Data
US 2014/0200221 A1    Jul. 17, 2014

Related U.S. Application Data

(62) Division of application No. 13/143,831, filed as application No. PCT/EP2009/008684 on Dec. 4, 2009, now Pat. No. 8,710,058.

(30) Foreign Application Priority Data

Jan. 8, 2009    (EP) .................... 09000140

(51) Int. Cl.
| | |
|---|---|
| A61K 31/506 | (2006.01) |
| C07D 403/10 | (2006.01) |
| C07D 401/14 | (2006.01) |
| A61K 31/517 | (2006.01) |
| A61K 45/06 | (2006.01) |

(52) U.S. Cl.
CPC ............. *A61K 31/506* (2013.01); *A61K 31/517* (2013.01); *A61K 45/06* (2013.01); *C07D 401/14* (2013.01); *C07D 403/10* (2013.01)

(58) Field of Classification Search
CPC .......................... C07D 403/10; A61K 31/506
USPC ..................... 544/238; 514/252.02
See application file for complete search history.

(56) References Cited

U.S. PATENT DOCUMENTS

| | | | |
|---|---|---|---|
| 7,094,909 B2 | 8/2006 | Kucera et al. | |
| 7,169,932 B2 | 1/2007 | Kucera et al. | |
| 7,232,910 B2 | 6/2007 | Ewanicki et al. | |
| 7,381,737 B2 | 6/2008 | DelMonte et al. | |
| 7,691,871 B2 | 4/2010 | Camponovo et al. | |
| 7,812,032 B2 | 10/2010 | Viswanath et al. | |
| 7,820,812 B2 | 10/2010 | Viswanath et al. | |
| 8,030,326 B2 | 10/2011 | Viswanath et al. | |
| 8,034,926 B2 | 10/2011 | Viswanath et al. | |
| 8,710,058 B2 * | 4/2014 | Becker ................ | C07D 401/14 514/252.02 |
| 2007/0203196 A1 | 8/2007 | Ewanicki et al. | |
| 2007/0249637 A1 | 10/2007 | Collins et al. | |
| 2008/0039459 A1 | 2/2008 | Folkes et al. | |
| 2008/0085880 A1 | 4/2008 | Viswanath et al. | |
| 2008/0091008 A1 | 4/2008 | Viswanath et al. | |
| 2008/0293719 A1 | 11/2008 | Dorsch et al. | |

FOREIGN PATENT DOCUMENTS

| | | |
|---|---|---|
| WO | 2009006959 | 1/2009 |
| WO | 2009007074 | 1/2009 |

OTHER PUBLICATIONS

Simone, Oncology: Introduction, Cecil Textbook of Medicine, 20th Edition, vol. 1, pp. 1004-1101 O, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Porter, Small molecule c-Met kinase inhibitors: a review of recent patents, Expert Opin. Ther. Patents 20(2): 159-177 (2010).*
Ciardiello et al., Clinical Cancer Research, 6:2053-2063, May 2000.
Luke et al., Clinical Cancer Research, 18(9):2638-2647, Feb. 2012.
Andersson et al. Cancer Cell International, 8(1), 6 pages, 2008.

(Continued)

*Primary Examiner* — Deepak Rao
(74) *Attorney, Agent, or Firm* — Millen, White, Zelano, Branigan, P.C.

(57) ABSTRACT

The present invention relates to 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride solvates and crystalline modifications thereof. The present invention further relates to processes of manufacturing these crystalline modifications as well as their use in the treatment and/or prophylaxis of physiological and/or pathophysiological conditions, which are caused, mediated and/or propagated by the inhibition, regulation and/or modulation of signal transduction of kinases, in particular by the inhibition of tyrosine kinases, e.g. pathophysiological conditions such as cancer.

22 Claims, 38 Drawing Sheets

(56) References Cited

OTHER PUBLICATIONS

Viglietto et al. Nature Medicine, 8(10): 1136-1144, Oct. 2002.
Grant & Hackh'S Chemical Dictionary Fifth Edition, McGraw-Hill Book Company; Copyright ©1987 by McGraw-Hill, Inc. ISBN: 0-07-024067-1; p. 289. (3 pages).
Buchanan, Sean G. et al., Mol. Cancer Ther. 2009; 8(12), Dec. 2009, pp. 3181-3190.
Guessous, Fadila et al., Anti-Cancer Agents in Medicinal Chemistry, 2010, 10, 28-35.
Jin, Honhkui et al., Cancer res. 2008; 68: (11), Jun. 1, 2008, pp. 4360-4368.
Knowles, Lynn M. et al., Clin. Cancer res. 2009; 15(11) Jun. 1, 2009, pp. 3740-3750.
Liu, Xiangdong et al., Clinical Cancer Res., published Sep. 14, 2011, pp. 1-37.
Qian, F. et al., Cancer Res. 2009; 69: (20), Oct. 15, 2009, pp. 8009-8016.
Sampson, Erik R. et al., Journal of Bone and Mineral Research, vol. 26, No. 6, Jun. 2011, pp. 1283-1294.
Zillhardt, Marion et al., Clin. Cancer Res.; 17812) Jun. 15, 2011, pp. 4042-4051.
Zou, Helen Y. et al., Mol Cancer Therapeutics, published online Mar. 2, 2012.
Zou, Helen Y. et al., Cancer Res. 2007; 67(9) May 1, 2007, pp. 4408-4417.
International Search Report of PCT/EP2009/008684 (Feb. 3, 2010).
Maruzen Co., Ltd.,"Handbook for Preparation of Crystals of Organic Compound: Principle and Know-how", Jul. 25, 2008, pp. 74-79.
English translation of the Japanese Office Action issued Aug. 18, 2015 in JP 2014-231814.

* cited by examiner

POLYMORPHIC FORMS OF 3-(1-{3-[5-(1-METHYL-PIPERIDIN-4-YLMETHOXY)-PYRIMIDIN-2-YL]-BENZYL}-6-OXO-1,6-DIHYDRO-PYRIDAZIN-3-HYDROCHLORIDE SALT AND PROCESSES OF MANUFACTURING THEREOF

TECHNICAL FIELD

The present invention relates to 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride, its solvates and crystalline modifications thereof as well as their medical uses and processes of manufacturing.

PRIOR ART 3-(1-{3-[5-(1-methyl-pipendin-4-ylmethoxy)-pyrimidin-2-yl]-benzyl}-6-oxo-1,6-dihydro-pyridazin-3-yl)-benzonitrile (I)

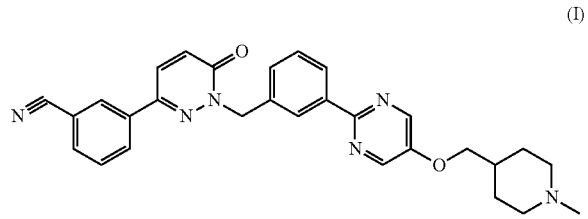 [SMILES: CN1CCC(COc2cnc(-c3cccc(Cn4nc(-c5cccc(C#N)c5)ccc4=O)c3)nc2)CC1]

(I)

was first described in international patent applications PCT/EP20081003473, filed on 29 Apr. 2008, and PCT/EP2008/005508, filed on 4 Jul. 2008.

In PCT/EP2008/003473 3-(1-{3-[5-(1-methyl-piperidin-4-ylmethoxy)-pyrimidin-2-yl]-benzyl}-6-oxo-1,6-dihydro-pyridazin-3-yl)-benzonitrile is referred to as compound "A257". Example 40 of PCT/EP2008/003473 describes a first way of synthesizing 3-(1-{3-[5-(1-methyl-piperidin-4-ylmethoxy)-pyrimidin-2-yl]-benzyl}-6-oxo-1,6-dihydro-pyridazin-3-yl)-benzonitrile. Hemisulfate, citrate, tartrate, sulfate, succinate and hydrochloride are mentioned as possible salt forms. Besides, example 43 of PCT/EP2008/003473 describes an alternative way of synthesizing 3-(1-{3-[5-(1-methylpiperidin-4-ylmethoxy)-pyrimidin-2-yl]-benzyl}-6-oxo-1,6-dihydro-pyridazin-3-yl)-benzonitrile. Example 3 of PCT/EP2008/005508 describes the same first way of synthesizing 3-(1-{3-[5-(1-methyl-piperidin-4-ylmethoxy)-pyrimidin-2-yl]-benzyl}-6-oxo-1,6-dihydro-pyridazin-3-yl)-benzonitrile and also mentions hemisulfate, citrate, tartrate, sulfate, succinate and hydrochloride as possible salt forms. Example 4 of PCT/EP20081/005508 refers to hydrochloride monohydrate (compound "A7"), hydrobromide, mesylate, besylate, malate, fumurate, maleate and p-tosylate salt forms. However, compound "A7" described in example 4 is not any monohydrate or monohydrate mixture, but exclusively crystalline modification H2 of 3-(1-{3-[5-(1-methylpiperidin-4-ylmethoxy)-pyrimidin-2-yl]-benzyl}-6-oxo-1,6-dihydro-pyridazin-3-yl)-benzonitrile hydrochloride monohydrate (please refer to Example 12 described herein).

Both prior art documents are silent about 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride solvate forms other than monohydrate crystalline modification H2.

Certain crystalline, i.e. morphological or polymorphic forms of pharmaceutical compounds may be of interest to those involved in the development of suitable pharmaceutical dosage forms. This is because if a certain polymorphic form is not held constant during clinical and stability studies, the exact dosage used or measured may not be comparable from one batch to the other. Once a pharmaceutical compound is produced for use, it is important to verify the morphological or polymorphic form delivered in each dosage form to assure that the production process delivers the same form and that the same amount of drug is included in each dosage. Therefore, it is imperative to assure that either a single morphological or polymorphic form or a known combination of morphological or polymorphic forms is present. In addition, certain morphological or polymorphic forms may exhibit enhanced thermodynamic stability and may be more suitable than other morphological or polymorphic forms for inclusion in pharmaceutical formulations.

The citation of any reference in this application is not an admission that the reference is relevant prior art to this application.

DESCRIPTION OF THE INVENTION

The present invention has the object to provide novel solvate forms of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride as well as novel polymorphic forms thereof.

The object of the present invention has surprisingly been solved in one aspect by providing 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride solvate excluding 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate crystalline modification H2.

In another aspect, the object of the present invention has surprisingly been solved by providing 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride solvate excluding 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate.

It has been found that 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride is able to form solvates in crystalline modifications. Examples of such solvates include solvates from water, solvates from alcohols such as methanol, ethanol, propan-1-ol or propan-2-ol; solvates from organic esters such as ethyl acetate; solvates from nitriles such as acetonitrile; solvates from ketones such as acetone and butanone; solvates from ethers such as tetrahydrofuran (THF) and solvates from chlorinated hydrocarbons such as chloroform and solvates of hydrocarbons such as n-heptane or toluene. Preferred solvates are formed with polar solvents, preferably water, alcohols, organic esters, nitriles, ketones and ethers.

Preferably, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride forms anhydrates and solvates with water, acetone, tetrahydrofuran, methanol, ethyl acetate or n-heptane in crystalline modifications that means the bound solvent together with 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride build the crystal structure. The molar ratio of the solvent to 3-(1-{3-[5-(1- methyl-piperidin-4-ylmethoxy)-pyrimidin-2-yl]-benzyl}-6-oxo-1,6-dihydro-pyridazin-3-yl)-benzonitrile hydrochloride could vary as known to skilled persons in the art. Preferably, the molar ratio is between 0.25:1 to 2.5:1, more preferably between 0.5:1 to 1:1, most preferably 1:1 (n-heptane solvate 1/15:1). It should be understood that the present anhydrates and solvates of the invention may contain unbound water that is to say water which is other than water of crystallization.

Further, the molar ratio of hydrochloride to 3-(1-{3-[5-(1-methyl-piperidin-4-ylmethoxy)-pyrimidin-2-yl]-benzyl}-6-oxo-1,6-dihydro-pyridazin-3-yl)-benzonitrile (free base) within 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride can vary for each and all the herein disclosed solvates, anhydrates, hydrates, monohydrates etc. and their crystalline modifications as known to skilled person in the art. Preferably, the molar ratio is between 0, 5:1 to 1, 5:1, more preferably between 0, 8:1 to 1, 2:1, most preferably 1:1.

Hence, in a preferred embodiment, 3-(1-{3-[5-(1-methyl-pipendin-4-ylmethoxy)-pyrimidin-2-yl]-benzyl}-6-oxo-1,6-dihydro-pyridazin-3-yl)-benzonitrile hydrochloride solvate excluding 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate crystalline modification H2 is provided in its crystalline modifications.

Hence, in a further preferred embodiment, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride solvate excluding 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate is provided in its crystalline modifications.

The object of the present invention has surprisingly been solved in another aspect by providing 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate.

In a preferred embodiment, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate is provided in its crystalline modification A1, which is characterized by XRD peaks comprising 4.4°, 15.9° and 22.7° (in °2θ using Cu—K$\alpha_1$ radiation, ±0.1°).

In a preferred embodiment, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate is provided in its crystalline modification A1, which is characterized by the following XRD data:

| Form A1: | | |
|---|---|---|
| Peak No. | d/Å | °2θ (Cu-K$\alpha_1$ radiation) ±0.1° |
| 1 | 20.08 | 4.4 |
| 2 | 8.55 | 10.3 |
| 3 | 7.43 | 11.9 |
| 4 | 5.70 | 15.5 |
| 5 | 5.56 | 15.9 |
| 6 | 4.99 | 17.8 |
| 7 | 4.86 | 18.2 |
| 8 | 4.74 | 18.7 |
| 9 | 4.55 | 19.5 |
| 10 | 4.46 | 19.9 |
| 11 | 4.27 | 20.8 |
| 12 | 4.10 | 21.6 |
| 13 | 3.91 | 22.7 |
| 14 | 3.82 | 23.3 |
| 15 | 3.65 | 24.3 |

In a preferred embodiment, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate is provided in its crystalline modification NF6, which is characterized by XRD peaks comprising 16.8°, 18.2° and 25.8° (in °2θ using Cu—K$\alpha_1$ radiation, ±0.1°).

In a preferred embodiment, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate is provided in its crystalline modification NF6, which is characterized by the following XRD data:

| Form NF6: | | |
|---|---|---|
| Peak No. | d/Å | °2θ (Cu-K$\alpha_1$ radiation) ±0.1° |
| 1 | 17.66 | 5.0 |
| 2 | 11.07 | 8.0 |
| 3 | 10.53 | 8.4 |
| 4 | 9.35 | 9.4 |
| 5 | 8.77 | 10.1 |
| 6 | 6.55 | 13.5 |
| 7 | 5.83 | 15.2 |
| 8 | 5.26 | 16.8 |
| 9 | 4.88 | 18.2 |
| 10 | 4.54 | 19.5 |
| 11 | 4.48 | 19.8 |
| 12 | 4.38 | 20.3 |
| 13 | 4.06 | 21.9 |
| 14 | 3.66 | 24.3 |
| 15 | 3.50 | 25.4 |
| 16 | 3.45 | 25.8 |
| 17 | 3.32 | 26.8 |
| 18 | 3.27 | 27.2 |
| 19 | 3.21 | 27.8 |
| 20 | 3.12 | 28.6 |

In a preferred embodiment, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate is provided in its crystalline modification NF4, which is characterized by XRD peaks comprising 6.0°, 15.7° and 24.7° (in °2θ using Cu—K$\alpha_1$ radiation, ±0.1°).

In a preferred embodiment, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate is provided in its crystalline modification NF4, which is characterized by the following XRD data:

| Form NF4: | | |
|---|---|---|
| Peak No. | d/Å | °2θ (Cu-K$\alpha_1$ radiation) ±0.1° |
| 1 | 14.61 | 6.0 |
| 2 | 8.92 | 9.9 |
| 3 | 6.45 | 13.7 |
| 4 | 6.29 | 14.1 |
| 5 | 5.63 | 15.7 |
| 6 | 5.53 | 16.0 |

-continued

| Form NF4: | | |
|---|---|---|
| Peak No. | d/Å | °2θ (Cu-Kα₁ radiation) ±0.1° |
| 7 | 5.26 | 16.8 |
| 8 | 4.86 | 18.2 |
| 9 | 4.19 | 21.2 |
| 10 | 4.11 | 21.6 |
| 11 | 4.04 | 22.0 |
| 12 | 3.94 | 22.6 |
| 13 | 3.89 | 22.8 |
| 14 | 3.76 | 23.6 |
| 15 | 3.60 | 24.7 |
| 16 | 3.56 | 25.0 |
| 17 | 3.49 | 25.5 |
| 18 | 3.37 | 26.5 |
| 19 | 3.32 | 26.8 |
| 20 | 3.22 | 27.7 |

The object of the present invention has surprisingly been solved in another aspect by providing 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate excluding 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate crystalline modification H2.

The object of the present invention has surprisingly been solved in another aspect by providing 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate excluding 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate.

In a preferred embodiment, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate is provided in its crystalline modification H1, which is characterized by XRD peaks comprising 5.9°, 16.0° and 23.4° (in °2θ using Cu—Kα₁ radiation, ±0.1*).

In a preferred embodiment, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate is provided in its crystalline modification H1, which is characterized by the following XRD data:

| Form H1: | | |
|---|---|---|
| Peak No. | d/Å | °2θ (Cu-Kα₁ radiation) ±0.1° |
| 1 | 14.88 | 5.9 |
| 2 | 9.99 | 8.8 |
| 3 | 7.83 | 11.3 |
| 4 | 7.25 | 12.2 |
| 5 | 6.10 | 14.5 |
| 6 | 5.84 | 15.2 |
| 7 | 5.52 | 16.0 |
| 8 | 5.38 | 16.5 |
| 9 | 4.92 | 18.0 |
| 10 | 4.12 | 21.6 |
| 11 | 3.80 | 23.4 |
| 12 | 3.57 | 24.9 |
| 13 | 3.49 | 25.5 |
| 14 | 3.30 | 27.0 |
| 15 | 2.95 | 30.3 |

In a preferred embodiment, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate is provided in its crystalline modification NF3, which is characterized by XRD peaks comprising 9.9°, 15.7° and 24.1° (in °2θ using Cu—Kα₁ radiation, ±0.1°).

In a preferred embodiment, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate is provided in its crystalline modification NF3, which is characterized by the following XRD data:

| Form NF3: | | |
|---|---|---|
| Peak No. | d/Å | °2θ (Cu-Kα₁ radiation) ±0.1° |
| 1 | 14.83 | 6.0 |
| 2 | 8.96 | 9.9 |
| 3 | 6.92 | 12.8 |
| 4 | 5.62 | 15.7 |
| 5 | 5.44 | 16.3 |
| 6 | 5.26 | 16.9 |
| 7 | 4.38 | 20.3 |
| 8 | 4.32 | 20.6 |
| 9 | 3.79 | 23.5 |
| 10 | 3.69 | 24.1 |
| 11 | 3.59 | 24.8 |
| 12 | 3.55 | 25.1 |
| 13 | 3.45 | 25.8 |
| 14 | 3.35 | 26.6 |
| 15 | 3.22 | 27.7 |

In a preferred embodiment, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate is provided in its crystalline modification NF2, which is characterized by XRD peaks comprising 5.2°, 23.8° and 24.5° (in °2θ using Cu—Kα₁ radiation, ±0.1°).

In a preferred embodiment, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate is provided in its crystalline modification NF2, which is characterized by the following XRD data:

| Form NF2: | | |
|---|---|---|
| Peak No. | d/Å | °2θ (Cu-Kα₁ radiation) ±0.1° |
| 1 | 16.84 | 5.2 |
| 2 | 8.41 | 10.5 |
| 3 | 8.14 | 10.9 |
| 4 | 5.70 | 15.5 |
| 5 | 5.59 | 15.8 |
| 6 | 4.87 | 18.2 |
| 7 | 4.19 | 21.2 |
| 8 | 4.00 | 22.2 |
| 9 | 3.91 | 22.7 |
| 10 | 3.78 | 23.5 |
| 11 | 3.73 | 23.8 |
| 12 | 3.63 | 24.5 |
| 13 | 3.52 | 25.3 |
| 14 | 3.49 | 25.5 |
| 15 | 3.36 | 26.5 |
| 16 | 3.33 | 26.7 |
| 17 | 3.23 | 27.6 |
| 18 | 3.19 | 28.0 |
| 19 | 3.15 | 28.3 |
| 20 | 3.12 | 28.6 |

In a further preferred embodiment, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate is provided in its crystalline modification H2, which is characterized by the following XRD data:

Form H2:

| Peak No. | d/Å | °2θ (Cu-Kα₁ radiation) ±0.1° | (h, k, l) |
|---|---|---|---|
| 1 | 8.71 | 10.1 | (1, 0, 0) |
| 2 | 8.22 | 10.8 | (−1, 1, 1) |
| 3 | 7.59 | 11.6 | (1, 2, 0) |
| 4 | 6.78 | 13.0 | (0, 3, 1) |
| 5 | 6.58 | 13.5 | (−1, 3, 1) |
| 6 | 5.73 | 15.4 | (−1, 4, 1) |
| 7 | 4.98 | 17.8 | (−1, 1, 2) |
| 8 | 4.84 | 18.3 | (−2, 1, 1) |
| 9 | 4.68 | 19.0 | (−2, 2, 1) |
| 10 | 4.43 | 20.0 | (−2, 3, 1) |
| 11 | 4.35 | 20.4 | (2, 0, 0) |
| 12 | 3.73 | 23.9 | (−2, 4, 2) |
| 13 | 3.64 | 24.5 | (0, 5, 2) |
| 14 | 3.39 | 26.3 | (0, 6, 2) |
| 15 | 3.13 | 28.5 | (−3, 2, 2) |

In the course of the present invention, the term "crystalline modification" is used as a synonym for terms "crystalline form", "polymorphic form", "polymorphic modification", "morphological form" and the like.

The crystalline modifications of the present invention, in particular crystalline modification A1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate, crystalline modification NF6 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate, crystalline modification NF4 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate, crystalline modification H1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate, crystalline modification NF3 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate, crystalline modification NF2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate, and crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate, are surprisingly characterized by, among others, a reduced hygroscopicity, a better compressibility during the tableting process, a prolonged shelf life, a better thermodynamic stability, i.e. stability against heat and humidity, a better resistance to sunlight, i.e. UV-light, an increased bulk density, an improved solubility, bioavailability characteristics which are constant from one batch to the other, better flow and handling properties in the tableting process, an improved colour stability and better filtration properties in the production process. Therefore, by use of the crystalline modifications of the present invention, it is possible to obtain pharmaceutical formulations with improved homogeneity, stability, purity and uniformity from one batch to the other.

Furthermore, crystalline modification A1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate shows superior properties for drying purposes (no loss of hydrate water can occur) as well as significantly increased solubility in USP Simulated Gastric Juice compared to the thermodynamically stable crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate.

Crystalline modification H1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate shows significantly increased solubility in 0.1N HCl (pH 1.0) compared to the thermodynamically stable crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate.

On the other hand, crystalline modification NF3 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate shows significantly increased solubility in 0.1 N HCl (pH 1.0) compared to the thermodynamically stable crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate.

In contrast, crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate represents the thermodynamically stable hydrate form and shows superior properties in terms of hygroscopicity behavior compared to 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate crystalline modifications H1 and NF3, as well as to 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate crystalline modification A1, namely physical stability of the crystal form throughout the entire RH range 0-98% with very small water uptake levels.

The crystalline modifications of the present invention can be characterized according to standard methods which can be found e.g. in Rolf Hilfiker, 'Polymorphism in the Pharmaceutical Industry', Wiley-VCH, Weinheim 2006, and references therein, e.g. X-Ray diffraction (XRD; chapter 6), IR and Raman spectroscopy (chapter 5), Differential Scanning Calorimetry (DSC) and Thermogravimetric Analysis (TGA) (chapter 3), Water Vapour Sorption Studies (chapter 9), or which can be found e.g. in H. G. Brittain (editor), Polymorphism in Pharmaceutical Solids, Vol. 95, Marcel Dekker Inc., New York 1999 (chapter 6: all there mentioned techniques).

3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride solvate excluding 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate crystalline modification H2, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride solvate excluding 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride solvate excluding 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate crystalline modification H2 in its crystalline modifications, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride solvate excluding 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate in its crystalline modifications, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate excluding 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate crystalline modification H2, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate excluding 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate in its crystalline modification A1, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate in its crystalline modification NF6, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate in its crystalline modification NF4, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate in its crystalline modification H1, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate in its crystalline modification NF3, 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate in its crystalline modification NF2, and 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate in its crystalline modification H2 are hereinafter referred to as "product(s) of the (present) invention".

3-(1-{3-[5-(1-methyl-piperidin-4-ylmethoxy)-pyrimidin-2-yl]-benzyl}-6-oxo-1,6-dihydro-pyridazin-3-yl)-benzonitrile (free base) can be synthesized as described in PCT/EP2008/003473, example 40, and PCT/EP2008/005508, example 3, as follows:

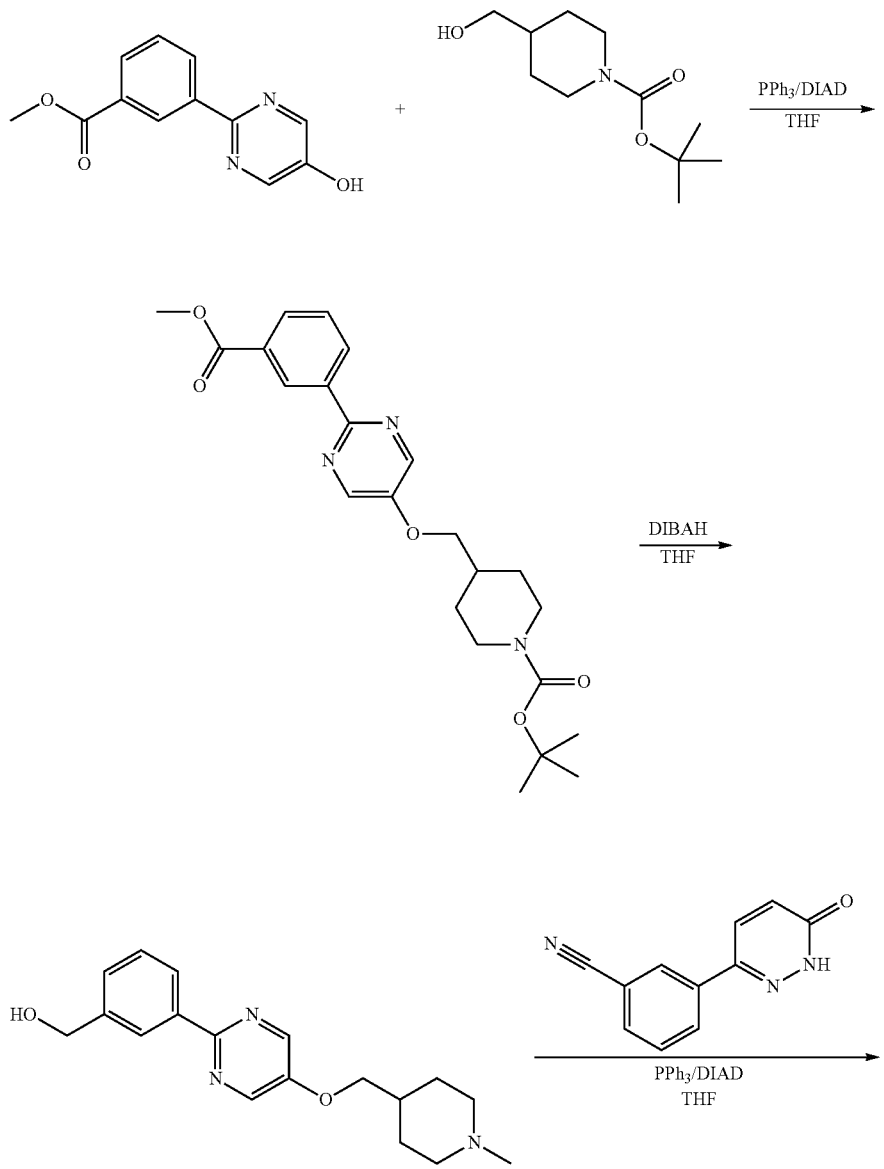

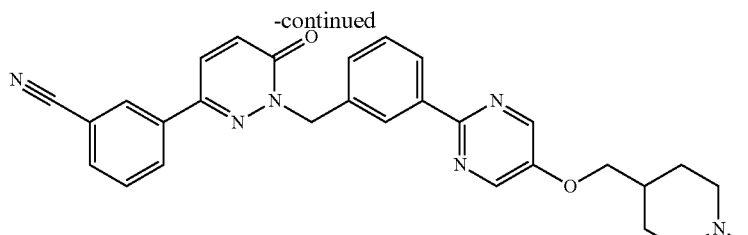

"A257"

To a suspension of 13.0 g (56.5 mmol) of 3-(5-hydroxy-pyrimidin-2-yl)-benzoic acid methylester and 13.4 g (62.1 mmol) of N-Boc-piperidinemethanol in 115 ml THF 17.7 g (67.8 mmol) of triphenyl-phosphine are given. The suspension is cooled down to 5° C. To the suspension kept at this temperature 13.3 ml (67.8 mmol) of diisopropylazodicarboxylate are given dropwise under stirring within 45 minutes. The reaction mixture is stirred at room temperature for one hour. Subsequently, further 22.2 g (84.7 mmol) of triphenylphosphine and 16.6 ml (84.7 mmol) of diisopropylazodicarboxylate are added. The reaction mixture is stirred at room temperature for 18 hours and concentrated in vacuo. The resulting solid of 4-[2-(3-methoxycarbonyl-phenyl)-pyrimidin-5-yloxymethyl]-piperidine-1-carbonic acid tert.-butylester is sucked off, washed with diethylether and subjected to chromatography (silica gel column and dichloromethan/methanol as eluent/mobile phase).

To a suspension of 1.71 g (3.99 mmol) of 4-[2-(3-methoxycarbonyl-phenyl)-pyrimidin-5-yloxymethyl]-piperidine-1-carbonic acid tert.-butylester in 20 ml THF 25 ml (25 mmol) of a 1 M solution of diisobutylaluminiumhydride in THF are given dropwise under nitrogen. The reaction mixture is stirred for one hour at room temperature and mixed with a saturated solution of sodium sulfate. The resulting precipitate is sucked off and washed with THF and hot 2-propanol. The filtrate is concentrated and re-crystallized from tert.-butylmethylether, resulting in {3-[5-(1-methyl-piperidin-4-ylmethoxy)-pyrimidin-2-yl]-phenyl}-methanol as beige crystals.

To a solution of 313 mg (1.00 mmol) of {3-[5-(1-methylpiperidin-4-ylmethoxy)-pyrimidin-2-yl]-phenyl}-methanol in 2 ml THF 264 mg (1.30 mmol) of 3-(6-oxo-1,6-dihydropyridazin-3-yl)-benzonitrile and 397 mg (1.5 mmol) triphenylphosphine are added subsequently. The reaction mixture is cooled in an ice bath and 294 µl (1.5 mmol) of diisopropylazodicarboxylate are added dropwise. The reaction mixture is stirred at room temperature for 18 hours and then concentrated. The residue is subjected to chromatography (silica gel column and dichloromethan/methanol as eluent/mobile phase). The product containing fractions are pooled, concentrated and the residue of 3-(1-{3-[5-(1-Methyl-piperidin-4-ylmethoxy)-pyrimidin-2-yl]-benzyl}-6-oxo-1,6-dihydro-pyridazin-3-yl)-benzonitrile is decocted with tert.-butylmethylether, sucked off and dried in vacuo.

Alternatively, 3-(1-{3-[5-(1-methyl-piperidin-4-ylmethoxy)-pyrimidin-2-yl]-benzyl}-6-oxo-1,6-dihydro-pyridazin-3-yl)-benzonitrile (free base) can be synthesized as described in PCT/EP2008/003473, example 43, as follows:

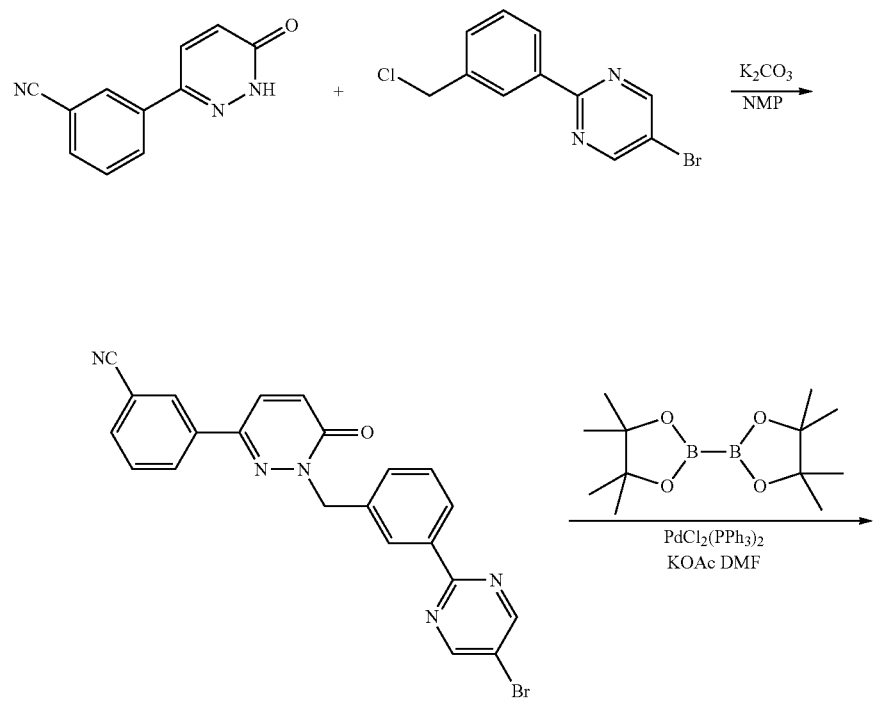

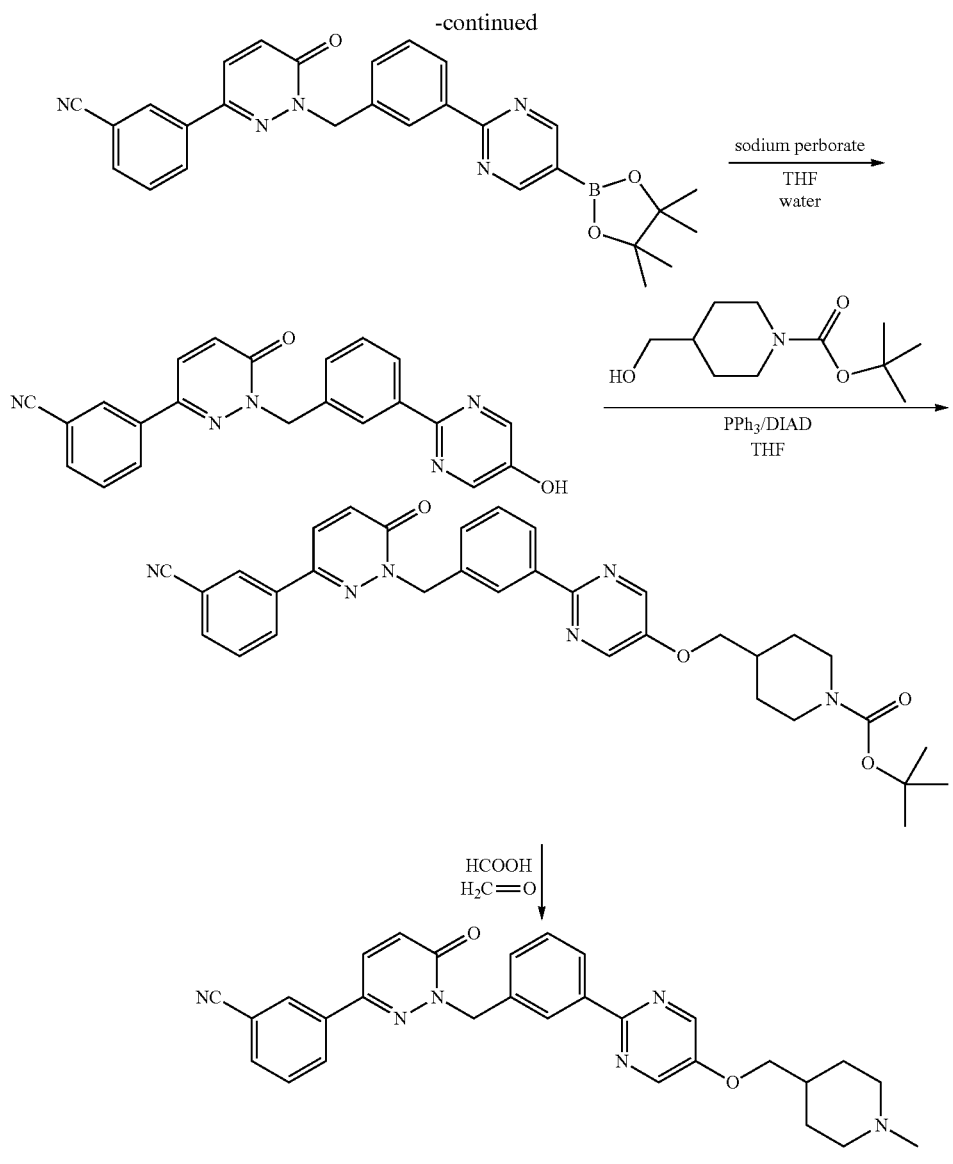

"A257"

To a suspension of 4.15 g (20 mmol) of 3-(6-oxo-1,6-dihydro-pyridazin-3-yl)-benzonitrile in 40 ml of 1-methyl-2-pyrrolidon 6.00 g (21 mmol) of 5-bromo-2-(3-chloromethyl-phenyl)-pyrimidine and 2.76 g (341 mmol) of potassiumcarbonate are given. The reaction mixture is stirred at 80° C. for 18 hours. Subsequently, the reaction mixture is given onto 200 ml water. The resulting precipitate of 3-{1-[3-(5-bromopyrimidin-2-yl)-benzyl]-6-oxo-1,6-dihydro-pyridazin-3-yl}-benzonitrile is sucked off, washed with water and dried in vacuo.

To a solution of solution of 18.0 g (41.0 mmol) of 3-{1-[3-(5-bromopyrimidin-2-yl)-benzyl]-6-oxo-1,6-dihydro-pyridazin-3-yl}-benzonitrile in 85 ml DMF 11.8 g (47 mmol) of bis(pinacolato)diboron and 11.9 g (122 mmol) of potassium acetate are given. The reaction mixture is heated up to 80° C. under nitrogen. After 15 minutes of stirring at this temperature 273 mg (1.22 mmol) of palladium(II)-acetate are added and the reaction mixture is stirred for 2 hours at 80° C. under nitrogen. Subsequently, the reaction mixture is allowed to cool down to room temperature before the addition of water and dichloromethane, filtration over diatomite/kieselguhr and separation of the organic phase. The organic phase is dried over sodium sulphate and concentrated yielding 3-(6-oxo-1-{3-[5-(4,4,5,5-tetramethyl-[1,3,2]dioxaborolan-2-yl)-pyrimidin-2-yl]-benzyl}-1,6-dihydro-pyridazin-3-yl)-benzonitrile as grey solid, which can be used for subsequent reactions without purification.

To a suspension of 5.33 g (10.9 mmol) of 3-(6-oxo-1-{3-[5-(4,4,5,5-tetramethyl-[1,3,2]dioxaborolan-2-yl)-pyrimidin-2-yl]-benzyl}-1,6-dihydro-pyridazin-3-yl)-benzonitrile in 35 ml THF and 35 ml water 4.93 g (49.4 mmol) of sodiumperborate are given in portions under ice cooling before it is stirred at room temperature for 2 hours. The reaction mixture is mixed with 300 ml of dichloromethan and 100 ml of saturated ammoniumchloride solution. The organic phase is separated, dried over sodium sulphate and concentrated. The residue of 3-{1-[3-(5-hydroxy-pyrimidin-2-yl)-benzyl]-6-oxo-1,6-dihydro-pyridazin-3-yl}-benzonitrile is re-crystallized from methanol.

To a suspension of 25 g (65.6 mmol) of 3-{1-[3-(5-hydroxy-pyrimidin-2-yl)-benzyl]-6-oxo-1,6-dihydro-pyridazin-3-yl}-benzonitrile in 250 ml THF 15.6 g (68.8 mmol) of N-Boc-4-piperidine-methanol and 19.1 g (72.1 mmol) of triphenylphosphine are subsequently added. Then, 14.9 ml (72.1 mmol) of diisopropylazodicarboxylate are added dropwise under ice cooling. The resulting solution is stirred at room temperature for 2 hours. The reaction mixture is further mixed with 750 ml of 2-propanol and 13.1 ml of a 0.5 M solution of potassiumhydroxid in ethanol. The resulting precipitate of 4-(2-{3-[3-(3-cyano-phenyl)-6-oxo-6H-pyridazin-1-ylmethyl]-phenyl}-pyrimidin-5-yloxymethyl)-piperidine-1-carbonic acid tert.-butylester is sucked off, washed with diethylether and dried in vacuo.

To a solution of 16.0 g (28.0 mmol) of 4-(2-{3-[3-(3-cyano-phenyl)-6-oxo-6H-pyridazin-1-ylmethyl]-phenyl}-pyrimidin-5-yloxymethyl)-piperidine-1-carbonic acid tert.-butylester in 80 ml formic acid 6.60 ml of 35% aqueous formaldehyde solution are given. The reaction mixture is stirred at a temperature of 110° C. for 2 hours before 300 ml water are added. The reaction mixture is concentrated in vacuo to a volume of 150 ml and is then extracted with 200 ml of dichloromethane. The organic phase is washed with sodiumbicarbonate solution, dried over sodium sulphate and concentrated. The residue of 3-(1-{3-[5-(1-methyl-piperidin-4-ylmethoxy)-pyrimidin-2-yl]-benzyl}-6-oxo-1,6-dihydro-pyridazin-3-yl)-benzonitrile is re-crystallized from 2-propanol.

In another aspect of the invention, a pharmaceutical composition comprising a therapeutically effective amount of at least one product of the invention is provided.

In a preferred embodiment, the pharmaceutical composition further comprises at least one additional compound selected from the group consisting of physiologically acceptable excipients, auxiliaries, adjuvants, diluents, carriers and/or additional pharmaceutically active substances other than the products of the invention.

A further embodiment of the present invention is a process for the manufacture of said pharmaceutical compositions, characterized in that one or more products of the invention and one or more compounds selected from the group consisting of solid, liquid or semiliquid excipients, auxiliaries, adjuvants, diluents, carriers and pharmaceutically active substances other than the products of the invention, are converted in a suitable dosage form.

As used herein, the term "effective amount" refers to any amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

In another aspect of the invention, a medicament comprising at least one product of the invention or a pharmaceutical composition as described herein is provided.

In a further aspect of the invention, a medicament as described herein for use in the treatment and/or prophylaxis of physiological and/or pathophysiological conditions, which are caused, mediated and/or propagated by the inhibition, regulation and/or modulation of signal transduction of kinases, in particular by the inhibition of tyrosine kinases, preferably Met-kinase, is provided. A corresponding use for the preparation of a medicament for the treatment and/or prophylaxis of the aforementioned conditions is intended to be comprised.

In a further aspect of the invention, a medicament as described herein for use in the treatment and/or prophylaxis of physiological and/or pathophysiological conditions selected from the group consisting of: "cancer, tumour, malignant tumours, benign tumours, solid tumours, sarcomas, carcinomas, hyperproliferative disorders, carcinoids, Ewing sarcomas, Kaposi sarcomas, brain tumours, tumours originating from the brain and/or the nervous system and/or the meninges, gliomas, glioblastomas, neuroblastomas, stomach cancer, kidney cancer, kidney cell carcinomas, prostate cancer, prostate carcinomas, connective tissue tumours, soft tissue sarcomas, pancreas tumours, liver tumours, head tumours, neck tumours, laryngeal cancer, oesophageal cancer, thyroid cancer, osteosarcomas, retinoblastomas, thymoma, testicular cancer, lung cancer, lung adenocarcinoma, small cell lung carcinoma, bronchial carcinomas, breast cancer, mamma carcinomas, intestinal cancer, colorectal tumours, colon carcinomas, rectum carcinomas, gynaecological tumours, ovary tumours/ovarian tumours, uterine cancer, cervical cancer, cervix carcinomas, cancer of body of uterus, corpus carcinomas, endometrial carcinomas, urinary bladder cancer, urogenital tract cancer, bladder cancer, skin cancer, epithelial tumours, squamous epithelial carcinoma, basaliomas, spinaliomas, melanomas, intraocular melanomas, leukaemias, monocyte leukaemia, chronic leukaemias, chronic myelotic leukaemia, chronic lymphatic leukemia, acute leukaemias, acute myelotic leukaemia, acute lymphatic leukaemia and/or lymphomas" is provided. A corresponding use for the preparation of a medicament for the treatment and/or prophylaxis of the aforementioned conditions is intended to be comprised.

In another aspect of the invention, a medicament as described herein is provided, wherein in such medicament comprises at least one additional pharmacologically active substance (drug, ingredient).

In a preferred embodiment the at least one pharmacologically active substance is a substance as described herein.

In another aspect of the invention, a medicament as described herein is provided, wherein the medicament is applied before and/or during and/or after treatment with at least one additional pharmacologically active substance.

In a preferred embodiment the at least one pharmacologically active substance is a substance as described herein.

In a further aspect of the invention, a kit comprising a therapeutically effective amount of at least one product of the invention and/or at least one pharmaceutical composition as described herein and a therapeutically effective amount of at least one further pharmacologically active substance other than the products of the invention is provided.

Products of the invention may be used in combination with one or more other pharmacologically active substances (ingredients, drugs) in the treatment, prevention, suppression or amelioration of diseases or conditions for which products of the invention or the other substances have utility. Typically the combination of the drugs is safer or more effective than either drug alone, or the combination is safer or more effective than would it be expected based on the additive properties of the individual drugs. Such other drug(s) may be administered, by a route and in an amount commonly used contemporaneously or sequentially with a product of the invention. When a product of the invention is used contemporaneously with one or more other drugs, a combination product containing such other drug(s) and the product of the invention is preferred. However, combination therapy also includes therapies in which the product of the invention and one or more other drugs are administered on different overlapping schedules. It is contemplated that when used in combination with other active ingredients, the product of the present invention or the other active ingredient or both may be used effectively in lower doses than when each is used alone. Accordingly, the pharmaceutical compositions of the present invention (pharmaceutical compositions as described herein) include those that contain one or more other active ingredients, in addition to a product of the invention.

Examples of other pharmacologically active substances (ingredients, drugs) that may be administered in combination with a product of the invention, and either administered separately or in the same pharmaceutical composition, include, but are not limited to the compounds classes and specific compounds listed in Table 1:

TABLE 1

| | | |
|---|---|---|
| Alkylating agents | Cyclophosphamide | Lomustine |
| | Busulfane | Procarbazine |
| | Ifosfamide | Altretamine |
| | Melphalane | Estramustinphosphate |
| | Hexamethylmelamine | Mechlorethamine |
| | Thiotepa | Streptozocine |
| | Chlorambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (AeternaZentaris) |
| | Carboxyphthalatoplatinum | Satraplatin (Johnson Matthey) |
| | Tetraplatin | BBR-3464 (Hoffmann-La |
| | Ormiplatin | Roche) |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycine |
| | 5-Fluoruracil | Fludarabine |
| | Floxuridine | Pentostatine |
| | 2-Chlordesoxyadenosine | Raltitrexede |
| | 6-Mercaptopurine | Hydroxyurea |
| | 6-Thioguanine | Decitabine (SuperGen) |
| | Cytarabine | Clofarabine (Bioenvision) |
| | 2-Fluordesoxycytidine | Irofulven (MGI Pharma) |
| | Methotrexate | DMDC (Hoffmann-La Roche) |
| | Idatrexate | Ethinylcytidine (Taiho) |
| Topoisomerase inhibitors | Amsacrine | Rubitecane (SuperGen) |
| | Epirubicine | Exatecanmesylate (Daiichi) |
| | Etoposide | Quinamed (ChemGenex) |
| | Teniposide or Mitoxantrone | Gimatecane (Sigma-Tau) |
| | Irinotecane (CPT-11) | Diflomotecane (Beaufour-Ipsen) |
| | 7-Ethyl-10-hydroxycamptothecine | TAS-103 (Taiho) |
| | Topotecane | Elsamitrucine (Spectrum) |
| | Dexrazoxanet (TopoTarget) | J-107088 (Merck & Co) |
| | Pixantrone (Novuspharrna) | BNP-1350 (BioNumerik) |
| | Rebeccamycin-Analogue (Exelixis) | CKD-602 (Chong Kun Dang) |
| | BBR-3576 (Novuspharrna) | KW-2170 (Kyowa Hakko) |
| Antitumor antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycinsulfate (Blenoxan) |
| | Therarubicin | Bleomycinacid |
| | Idarubicin | Bleomycin A |
| | Rubidazone | Bleomycin B |
| | Plicamycinp | Mitomycin C |
| | Porfiromycin | MEN-10755 (Menarini) |
| | Cyanomorpholinodoxorubicin | GPX-100 (Gem Pharmaceuticals) |
| | Mitoxantron (Novantron) | |
| Antimitotic agents | Paclitaxel | SB 408075 (Glaxo SmithKline) |
| | Docetaxel | E7010 (Abbott) |
| | Colchicin | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatine 10 (NCI) | D 24851 (ASTA Medica) |
| | Rhizoxine (Fujisawa) | ER-86526 (Eisai) |
| | Mivobuline (Warner-Lambert) | Combretastatine A4 (BMS) |
| | Cemadotine (BASF) | Isohomohalichondrin-B |
| | RPR 109881A (Aventis) | (PharmaMar) |
| | TXD 258 (Aventis) | |

TABLE 1-continued

| | | |
|---|---|---|
| | Epothilon B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatine PE (Teikoku Hormone) | Azaepothilon B (BMS) |
| | BMS 247550 (BMS) | BNP-7787 (BioNumerik) |
| | BMS 184476 (BMS) | CA-4-Prodrug (OXiGENE) |
| | BMS 188797 (BMS) | Dolastatin-10 (NrH) |
| | Taxoprexine (Protarga) | CA-4 (OXiGENE) |
| Aromatase inhibitors | Aminoglutethimide | Exemestane |
| | Letrozole | Atamestane (BioMedicines) |
| | Anastrazole | YM-511 (Yamanouchi) |
| | Formestane | |
| Thymidylatesynthase inhibitors | Pemetrexed (Eli Lilly) | Nolatrexed (Eximias) |
| | ZD-9331 (BTG) | CoFactor ™ (BioKeys) |
| DNA antagonists | Trabectedine (PharmaMar) | Mafosfamide (Baxter International) |
| | Glufosfamide (Baxter International) | Apaziquone (Spectrum Pharmaceuticals) |
| | Albumin + 32P (Isotope Solutions) | |
| | Thymectacine (NewBiotics) | O6-Benzylguanine (Paligent) |
| | Edotreotide (Novartis) | |
| Farnesyltransferase inhibitors | Arglabine (NuOncology Labs) | Tipifarnibe (Johnson & Johnson) |
| | Ionafarnibe (Schering-Plough) | Perillylalcohol (DOR Bio-Pharma) |
| | BAY-43-9006 (Bayer) | |
| Pump inhibitors | CBT-1 (CBA Pharma) | Zosuquidar-Trihydrochloride (Eli Lilly) |
| | Tariquidar (Xenova) | |
| | MS-209 (Schering AG) | Biricodar-Dicitrate (Vertex) |
| Histoneacetyltransferase inhibitors | Tacedinaline (Pfizer) | Pivaloyloxymethylbutyrate (Titan) |
| | SAHA (Aton Pharma) | |
| | MS-275 (Schering AG) | Depsipeptide (Fujisawa) |
| Metalloproteinase inhibitors/ | Neovastat (Aeterna Laboratories) | CMT-3 (CollaGenex) |
| | | BMS-275291 (Celltech) |
| Ribonucleosidereduktase inhibitors | Marimastat (British Biotech) | Tezacitabine (Aventis) |
| | Galliummaltolate (Titan) | Didox (Molecules for Health) |
| | Triapine (Vion) | |
| TNF-alpha agonists/ antagonists | Virulizine (Lorus Therapeutics) | Revimide (Celgene) |
| | CDC-394 (Celgene) | |
| Endotheline-A receptor antagonists | Atrasentane (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | Pentrix (Australian Cancer Technology) |
| | GMK (Progenics) | |
| | Adenocarzinoma vaccine (Biomira) | JSF-154 (Tragen) |
| | | Cancer vaccine (Intercell) |
| | CTP-37 (AVI BioPharma) | Noreline (Biostar) |
| | JRX-2 (Immuno-Rx) | BLP-25 (Biomira) |
| | PEP-005 (Peplin Biotech) | MGV (Progenics) |
| | Synchrovax vaccine (CTL Immuno) | 13-Alethine (Dovetail) |
| | Melanoma vaccine (CTL Immuno) | CLL-Thera (Vasogen) |
| | p21-RAS vaccine (GemVax) | |
| Hormonal and anti-hormonal agents | Estrogens | Prednisone |
| | Conjugated Estrogens | Methylprednisolone |
| | Ethinylestradiole | Prednisolone |
| | Chlorotrianisen | Aminoglutethimide |
| | Idenestrole | Leuprolide |
| | Hydroxyprogesteroncaproate | Goserelin |
| | Medroxyprogesterone | Leuporelin |
| | Testosterone | Cetrorelix |
| | Testosteronpropionate | Bicalutamide |
| | Fluoxymesterone | Flutamide |
| | Methyltestosterone | Octreotide |
| | Diethylstilbestrole | Nilutamide |
| | Megestrole | Mitotane |
| | Tamoxifen | P-04 (Novogen) |
| | Toremofine | 2-Methoxyestradiol (EntreMed) |
| | Dexamethasone | Arzoxifen (Eli Lilly) |
| Photodynamic agents | Talaporfine (Light Sciences) | Pd-Bacteriopheophorbide (Yeda) |
| | Theralux (Theratechnologies) | |
| | Motexafin Gadolinium (Pharmacyclics) | Lutetium-Texaphyrine (Pharmacyclics) |
| | | Hypericine |
| Tyrosinkinase inhibitors | Imatinib (Novartis) | Kahalid F (PharmaMar) |
| | Leflunomid (Sugen/Pharmacia) | CEP-701 (Cephalon) |
| | | CEP-751 (Cephalon) |

TABLE 1-continued

| | | |
|---|---|---|
| | ZDI839 (AstraZeneca) | MLN518 (Millenium) |
| | Erlotinib (Oncogene Science) | PKC412 (Novartis) |
| | Canertjnib (Pfizer) | Phenoxodiol O |
| | Squalamin (Genaera) | Trastuzumab (Genentech) |
| | SU5416 (Pharmacia) | C225 (ImClone) |
| | SU6668 (Pharmacia) | rhu-Mab (Genentech) |
| | ZD4190 (AstraZeneca) | MDX-H210 (Medarex) |
| | ZD6474 (AstraZeneca) | 2C4 (Genentech) |
| | Vatalanib (Novartis) | MDX-447 (Medarex) |
| | PKI166 (Novartis) | ABX-EGF (Abgenix) |
| | GW2016 (GlaxoSmithKline) | IMC-1C11 (ImClone) |
| | EKB-509 (Wyeth) | |
| | EKB-569 (Wyeth) | |
| Different agents | SR-27897 (CCK-A inhibitor, Sanofi-Synthelabo) | BCX-1777 (PNP inhibitor, BioCryst) |
| | Tocladesine (cyclic-AMP agonist, Ribapharm) | Ranpirnase (Ribonuclease stimulans, Alfacell) |
| | Alvocidib (CDK inhibitor, Aventis) | Galarubicin (RNA synthesis inhibitor, Dong-A) |
| | CV-247 (COX-2-Inhibitor, Ivy Medical) | Tirapazamin (reducing agent, SRI International) |
| | P54 (COX-2 inhibitor, Phytopharm) | N-Acetylcystein (reducing agent, Zambon) |
| | CapCell ™ (CYP450 stimulans, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (Gastrin inhibitor, Aphton) | Seocalcitol (Vitamin-D receptor agonist, Leo) |
| | Efaproxiral (Oxygenator, Allos Therapeutics) | 131-I-TM-601 (DNA antagonist, TransMolecular) |
| | PI-88 (Heparanase inhibitor, Progen) | Eflornithin (ODC inhibitor, ILEX Oncology) |
| | Tesmilifen (Histamine antagonist, YM BioSciences) | Minodronic acid (Osteoclasts inhibitor, Yamanouchi) |
| | Histamine (Histamine-H2 receptor agonist, Maxim) | Indisulam (p53 stimulans, Eisai) |
| | Tiazofurin (IMPDH inhibitor, Ribapharm) | Aplidin (PPT inhibitor, PharmaMar) |
| | Cilengitide (Integrine antagonist, Merck KGaA) | Rituximab (CD20 antibody, Genentech) |
| | SR-31747 (IL-1 antagonist, Sanofi-Synthelabo) | Gemtuzumab (CD33 antibody, Wyeth Ayerst) |
| | CCI-779 (mTOR kinase inhibitor, Wyeth) | PG2 (Hematopoesis enhancer, Pharmagenesis) |
| | Exisulind (PDE-V inhibitor, Cell Pathways) | Immunol ™ (Triclosan oral irrigation, Endo) |
| | CP-461 (PDE-V inhibitor, Cell Pathways) | Triacetyluridine (Uridine pro-drug, Wellstat) |
| | AG-2037 (GART inhibitor, Pfizer) | SN-4071 (sarcoma agent, Signature BioScience) |
| | WX-UK1 (Plasminogen activator inhibitor, Wilex) | TransMID-107 ™ (Immunotoxine, KS Biomedix) |
| | PBI-1402 (PMN stimulans, ProMetic LifeSciences) | PCK-3145 (Apoptosis enhancer, Procyon) |
| | Bortezomib (Proteasome inhibitor, Millennium) | Doranidazole (Apoptosis enhancer, Pola) |
| | SRL-172 (T-cell stimulans, SR Pharma) | CHS-828 (cytotoxic agent, Leo) |
| | TLK-286 (Glutathione-S-transferase inhibitor, Telik) | trans-Retinoic acid (Differentiator, NIH) |
| | PT-100 (Growth factor agonist, Point Therapeutics) | MX6 (Apoptosis enhancer, MAXIA) |
| | Midostaurin (PKC inhibitor, Novartis) | Apomin (Apoptosis enhancer, ILEX Oncology) |
| | Bryostatin-1 (PKC stimulans, GPC Biotech) | Urocidine (Apoptosis enhancer, Bioniche) |
| | CDA-II (Apoptosis enhancer, Everlife) | Ro-31-7453 (Apoptosis enhancer, La Roche) |
| | SDX-101 (Apoptosis enhancer, Salmedix) | Brostallicin (Apoptosis enhancer, Pharmacia) |
| | Ceflatonin (Apoptosis enhancer, ChemGenex) | |

In a preferred embodiment, a product of the invention is administered in combination with one or more known antitumor agents, such as the following: estrogen receptor modulators, androgen receptor modulators, retinoid receptor modulators, cytotoxics, antiproliferative agents, prenyl proteintransferase inhibitors, HMG-CoA-reductase inhibitors, HIV protease inhibitors, reverse transcriptase inhibitors, angiogenesis inhibitors.

The products of the invention are in particular well suited for administration in combination with radiotherapy. The synergistic effects of VEGF inhibition in combination with radiotherapy are known to the skilled artisan (WO 00/61186).

The term "estrogen receptor modulators" in the course of the present invention refers to compounds that interfere with or inhibit the binding of estrogen to estrogen receptor—independently from the mode of action. Non-limiting examples of estrogen receptor modulators are tamoxifen, raloxifen, idoxifen, LY353381, LY117081, toremifen, fulvestrant, 4-[7-(2, 2-Dimethyl-1-oxopropoxy-4-methyl-2-[4-[2-(1-piperidinyl) ethoxy]phenyl]-2H-1-benzopyran-3-yl]phenyl-2,2-dimethyl-propanoate, 4,4'-Dihydroxybenzophenon-2,4-dinitrophenylhydrazone and SH646.

The term "androgen receptor modulators" in the course of the present invention refers to compounds that interfere with or inhibit the binding of androgens to androgen receptor—independently from the mode of action. Non-limiting examples of androgen receptor modulators are finasteride and other 5alpha-reductase inhibitors, nilutamide, flutamide, bicalutamide, liarozole and abirateron acetate.

The term "retinoid receptor modulators" in the course of the present invention refers to compounds that interfere with or inhibit the binding of retinoids to retinoid receptor—independently from the mode of action. Non-limiting examples of retinoid receptor modulators are bexaroten, tretinoin, 13-cis-retinoic acid, 9-cis-retinoic acid, alpha-difluoromethylomithine, ILX23-7553, trans-N-(4'-Hydroxyphenyl)retinamide and N-4-carboxyphenylretinamide.

The term "cytotoxics" in the course of the present invention refers to compounds that primarily trigger cell death through direct action on cell function(s) or which interfere with or inhibit cell myosis, such as alkylating agents, tumor necrosis factors, intercalating agents, microtubule inhibitors and topoisomerase inhibitors. Non-limiting examples of cytotoxics are tirapazimin, sertenef, cachectine, ifosfamide, tasonermine, lonidamine, carboplatin, altretamine, prednimustine, dibromodulcit, ranimustine, fotemustine, nedaplatin, oxaliplatin, temozolomide, heptaplatin, estramustin, improsulfantosylate, trofosfamide, nimustine, dibrospidium-chloride, pumitepa, lobaplatin, satraplatin, profiromycin, cisplatin, irofulven, dexifosfamide, cis-amindichloro(2-methylpyridine)platin, benzylguanine, glufosfamide, GPX100, (trans, trans,trans)-bis-mu-(hexane-1,6-diamine)-mu-[diamine-platin(II)]bis-[diamine(chloro)platin(II)]-tetrachloride, diarizidinyispermine, arsenium trioxide, 1-(11-Dodecylamino-10-hydroxyundecyl)-3,7-dimethylxanthine, zorubicin, idarubicin, daunorubicin, bisantren, mitoxantron, pirarubicin, pinafide, valrubicine, amrubicine, antineoplaston, 3'-desamino-3'-morpholino-13-desoxo-10-hydroxycaminomycin, annamycin, galarubicin, elinafide, MEN10755 and 4-desmethoxy-3-desamino-3-aziridinyl-4-methylsulfonyl-daunorubicin (WO 00/50032).

Non-limiting examples of microtubule inhibitors are paclitaxel, vindesine-sulfate, 3',4'-dideshydro-4'-desoxy-8'-norvincaleukoblastine, docetaxol, rhizoxine, dolastatine, mivobuline-isethionate, auristatine, cemadotine, RPR109881, BMS184476, vinflunine, cryptophycine, 2,3,4,5,6-pentafluoro-N-(3-fluoro-4-methoxyphenyl)-benzenesulfonamide, anhydrovinblastine, N,N-dimethyl-L-valyl-L-valyl-N-methyl-Lvalyl-L-prolyl-L-proline-t-butylamide, TDX258 and BMS188797.

Non-limiting examples of topoisomerase inhibitors are topotecane, hycaptamine, irinotecane, rubitecane, 6-ethoxypropionyl-3',4'-O-exo-benzylidene-chartreusine, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo-[de]-pyrano-[3',4':b,7] indolizino[1,2b]quiinoline-10,13(9H,15H)-dione, lurtotecane, 7-[2-(N-isopropylamino)ethyl]-(20S)camptothecine, BNP1350, BNPI1100, BN80915, BN80942, etoposide-phosphate, teniposide, sobuzoxane, 2'-dimethylamino-2'-desoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylendioxy)-5-methyl-7-hydroxy-8-methoxybenzo [c]phenanthridinium, 6,9-bis[(2-aminoethyl)amino]-benzo [g]isoquinoline-5,10-dione, 5-(3-aminopropylamino)-7,10-dihydroxy-2-(2-hydroxyethylaminomethyl)-6H-pyrazolo[4, 5,1-de]-acridine-6-one, N-[1-[2(diethylamino)ethylamino)]-7-methoxy-9-oxo-9H-thioxane-then-4-ylmethyl] formamide, N-(2-(dimethyl-amino)-ethyl)acridine-4-carboxamide, 6-[[2-(dimethylamino)ethyl]amino]-3-hydroxy-7H-indeno[2,1-c]quinolin-7-one and dimesna.

Non-limiting examples of antiproliferative agents are antisense RNA- and antisense-DNA oligonucleotides, such as G3139, ODN698, RVASKRAS, GEM231 and INX3001, as well as antimetabolites such as enocitabine, carmofur, tegafur, pentostatine, doxifluridine, trimetrexate, fludarabine, capecitabine, galocitabine, cytarabinocfosfate, fosteabine sodiumhydrate, raltitrexed, paltitrexide, emitefur, tiazofurine, decitabine, nolatrexed, pemetrexed, nelzarabine, 2'-desoxy-2'-methylidencytidine, 2'-fluoromethylen-2'-desoxycytidine, N-[5-(2,3-dihydrobenzofuryl)sulfonyl]-N'-(3,4-dichlorophenyl)urea, N6-[4-desoxy-4-[N2-[2(E),4(E)-tetradecadienoyl]glycylamino]-L-glycero-B-L-manno-heptopyranosyl]adenine, aplidine, ecteinascidine, troxacitabine, 4-[2-amino-4-oxo-4,6,7,8-tetrahydro-3H-pyrimidino[5,4-b][1,4]thiazine-6-yl-(S)-ethyl]-2,5-thienoyl-L-glutaminic acid, aminopterine, 5-fluorouracil, alanosine, 11-acetyl-8-(carbamoyloxymethyl)-4-formyl-6-methoxy-14-oxa-1,1'-diaza-tetracyclo-(7.4.1.0.0)-tetradeca-2,4,6-trien-9-ylacetic acid ester, swainsonine, lometrexole, dexrazoxane, methioninase, 2'-cyan-2'-desoxy-N4-palmitoyl-1-B-D-arabinofuranosylcytosine and 3-aminopyridine-2-carboxaldehyde-thiosemicarbazone.

"Antiproliferative agents" also comprises monoclonal antibodies against growth factors that have not been listed under "angiogenesis inhibitors", such as trastuzumab, as well as tumor suppressor genes, such as p53.

The pharmaceutical compositions of the present invention (as described herein) may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below:

tablets: mixing of active ingredient/s and auxiliaries, compression of said mixture into tablets (direct compression), optionally granulation of part of mixture before compression.

capsules:

mixing of active ingredient/s and auxiliaries to obtain a flowable powder, optionally granulating powder, filling powders/granulate into opened capsules, capping of capsules.

semi-solids (ointments, gels, creams): dissolving/dispersing active ingredient/s in an aqueous or fatty carrier; subsequent mixing of aqueous/fatty phase with complementary fatty/aqueous phase, homogenization (creams only).

suppositories (rectal and vaginal): dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms.

aerosols: dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more products of the invention into a dosage form suitable for administration to a patient in need of such a treatment. Usually, the transfer of one or more products of the invention into such a dosage form comprises the addition of one or more compounds, selected from the group consisting of carriers, excipients, auxiliaries and pharmaceutical active ingredients other than the products of the invention. Suitable processing steps include, but are not limited to combining, milling, mixing, granulating, dissolving, dispersing, homogenizing, casting and/or compressing the respective active and non-active ingredients. Mechanical means for performing said processing steps are known in the art, for example from Ullmann's Encyclopedia of Industrial Chemistry, 5th Edition. In this respect, active ingredients are preferably at least one product of the invention and one or more additional compounds other than the products of the invention, which show valuable pharmaceutical properties, preferably those pharmaceutical active agents other than the products of the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The products of the invention may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the products of the invention, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component me latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropylmethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The products of the invention can also be lyophilized and the lyophilizates obtained can be used, for example, for the production of injection preparations.

The preparations indicated can be sterilized and/or can contain excipients such as lubricants, preservatives, stabilizers and/or wetting agents, emulsifiers, salts for affecting the osmotic pressure, buffer substances, colorants, flavourings and/or aromatizers. They can, if desired, also contain one or more further active compounds, e.g. one or more vitamins.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the products of the present invention will be in the form of pharmaceutically acceptable salts. Other salts may, however, be useful in the preparation of the products of the invention or of their pharmaceutically acceptable salts. Suitable pharmaceutically acceptable salts of the products of the invention include acid addition salts which may, for example be formed by mixing a solution of the product of the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the products of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the products of the invention is known to the skilled artisan or can be easily determined by standard methods known in the art.

The products of the invention and the additional pharmacologically active substances are generally administered analogously to commercial preparations. Usually, suitable doses that are therapeutically effective lie in the range between 0.0005 mg and 1000 mg, preferably between 0.005 mg and 500 mg and especially between 0.5 mg and 100 mg per dose unit. The daily dose is preferably between about 0.001 mg/kg and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For the purpose of the present invention, all mammalian species are regarded as being comprised. In a preferred embodiment, such mammals are selected from the group consisting of "primate, human, rodent, equine, bovine, canine, feline, domestic animals, cattle, livestock, pets, cow, sheep, pig, goat, horse, pony, donkey, hinny, mule, hare, rabbit, cat, dog, guinea pig, hamster, rat, mouse". More preferably, such mammals are humans. Animal models are of interest for experimental investigations, providing a model for treatment of human diseases.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

In the case of many disorders, the susceptibility of a particular cell to treatment with the subject compounds may be determined by in vitro testing. Typically a culture of the cell is combined with a subject compound at varying concentrations for a period of time sufficient to allow the active agents to show a relevant reaction, usually between about one hour and one week. For in vitro testing, cultured cells from a biopsy sample may be used.

The object of the present invention has surprisingly been solved in another aspect by providing a process for manufacturing crystalline modification A1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate comprising the steps:

(a) dispersing 3-(1-{3-[5-(1-methyl-piperidin-4-yl-methoxy)-pyrimidin-2-yl]-benzyl}-6-oxo-1,6-dihydro-pyridazin-3-yl)-benzonitrile (free base) or one or more salts thereof in a solvent or a solvent mixture, preferably 2-propanole, optionally under stirring, (b) converting 3-(1-{3-[5-(1-methyl-piperidin-4-yl-methoxy)-pyrimidin-2-yl]-benzyl}-6-oxo-1,6-dihydro-pyridazin-3-yl)-benzonitrile (free base) or one or more salts thereof into the corresponding hydrochloride salt by addition of etheric hydrochloric acid solution, optionally under stirring, (c) heating up the resulting dispersion or solution of step (b) to elevated temperature T1, preferably 30° C. to 95° C., more preferably 50° C., optionally under stirring, stirring until crystallization begins and continuing stirring at room temperature until completion of the crystallization process, (d) isolating precipitated 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate by solid-liquid separation, preferably filtration, optionally subsequent washing with a solvent or a solvent mixture, preferably ether, and optionally subsequent drying, preferably in vacuo, optionally at elevated temperature T2, preferably 30° C. to 95° C., more preferably 70° C.

In the course of the present invention, the terms "elevated temperature" and "elevated temperature T or $T_x$" (with x=1, 2, 3 etc.)" refer to an individual specific temperature for a given process step or sub-step that is independent from any other "elevated temperature" and that can be any temperature within the temperature range from "above room temperature" to "boiling temperature" of a given solvent or solvent mixture and/or "melting temperature" of a given solid, educt, intermediate or product or mixture thereof, at standard pressure (approx. 1000 hPa/1000 mbar), whatever applies, whereby such any temperature should not result in decomposition of the individual process product, intermediates and/or educts.

In the course of the present invention, all general and individual specific temperatures given herein, for instance as part of the various process steps and substeps, refer to temperatures at standard pressure (approx. 1000 hPa/1000 mbar). It is well-known to the person skilled in the art that reduction or increase of pressure affects the general and individual specific temperatures given herein, i.e. a reduction of pressure will lead to lower respective temperatures whereas an increase will result in higher respective temperatures. It lies within the expert knowledge of the skilled artisan to adopt the herein disclosed process steps and substeps to lower and higher pressures, i.e. adopting the respective temperatures accordingly. Such temperature-adopted processes are within the scope and spirit of the present invention.

In the course of the present invention, the term "one or more salts of 3-(1-{3-[5-(1-methyl-piperidin-4-ylmethoxy)-pyrimidin-2-yl]-benzyl}-6-oxo-1,6-dihydro-pyridazin-3-yl) benzonitrile (free base)" refers to any and all salts, preferably pharmaceutically acceptable salts, of 3-(1-{3-[5-(1-methyl-piperidin-4-ylmethoxy)-pyrimidin-2-yl]-benzyl}-6-oxo-1,6-dihydro-pyridazin-3-yl)-benzonitrile (free base), which include, but are not limited to, acetate, adipate, alginate, arginate, aspartate, benzoate, benzolsulphonate (besylate), bisulphate, bisulphite, bromide, butyrate, bampforat, campforsulphonate, caprylate, chloride, chlorobenzoate, citrate, cyclopentanpropionate, digluconate, dihydrogenphosphate, dinitrobenzoate, dodecylsulphate, ethansulphonate, fumarate, galacterate, galacturonate, glucoheptanoate, gluconate, glutamate, glycerophosphate, hemisuccinate, hemisulphate, heptanoate, hexanoate, hippurate, hydrochloride, hydrobromide, hydroiodide, 2-hydroxyethansulphonate, iodide, isothionate, isobutyrate, lactate, lactobionate, malate, maleate, malonate, mandelate, metaphosphate, methanesulphonate, methylbenzoate, monohydrogenphosphate, 2-naphthalinsulphonate, nicotinate, nitrate, oxalate, oleate, pamoate, pectinate, persulphate, phenylacetate, 3-phenylpropionate, phosphate, phosphonate, phthalate, and toluenesulphonate.

In the course of the present invention, the term "a solvent or a solvent mixture" refers to any and all solvents, preferably organic solvents and water, more preferably pharmaceutically acceptable organic solvents and water, which include, but are not limited to, water, methanol, ethanol, 2-propanol, n-btanol, iso-butanol, acetone, methylethylketone, ethylacetate, 1,4-dioxane, diethylether, MTBE, THF, acetonitrile, dichloromethane, chloroform, DMF, cyclohexane, cyclopentane, n-hexane, n-heptane, n-pentane, toluene, o-xylene, p-xylene, DMSO, pyridine, acetic acid, anisole, butylacetate, cumene, ethylformate, formic acid, iso-butylacetate, iso-propylacetate, methylacetate, 3-methyl-1-butanol, methylisobutylketone, 2-methyl-1-propanol, 1-pentanol, propylacetate, ethylenglycole, and 1-methyl-2-pyrrolidone, as well as any and all mixtures of two or more such solvents, preferably binary mixtures, more preferably binary mixtures of water and a pharmaceutically acceptable organic solvent.

The object of the present invention has surprisingly been solved in another aspect by providing a process for manufacturing crystalline modification NF6 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate comprising the steps:

(a) dispersing 3-(1-{3-[5-(1-methyl-piperidin-4-yl-methoxy)-pyrimidin-2-yl]-benzyl}-6-oxo-1,6-dihydro-pyridazin-3-yl)-benzonitrile (free base) or one or more salts thereof in a solvent or a solvent mixture, preferably acetone, optionally under stirring, (b) converting 3-(1-{3-[5-(1-methyl-piperidin-4-yl-methoxy)-pyrimidin-2-yl]-benzyl}-6-oxo-1,6-dihydro-pyridazin-3-yl)-benzonitrile (free base) or one or more salts thereof into the corresponding hydrochloride salt by addition of aqueous hydrochloric acid solution, optionally under stirring, (c) isolating precipitated 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate by solid-liquid separation, preferably filtration, optionally subsequent washing with a solvent or a solvent mixture, and optionally subsequent drying, preferably in vacuo, optionally at elevated temperature T2, preferably 30° C. to 95° C., more preferably 65° C.

The object of the present invention has surprisingly been solved in another aspect by providing a process for manufacturing crystalline modification NF4 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate comprising the steps:

(a) spreading crystalline form NF3 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate onto a surface, preferably a bordered surface of a container, more preferably of a Petri dish, and subsequently incubating it in a drying cabinet (ambient pressure) with defined temperature, preferably 50-120% relative humidity (RH), more preferably 60-100° C., for one or more hours.

The object of the present invention has surprisingly been solved in another aspect by providing a process for manufacturing crystalline modification H1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate comprising the steps:
(a) dispersing 3-(1-{3-[5-(1-methyl-piperidin-4-ylmethoxy)-pyrimidin-2-yl]-benzyl}-6-oxo-1,6-dihydro-pyridazin-3-yl)-benzonitrile (free base) or one or more salts thereof in a solvent or a solvent mixture, preferably water, optionally under stirring,
(b) converting 3-(1-{3-[5-(1-methyl-piperidin-4-ylmethoxy)-pyrimidin-2-yl]-benzyl}-6-oxo-1,6-dihydro-pyridazin-3-yl)-benzonitrile (free base) or one or more salts thereof into the corresponding hydrochloride salt by addition of aqueous hydrochloric acid solution, optionally under stirring,
(c1) heating up the resulting dispersion of step (b) to elevated temperature T1, preferably 30° C. to 95° C., more preferably 60° C., optionally under stirring, and (i) cooling down the resulting solution, preferably to 10° C. to 40° C., more preferably to 35° C., optionally under stirring, concentrating the solution until crystallization begins and cooling it further down, preferably to 0° C. to 25° C., optionally under stirring, or (ii) solid-liquid separating, preferably filtrating it to yield a solution, incubating the solution at room temperature until crystallization begins and further incubating it at room temperature for one or more hours or days, optionally under stirring, OR
(c2) incubating the resulting dispersion of step (b) in an ultrasonic bath until a clear solution is obtained, solid-liquid separating, preferably filtrating the resulting solution and incubating it for one or more hours or days at room temperature, optionally under stirring,
(d) isolating precipitated 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate by solid-liquid separation, preferably filtration, optionally washing with a solvent or a solvent mixture, preferably water, and optionally subsequent drying, preferably in vacuo, optionally at elevated temperature T2, preferably 30° C. to 95° C., more preferably 70° C.

The object of the present invention has surprisingly been solved in another aspect by providing a process for manufacturing crystalline modification H1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate comprising the steps:
(a) dispersing 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate in a solvent or a solvent mixture, preferably water, optionally under stirring,
(b) incubating the resulting dispersion of step (a) at room temperature for one or more hours or days, optionally under stirring,
(c) isolating precipitated 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate by solid-liquid separation, preferably filtration, optionally washing with a solvent or a solvent mixture, preferably water, and optionally subsequent drying, preferably in vacuo, optionally at elevated temperature T, preferably 30° C. to 95° C., more preferably 70° C.

The object of the present invention has surprisingly been solved in another aspect by providing a process for manufacturing crystalline modification NF3 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate comprising the steps:
(a) dispersing 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate in a solvent or a solvent mixture, preferably methanol or ethanol, optionally under stirring,
(b) incubating the resulting dispersion of step (a) at elevated temperature T1, preferably 30° C. to 95° C., more preferably 40° C., for one or more hours or days, optionally under stirring, and optionally cooling it down to room temperature, optionally under stirring,
(c) isolating precipitated 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate by solid-liquid separation, preferably filtration, optionally washing with a solvent or a solvent mixture, preferably ethanol, and optionally subsequent drying, preferably in vacuo, optionally at elevated temperature T2, preferably 30° C. to 95° C., more preferably 70° C.

The object of the present invention has surprisingly been solved in another aspect by providing a process for manufacturing crystalline modification NF3 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate comprising the steps:
(a) dispersing 3-(1-{3-[5-(1-methyl-piperidin-4-ylmethoxy)-pyrimidin-2-yl]-benzyl}-6-oxo-1,6-dihydro-pyridazin-3-yl)-benzonitrile (free base) or one or more salts thereof in a solvent or a solvent mixture, preferably water, optionally under stirring,
(b) converting 3-(1-{3-[5-(1-methyl-piperidin-4-ylmethoxy)-pyrimidin-2-yl]-benzyl}-6-oxo-1,6-dihydro-pyridazin-3-yl)-benzonitrile (free base) or one or more salts thereof into the corresponding hydrochloride salt by addition of aqueous hydrochloric acid solution, optionally under stirring,
(c) heating up the resulting dispersion of step (b) to elevated temperature T1, preferably 30° C. to 95° C., more preferably 60° C., optionally under stirring, optionally solid-liquid separating, preferably filtrating it to yield a solution, incubating the solution at room temperature until crystallization begins and further incubating it at room temperature for one or more hours or days, optionally under stirring,
(d) isolating precipitated 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate by solid-liquid separation, preferably filtration, optionally washing with a solvent or a solvent mixture, preferably water, and optionally subsequent drying, preferably in vacuo, optionally at elevated temperature T2, preferably 30° C. to 95' C, more preferably 70° C.
(e) dispersing the resulting dried crystals of step (d) in a solvent or a solvent mixture, preferably methanol or ethanol, and incubating the resulting dispersion at room temperature for one or more hours or days, optionally under stirring,
(f) isolating precipitated 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate by solid-liquid separation, preferably filtration, optionally washing with a solvent or a solvent mixture, preferably ethanol, and optionally subsequent drying, preferably in vacuo, optionally at elevated temperature T3, preferably 30° C. to 95° C., more preferably 70° C.

The object of the present invention has surprisingly been solved in another aspect by providing a process for manufacturing crystalline modification NF2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate comprising the steps:
(a) dispersing 3-(1-{3-[5-(1-methyl-piperidin-4-ylmethoxy)-pyrimidin-2-yl]-benzyl}-6-oxo-1,6-dihydro-pyridazin-3-yl)-benzonitrile (free base) or one or more salts thereof in a solvent or a solvent mixture, preferably water, optionally under stirring,
(b) converting 3-(1-{3-[5-(1-methyl-piperidin-4-ylmethoxy)-pyrimidin-2-yl]-benzyl}-6-oxo-1,6-dihydro-pyridazin-3-yl)-benzonitrile (free base) or one or more salts thereof into the corresponding hydrochloride salt by addition of hydrochloric acid solution, optionally under stirring,
(c) heating up the resulting dispersion or solution of step (b) to elevated temperature T1, preferably 30° C. to 95° C., more preferably 60° C., optionally under stirring,
(d) cooling the resulting solution or dispersion down to 20-40° C., preferably 35° C.,
(e) removing solvent via evaporation, preferably in a rotary evaporator, optional under vacuum, until crystallization sets in,
(f) isolating precipitated 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate by solid-liquid separation, preferably filtration, optionally subsequent washing with a solvent, preferably water, without further drying.

The object of the present invention has surprisingly been solved in another aspect by providing a process for manufacturing crystalline modification NF2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate comprising the steps:
(a) spreading 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate crystalline modification A1 onto a surface, preferably a bordered surface of a container, more preferably of a Petri dish, and subsequently incubating it in a sealed desiccator over water or aqueous salt solutions with defined relative humidity (RH), preferably 80-100% RH, more preferably 94-100% RH, for one or more days or weeks.

The object of the present invention has surprisingly been solved in another aspect by providing a process for manufacturing crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate comprising the steps:
(a) dispersing 3-(1-{3-[5-(1-methyl-piperidin-4-ylmethoxy)-pyrimidin-2-yl]-benzyl}-6-oxo-1,6-dihydro-pyridazin-3-yl)-benzonitrile (free base) or one or more salts thereof in a solvent or a solvent mixture, preferably acetone, optionally under stirring, and optionally heating up the resulting dispersion to elevated temperature T1, preferably 30° C. to 95° C., more preferably 60° C., optionally under stirring,
(b) converting 3-(1-{3-[5-(1-methyl-piperidin-4-ylmethoxy)-pyrimidin-2-yl]-benzyl}-6-oxo-1,6-dihydro-pyridazin-3-yl)-benzonitrile (free base) or one or more salts thereof into the corresponding hydrochloride salt by addition of aqueous hydrochloric acid solution, optionally under stirring, optionally heating up the resulting dispersion to elevated temperature T2, preferably 30° C. to 95° C., more preferably 60° C., for one or more minutes or hours, preferably 30 min, optionally under stirring, and optionally adding further solvent or solvent mixture, preferably water, optionally under stirring,
(c) cooling down the dispersion of step (b) to room temperature, optionally under stirring, and incubating it at room temperature for one or more hours or days, optionally under stirring,
(d) isolating precipitated 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate by solid-liquid separation, preferably filtration, optionally washing with a solvent or a solvent mixture, preferably acetone or THF, and optionally subsequent drying, preferably in vacuo, optionally at elevated temperature T3, preferably 30° C. to 95° C., more preferably 50° C.

The object of the present invention has surprisingly been solved in another aspect by providing a process for manufacturing crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate comprising the steps:
(a) dispersing 3-(1-{3-[5-(1-methyl-piperidin-4-ylmethoxy)-pyrimidin-2-yl]-benzyl}-6-oxo-1,6-dihydro-pyridazin-3-yl)-benzonitrile (free base) or one or more salts thereof in a solvent or a solvent mixture, preferably water, optionally under stirring,
(b) converting 3-(1-{3-[5-(1-methyl-piperidin-4-ylmethoxy)-pyrimidin-2-yl]-benzyl}-6-oxo-1,6-dihydro-pyridazin-3-yl)-benzonitrile (free base) or one or more salts thereof into the corresponding hydrochloride salt by addition of aqueous hydrochloric acid solution, optionally under stirring, heating up the resulting dispersion to elevated temperature T1, preferably 30° C. to 100° C., more preferably 80° C. to 100° C., optionally under stirring, and optionally solid-liquid separating, preferably filtrating it to obtain a solution,
(c) heating up again the resulting filtrate of step (b) to elevated temperature T2, preferably 30° C. to 100° C., more preferably 78° C. to 85° C., optionally under stirring, and subsequently cooling it down, preferably to 0° C. to 40° C., more preferably to 0° C. to 27° C., over one or more hours or days, optionally under stirring, and optionally cooling it further down, preferably to 0° C. to 25° C., more preferably to 20° C., optionally under stirring,
(d) isolating precipitated 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate by solid-liquid separation, preferably filtration, optionally washing with a solvent or a solvent mixture, preferably water, THF or acetone, and optionally subsequent drying, preferably in vacuo, optionally at elevated temperature T3, preferably 30° C. to 95° C., more preferably 50° C. to 55° C.

In a preferred embodiment, a process for manufacturing crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate according to above aspects and embodiments is provided, wherein in step (b) 3-(1-{3-[5-(1-methyl-piperidin-4-ylmethoxy)-pyrimidin-2-yl]-benzyl}-6-oxo-1,6-dihydro-pyridazin-3-yl)-benzonitrile (free base) or one or more salts thereof is converted into the corresponding hydrochloride salt by addition of one or more chloride salts selected from the group consisting of: "alkaline metal chloride salt, such as NaCl, KCl and LiCl; alkaline earth metal chloride salt, such as $CaCl_2$ and $MgCl_2$; ammonium chloride salt ($NH_4Cl$), quaternary organic ammonia chloride salt, such as ethanolammonium chloride and diethylammonium chloride; transition metal chloride salt, such as $FeCl_2$ and $CuCl_2$".

The object of the present invention has surprisingly been solved in another aspect by providing a process for manufacturing crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate comprising the steps:
  (a) re-crystallizing 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate from a solvent or a solvent mixture, optionally under stirring.

The processes for manufacturing the crystalline modifications of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate, hydrate and monohydrate, in particular for crystalline modification H2 of 3-(1-{3-[5-(1-methyl-piperidin-4-ylmethoxy)-pyrimidin-2-yl]benzyl}-6-oxo-1,6-dihydro-pyridazin-3-yl)-benzonitrile hydrochloride monohydrate, are surprisingly characterized by a superior product quality due to crystallization from aqueous solvents or aqueous solvent mixtures, preferably water. Further, these processes are surprisingly characterized by superior yields as well as increased product stability. In particular, crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate represents the thermodynamically most stable crystalline modification that does not convert itself into less stable crystalline modifications during storage as pharmaceutical formulation.

Figure 1:
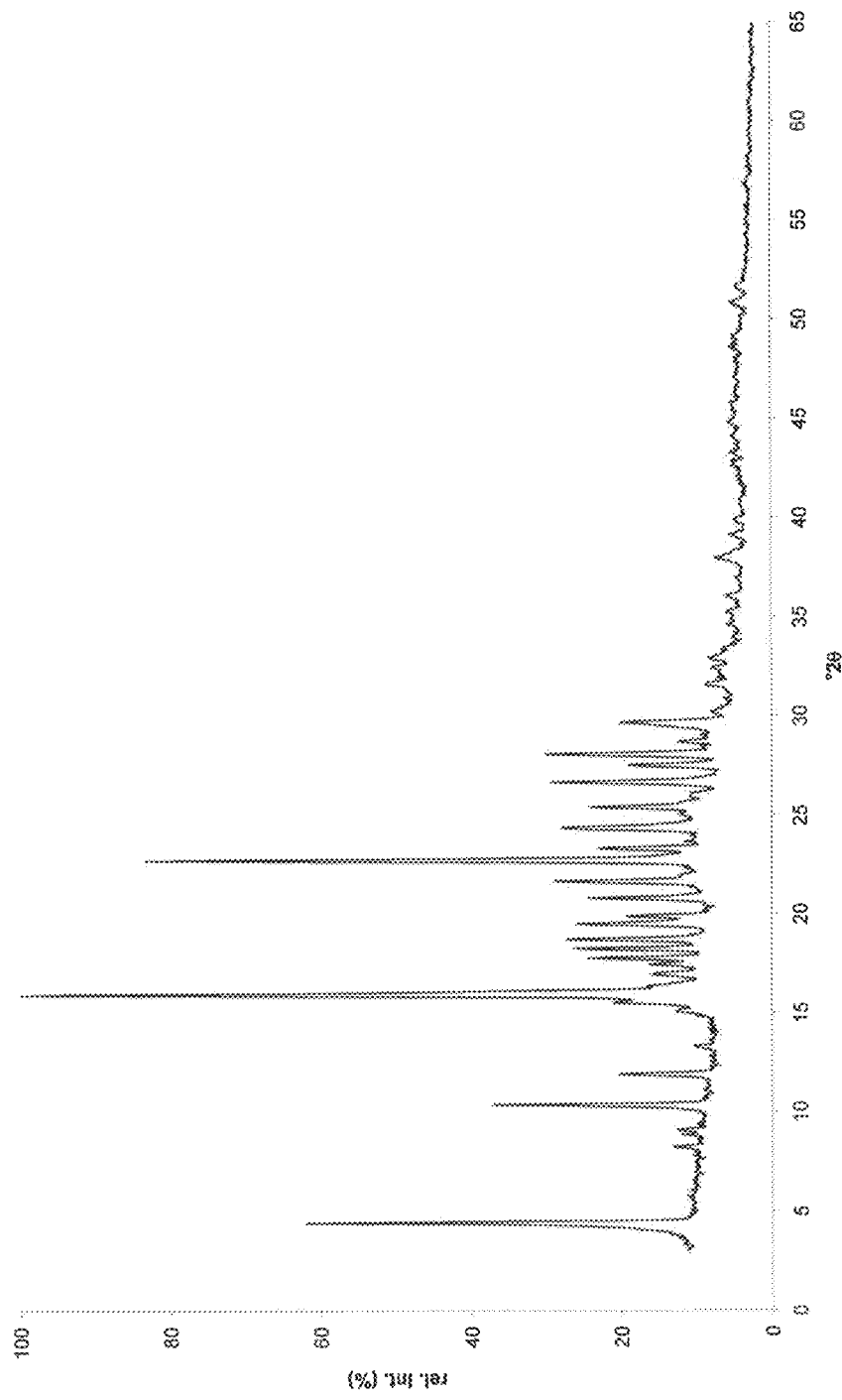
FIG. 1 depicts the powder X-ray diffractogram of crystalline modification A1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate.

Even without further details, it is assumed that a person skilled in the art will be able to utilise the above description in the broadest scope. The preferred embodiments should therefore merely be regarded as descriptive disclosure, which is absolutely not limiting in any way.

The contents of all cited references are hereby incorporated by reference in their entirety. The invention is explained in more detail by means of the following examples without, however, being restricted thereto.

EXAMPLES

Example 1

Production of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate in its crystalline modification A1

Method 1

Approx. 200 mg of 3-(1-{3-[5-(1-Methyl-piperidin-4-ylmethoxy)-pyrimidin-2-yl]-benzyl}-6-oxo-1,6-dihydro-pyridazin-3-yl)-benzonitrile (free base) were dispersed in 5 mL warm 2-propanole. After addition of approx. 0.1 mL etheric HCl solution (10%), a clear solution was formed, which was further agitated at 50° C. until crystallisation set in. Agitation was continued at room temperature until completion of the crystallisation process. The obtained crystals were filtered and washed with ether.

$^1$H-NMR (d$_6$-DMSO): δ [ppm]=1.60 (m, 2H), 2.00 (m, 2H), 2.07 (m, 1H), 2.75 (d, 3H), 2.97 (m, 2H), 3.45 (m, 2H), 4.10 (d, 2H), 5.45 (s, 2H), 7.16 (d, 1H), 7.50 (bm, 2H), 7.73 (t, 1H), 7.93 (m, 1H), 8.18 (d, 1H), 8.25 (bm, 2H), 8.38 (m, 2H), 8.67 (s, 2H), 9.90 (bs, 1H).

Ion Chromatography: 6.4 wt % Cl (equivalent to molar acid:base ratio of 0.96)

Method 2

Approx. 2 g of 3-(1-{3-[5-(1-Methyl-piperidin-4-ylmethoxy)-pyrimidin-2-yl]-benzyl}-6-oxo-1,6-dihydro-pyridazin-3-yl)-benzonitrile (free base) were dispersed in 5 mL warm 2-propanole. After addition of approx. 2 mL etheric HCl solution (10%), a clear solution was formed, which was further agitated at 50° C. until crystallisation set in. Agitation was continued at room temperature until completion of the crystallisation process. The obtained crystals were filtered and washed with ether.

$^1$H-NMR (de-DMSO): δ [ppm]=1.60 (m, 2H), 2.00 (m, 2H), 2.07 (m, 1H), 2.75 (d, 3H), 2.97 (m, 2H), 3.45 (m, 2H), 4.10 (d, 2H), 5.45 (s, 2H), 7.15 (d, 1H), 7.50 (bm, 2H), 7.72 (t, 1H), 7.93 (m, 1H), 8.18 (d, 1H), 8.24 (bm, 2H), 8.39 (m, 2H), 8.66 (s, 2H), 10.05 (bs, 1H).

Ion Chromatography: 5.9 wt % Cl (equivalent to molar acid:base ratio of 0.88 based on the anhydrous HCl salt)

Example 2

Production of 3-(1-{3-[5-(1-methyl-piperidin-4-yl-methoxy)-pyrimidin-2-yl]-benzyl}-6-oxo-1,6-dihydro-pyridazin-3-yl)-benzonitrile hydrochloride hydrate in its crystalline modification H1

Method 1

Approx. 44.75 g of 3-(1-{3-[5-(1-Methyl-piperidin-4-yl-methoxy)-pyrimidin-2-yl]-benzyl}-6-oxo-1,6-dihydro-pyridazin-3-yl)-benzonitrile (free base) were dispersed in 430 mL DI water, and approx. 105 mL 1 N aqueous HCl solution was added. The dispersion was heated to 60° C., resulting in an opaque solution. The solution was cooled down to 35° C. and concentrated in a rotary evaporator (w/o vacuum) until crystallisation was observed. The dispersion was cooled in ice water, and finally filtered. Crystals were dried under vacuum at 70° C.

$^1$H-NMR (d6-DMSO): δ [ppm]=1.59 (m, 2H), 1.99 (m, 2H), 2.06 (m, 1H), 2.73 (s, 3H), 2.97 (m, 2H), 3.43 (m, 2H), 4.10 (d, 2H), 5.45 (s, 2H), 7.18 (d, 1H), 7.50 (bm, 2H), 7.71 (t, 1H), 7.93 (m, 1H), 8.18 (d, 1H), 8.23 (bm, 2H), 8.38 (m, 2H), 8.66 (s, 2H), 9.98 (bs, 1H).

Ion Chromatography: 6.4 wt % Cl (equivalent to molar acid:base ratio of 1.01 based on HCl salt with observed water content as specified below).

Karl-Fischer-Titration: 5.2 wt % water.

Method 2

Approx. 5.12 g of 3-(1-{3-[5-(1-Methyl-piperidin-4-yl-methoxy)-pyrimidin-2-yl]-benzyl}-6-oxo-1,6-dihydro-pyridazin-3-yl)-benzonitrile (free base) were dispersed in approx. 44 mL DI water and approx. 11 mL 1 N aqueous HCl solution. The dispersion was put in an ultrasonic bath until a clear solution was obtained, and filtered thereafter. The clear solution was agitated overnight at room temperature. The resulting crystals were filtered, and dried.

$^1$H-NMR (d$_6$-DMSO): δ [ppm]=1.61 (m, 2H), 1.99 (m, 2H), 2.06 (m, 1H), 2.74 (s, 3H), 2.95 (m, 2H), 3.45 (m, 2H), 4.10 (d, 2H), 5.45 (s, 2H), 7.17 (d, 1H), 7.50 (bm, 2H), 7.72 (t, 1H), 7.93 (m, 1H), 8.18 (d, 1H), 8.23 (bm, 2H), 8.37 (m, 2H), 8.65 (s, 2H), 10.05 (bs, 1H).

Ion Chromatography: 6.0 wt % Cl (equivalent to molar acid:base ratio of 0.97 based on HCl salt with observed water content as specified below).

Karl-Fischer-Titration: 7.9 wt % water.

Method 3

Approx. 495 mg of 3-(1-{3-[5-(1-methyl-piperidin-4-yl-methoxy)-pyrimidin-2-yl]-benzyl}-6-oxo-1,6-dihydro-pyridazin-3-yl)-benzonitrile (free base) were dispersed in approx. 3.9 mL DI water and approx. 1.1 mL 1 N aqueous HCl solution. The dispersion was heated and the warm (40-80° C.) dispersion filtered to yield a clear solution. The clear solution was left at room temperature until crystallisation started after approx. 4 hours. The resulting dispersion was filtered. Crystals were washed with DI water, and dried under vacuum.

$^1$H-NMR (d$_6$-DMSO): δ [ppm]=1.58 (m, 2H), 1.98 (m, 2H), 2.05 (m, 1H), 2.74 (s, 3H), 2.94 (m, 2H), 3.45 (m, 2H), 4.10 (d, 2H), 5.44 (s, 2H), 7.16 (d, 1H), 7.50 (bm, 2H), 7.72 (t, 1H), 7.93 (m, 1H), 8.18 (d, 1H), 8.25 (bm, 2H), 8.37 (m, 2H), 8.65 (s, 2H), 9.78 (bs, 1H).

Ion Chromatography: 6.0 wt % Cl (equivalent to molar acid:base ratio of 0.95 based on HCl salt with observed water content as specified below).

Karl-Fischer-Titration: 6.2 wt % water.

Method 4

Approx. 985 mg of 3-(1-{3-[5-(1-methyl-piperidin-4-yl-methoxy)-pyrimidin-2-yl]-benzyl}-6-oxo-1,6-dihydro-pyridazin-3-yl)-benzonitrile (free base) were dispersed in approx. 8 mL DI water and approx. 2.1 mL 1 N aqueous HCl solution. The dispersion was heated and the warm dispersion filtered to yield a clear solution. The clear solution was left at room temperature until crystallisation set in. After leaving the experiment over night, the resulting dispersion was filtered. Crystals were washed with DI water, and dried under vacuum.

$^1$H-NMR (de-DMSO): δ [ppm]=1.57 (m, 2H), 1.98 (m, 2H), 2.05 (m, 1H), 2.74 (s, 3H), 2.95 (m, 2H), 3.43 (m, 2H), 4.09 (d, 2H), 5.44 (s, 2H), 7.16 (d, 1H), 7.50 (bm, 2H), 7.73 (t, 1H), 7.93 (m, 1H), 8.17 (d, 1H), 8.24 (bm, 2H), 8.37 (m, 2H), 8.65 (s, 2H), 9.77 (bs, 1H).

Ion Chromatography: 6.0 wt % Cl (equivalent to molar acid:base ratio of 0.97 based on HCl salt with observed water content as specified below).

Karl-Fischer-Titration: 7.9 wt % water.

Method 5

Approx. 700 mg of 3-(1-{3-[5-(1-Methyl-piperidin-4-yl-methoxy)-pyrimidin-2-yl]-benzyl}-6-oxo-1,6-dihydro-pyridazin-3-yl)-benzonitrile hydrochloride hydrate crystalline modification H1 were dispersed in approx. 7 mL DI water agitated over several days at room temperature. The resulting dispersion was filtered. Crystals were washed with DI water, and dried under vacuum.

$^1$H-NMR (de-DMSO): δ [ppm]=1.57 (m, 2H), 1.98 (m, 2H), 2.05 (m, 1H), 2.74 (s, 3H), 2.94 (m, 2H), 3.43 (m, 2H), 4.10 (d, 2H), 5.44 (s, 2H), 7.17 (d, 1H), 7.49 (bm, 2H), 7.73 (t, 1H), 7.93 (m, 1H), 8.18 (d, 1H), 8.24 (bm, 2H), 8.37 (m, 2H), 8.66 (s, 2H), 9.68 (bs, 1H).

Ion Chromatography: 5.7 wt % Cl (equivalent to molar acid:base ratio of 0.90 based on HCl salt with observed water content as specified below).

Karl-Fischer-Titration: 6.1 wt % water.

Example 3

Production of 3-(1-{3-[5-(1-methyl-piperidin-4-yl-methoxy)-pyrimidin-2-yl]-benzyl}-6-oxo-1,6-dihydro-pyridazin-3-yl)-benzonitrile hydrochloride hydrate in its crystalline modification NF3

Method 1

Approx. 1.1 g of 3-(1-{3-[5-(1-Methyl-piperidin-4-yl-methoxy)-pyrimidin-2-yl]-benzyl}-6-oxo-1,6-dihydro-pyridazin-3-yl)-benzonitrile hydrochloride hydrate crystalline modification H1 were dispersed in approx. 20 mL ethanol and agitated as slurry at 40 C for several days. The dispersion was then filtered and resulting crystals washed with ethanol and dried under vacuum.

$^1$H-NMR (de-DMSO): δ [ppm]=1.65 (m, 2H), 1.98 (m, 2H), 2.06 (m, 1H), 2.73 (s, 3H), 2.98 (m, 2H), 3.44 (m, 2H), 4.10 (d, 2H), 5.44 (s, 2H), 7.16 (d, 1H), 7.49 (bm, 2H), 7.72 (t, 1H), 7.94 (m, 1H), 8.18 (d, 1H), 8.24 (bm, 2H), 8.38 (m, 2H), 8.65 (s, 2H), 10.52 (bs, 1H).

Ion Chromatography: 6.0 wt % Cl (equivalent to molar acid:base ratio of 0.96 based on HCl salt with observed water content as specified below).

Karl-Fischer-Titration: 6.6 wt % water.

Method 2

Approx. 495 mg of 3-(1-{3-[5-(1-Methyl-piperidin-4-yl-methoxy)-pyrimidin-2-yl]-benzyl}-6-oxo-1,6-dihydro-pyridazin-3-yl)-benzonitrile (free base) were dispersed in approx. 3.9 mL DI water and approx. 1.1 mL 1 N aqueous HCl solution. The dispersion was heated and the warm dispersion filtered to yield a clear solution. The clear solution was left at room temperature until crystallisation set in. After approx. 4 hours, the resulting dispersion was filtered. Crystals were washed with DI water, and dried under vacuum. Approx 346 mg of the dried crystals were dispersed in approx. 3 mL ethanol and agitated as slurry at room temperature for several days. The dispersion was then filtered and resulting crystals washed with ethanol and dried under vacuum.

$^1$H-NMR (de-DMSO): δ [ppm]=1.58 (m, 2H), 1.99 (m, 2H), 2.06 (m, 1H), 2.73 (s, 3H), 2.96 (m, 2H), 3.43 (m, 2H), 4.10 (d, 2H), 5.45 (s, 2H), 7.17 (d, 1H), 7.49 (bm, 2H), 7.72 (t, 1H), 7.93 (m, 1H), 8.18 (d, 1H), 8.24 (bm, 2H), 8.39 (m, 2H), 8.67 (s, 2H), 9.80 (bs, 1H).

Ion Chromatography: 5.7 wt % Cl (equivalent to molar acid:base ratio of 0.92 based on HCl salt with observed water content as specified below).

Karl-Fischer-Titration: 7.9 wt % water.

Method 3

Approx. 100 mg of 3-(1-{3-[5-(1-Methyl-piperidin-4-yl-methoxy)-pyrimidin-2-yl]-benzyl}-6-oxo-1,6-dihydro-pyridazin-3-yl)-benzonitrile hydrochloride monohydrate crystalline modification H2 were dispersed in approx. 0.6 mL methanol and shaken as slurry at room temperature at 1000 rpm for 1 day. The dispersion was then filtered and resulting crystals were dried at ambient conditions on the filter.

$^1$H-NMR (de-DMSO): δ [ppm]=1.58 (m, 2H), 2.00 (m, 2H), 2.06 (m, 1H), 2.75 (s, 3H), 2.98 (m, 2H), 3.46 (m, 2H), 4.10 (d, 2H), 5.46 (s, 2H), 7.16 (d, 1H), 7.49 (bm, 2H), 7.73 (t, 1H), 7.94 (m, 1H), 8.18 (d, 1H), 8.24 (bm, 2H), 8.39 (m, 2H), 8.66 (s, 2H), 9.77 (bs, 1H).

Ion Chromatography: 5.6 wt % Cl (equivalent to molar acid:base ratio of 0.92 based on HCl salt with observed water content as specified below).

Karl-Fischer-Titration: 9.6 wt % water.

Method 4

Approx. 1.1 g of 3-(1-{3-[5-(1-Methyl-piperidin-4-yl-methoxy)-pyrimidin-2-yl]-benzyl}-6-oxo-1,6-dihydro-pyridazin-3-yl)-benzonitrile hydrochloride hydrate crystalline modification H1 were dispersed in approx. 20 mL ethanol and agitated as slurry at 40 C for 1 day. The dispersion was then cooled to room temperature and filtered. Resulting crystals were washed with ethanol and dried under vacuum.

$^1$H-NMR (de-DMSO): δ [ppm]=1.57 (m, 2H), 1.98 (m, 2H), 2.05 (m, 1H), 2.74 (s, 3H), 2.95 (m, 2H), 3.44 (m, 2H), 4.10 (d, 2H), 5.45 (s, 2H), 7.15 (d, 1H), 7.48 (bm, 2H), 7.73 (t, 1H), 7.93 (m, 1H), 8.17 (d, 1H), 8.23 (bm, 2H), 8.37 (m, 2H), 8.65 (s, 2H), 9.70 (bs, 1H).

Ion Chromatography: 5.3 wt % Cl (equivalent to molar acid:base ratio of 0.81 based on HCl salt with observed water content as specified below).

Karl-Fischer-Titration: 2.0 wt % water.

Example 4

Production of 3-(1-{3-[5-(1-methyl-piperidin-4-yl-methoxy)-pyrimidin-2-yl]-benzyl}-6-oxo-1,6-dihydro-pyridazin-3-yl)-benzonitrile hydrochloride monohydrate in its crystalline modification H2

Method 1

Approx. 636 mg of 3-(1-{3-[5-(1-methyl-piperidin-4-yl-methoxy)-pyrimidin-2-yl]-benzyl}-6-oxo-1,6-dihydro-pyridazin-3-yl)-benzonitrile (free base) were dispersed in approx. 7 mL acetone and heated. Approx. 1.4 mL 1 N aqueous HCl solution were added, resulting in a clear solution with subsequent crystallisation setting in. The resulting dispersion was agitated at room temperature for 16 hours, and subsequently filtered. The resulting crystals were dried under vacuum at 70° C.

$^1$H-NMR (de-DMSO): δ [ppm]=1.60 (m, 2H), 1.98 (m, 2H), 2.07 (m, 1H), 2.74 (s, 3H), 2.95 (m, 2H), 3.44 (m, 2H), 4.10 (s, 2H), 5.45 (s, 2H), 7.15 (d, 1H), 7.48 (bm, 2H), 7.72 (t, 1H), 7.93 (m, 1H), 8.18 (d, 1H), 8.24 (bm, 2H), 8.38 (m, 2H), 8.65 (s, 2H), 9.82 (bs, 1H).

Ion Chromatography: 5.9 wt % Cl (equivalent to molar acid:base ratio of 0.93 based on HCl salt with observed water content as specified below).

Karl-Fischer-Titration: 5.5 wt % water.

Method 2

Approx. 106 g of 3-(1-{3-[5-(1-methyl-piperidin-4-yl-methoxy)-pyrimidin-2-yl]-benzyl}-6-oxo-1,6-dihydro-pyridazin-3-yl)-benzonitrile (free base) were dispersed in approx. 1.1 L acetone and approx. 237 mL 1 N aqueous HCl. The dispersion was heated to 60° C. for 0.5 h, with further addition of approx. 18.5 mL DI water. The dispersion was then cooled to room temperature and agitated over night at room temperature. The dispersion was then filtered, and resulting crystals washed with acetone and dried under vacuum.

$^1$H-NMR (de-DMSO): δ [ppm]=1.65 (m, 2H), 1.98 (m, 2H), 2.07 (m, 1H), 2.73 (s, 3H), 2.96 (m, 2H), 3.44 (m, 2H), 4.10 (d, 2H), 5.45 (s, 2H), 7.16 (d, 1H), 7.49 (bm, 2H), 7.72 (t, 1H), 7.93 (m, 1H), 8.17 (d, 1H), 8.24 (bm, 2H), 8.38 (m, 2H), 8.65 (s, 2H), 10.30 (bs, 1H).

Ion Chromatography: 6.7 wt % Cl (equivalent to molar acid:base ratio of 1.04 based on HCl salt with observed water content as specified below).

Karl-Fischer-Titration: 3.7 wt % water.

Method 3

Approx. 1.04 kg of 3-(1-{3-[5-(1-methyl-piperidin-4-yl-methoxy)-pyrimidin-2-yl]-benzyl}-6-oxo-1,6-dihydro-pyridazin-3-yl)-benzonitrile (free base) were dispersed in approx. 9 L DI water and approx. 2.27 L 1 N aqueous HCl. The dispersion was heated to 80° C., with subsequent warm filtration to yield a clear solution. The filtrate was heated to 78° C., and slowly cooled over night down to 27° C. The resulting dispersion was further cooled down to 20° C., and filtered. The resulting crystals were dried under vacuum at 55° C.

$^1$H-NMR (de-DMSO): δ [ppm]=1.62 (m, 2H), 1.99 (m, 2H), 2.08 (m, 1H), 2.75 (s, 3H), 2.98 (m, 2H), 3.43 (m, 2H+H2O), 4.12 (s, 2H), 5.45 (s, 2H), 7.15 (d, 1H), 7.50 (bm, 2H), 7.73 (t, 1H), 7.93 (m, 1H), 8.17 (d, 1H), 8.24 (bm, 2H), 8.38 (m, 2H), 8.65 (s, 2H), 9.98 (bs, 1H).

Ion Chromatography: 5.7 wt % Cl (equivalent to molar acid:base ratio of 0.91 based on HCl salt with observed water content as specified below).

Karl-Fischer-Titration: 6.3 wt % water.

Method 4

Approx. 7.5 g of 3-(1-{3-[5-(1-methyl-piperidin-4-yl-methoxy)-pyrimidin-2-yl]-benzyl}-6-oxo-1,6-dihydro-pyridazin-3-yl)-benzonitrile (free base) were dispersed in approx. 65.5 g DI water and approx. 2.25 g aqueous HCl solution (25%). The dispersion was heated to 90° C., with subsequent warm filtration to yield a clear solution. The filtrate was heated to 85° C., and slowly cooled down to 20° C. at 0.1 K/min. The resulting dispersion was filtered at room temperature. The resulting crystals were washed with DI water and acetone and dried under vacuum at 50° C.

$^1$H-NMR (d$_6$-DMSO): δ [ppm]=1.58 (m, 2H), 1.98 (m, 2H), 2.06 (m, 1H), 2.74 (s, 3H), 2.95 (m, 2H), 3.44 (m, 2H), 4.10 (d, 2H), 5.45 (s, 2H), 7.16 (d, 1H), 7.49 (bm, 2H), 7.72 (t, 1H), 7.93 (m, 1H), 8.18 (d, 1H), 8.25 (bm, 2H), 8.38 (m, 2H), 8.65 (s, 2H), 9.74 (bs, 1H).

Ion Chromatography: 5.7 wt % Cl (equivalent to molar acid:base ratio of 1.03 based on HCl salt with observed water content as specified below).

Karl-Fischer-Titration: 5.7 wt % water.

Example 5

Production of 3-(1-{3-[5-(1-methyl-piperidin-4-yl-methoxy)-pyrimidin-2-yl]-benzyl}-6-oxo-1,6-dihydro-pyridazin-3-yl)-benzonitrile hydrochloride anhydrate in its crystalline modification NF6

Method 1

Approx. 511 mg of 3-(1-{3-[5-(1-Methyl-piperidin-4-yl-methoxy)-pyrimidin-2-yl]-benzyl}-6-oxo-1,6-dihydro-pyridazin-3-yl)-benzonitrile (free base) were dispersed in approx. 75 mL acetone. After addition of approx. 1.1 mL aqueous hydrochloric acid solution, precipitation occurred. The dispersion was then filtered and resulting crystals were dried at under vacuum at 65° C.

$^1$H NMR (500 MHz, DMSO) δ=10.28 (s br, 1H), 8.64 (s, 2H), 8.44-8.31 (m, 2H), 8.29-8.20 (m, 2H), 8.17 (d, J=9.8, 1H), 7.93 (d, J=7.8, 1H), 7.72 (t, J=7.9, 1H), 7.53-7.43 (m, 2H), 7.16 (d, J=9.7, 1H), 5.45 (s, 2H), 4.35-3.86 (m, 2H), 3.62-3.36 (m, 2H), 3.10-2.86 (m, 2H), 2.71 (s, 3H), 2.20-2.02 (m, 1H), 2.01-1.91 (m, 2H), 1.76-1.49 (m, 2H).

Ion Chromatography: 6.6 wt % Cl (equivalent to molar acid:base ratio of 0.98)

Karl-Fischer-Titration: 0.8 wt % water.

Example 6

Production of 3-(1-{3-[5-(1-methyl-piperidin-4-yl-methoxy)-pyrimidin-2-yl]-benzyl}-6-oxo-1,6-dihydro-pyridazin-3-yl)-benzonitrile hydrochloride anhydrate in its crystalline modification NF4

Method 1

Approx. 20 mg of 3-(1-{3-[5-(1-Methyl-piperidin-4-yl-methoxy)-pyrimidin-2-yl]-benzyl}-6-oxo-1,6-dihydro-pyridazin-3-yl)-benzonitrile hydrochloride hydrate, crystalline modification NF3, were placed in a temperature chamber of an Powder X-Ray Diffraction (PXRD) instrument. The sample was heated from 30° C. to 60° C. in increments of 10° C., with approx. dwell times of 30 minutes at each temperature.

Method 2

Approx. 20 mg of 3-(1-{3-[5-(1-Methyl-piperidin-4-yl-methoxy)-pyrimidin-2-yl]-benzyl}-6-oxo-1,6-dihydro-pyridazin-3-yl)-benzonitrile hydrochloride hydrate, crystalline modification NF3, were spread on a petri dish, and placed in a drying cabinet at 60° C. (ambient pressure) for 4 hours.

Example 7

Production of 3-(1-{3-[5-(1-methyl-piperidin-4-yl-methoxy)-pyrimidin-2-yl]-benzyl}-6-oxo-1,6-dihydro-pyridazin-3-yl)-benzonitrile hydrochloride hydrate in its crystalline modification NF2

Method 1

Approx. 44.8 g of 3-(1-{3-[5-(1-Methyl-piperidin-4-yl-methoxy)-pyrimidin-2-yl]-benzyl}-6-oxo-1,6-dihydro-pyridazin-3-yl)-benzonitrile (free base) were dispersed in approx. 440 mL water. After addition of 5 mL aqueous hydrochloric acid (1 N) and further 90 mL water, the resulting dispersion was heated to 60° C. The resulting solution was cooled to 35° C. Solvent was evaporated in a rotary evaporator at ambient pressure until crystallisation set-in. The resulting dispersion was then cooled in an ice-batch and filtered, without further drying procedures.

Method 2

Approx. 50 mg of 3-(1-{3-[5-(1-Methyl-piperidin-4-yl-methoxy)-pyrimidin-2-yl]-benzyl}-6-oxo-1,6-dihydro-pyridazin-3-yl)-benzonitrile hydrochloride anhydrate in its crystalline modification A1 were spread onto a Petri dish and stored in a closed desiccator over pure DI water (100% relative humidity atmosphere) for 3 weeks.

Example 8

Structural and physico-chemical characterization of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate in its crystalline modification A1

A Powder X-Ray Diffraction pattern of crystalline modification A1 was obtained by standard techniques as described in the European Pharmacopeia 6$^{th}$ Edition chapter 2.9.33, and is characterized by the following X-ray powder diffractogram (Cu—Kα$_1$ radiation, λ=1.5406 Å, Stoe StadiP 611 KL diffractometer) depicted in FIG. 1.

Crystalline modification A1 is characterized by the following XRD data:

| | Powder X-ray diffractogram peak list: | |
|---|---|---|
| Peak No. | d/Å | °2θ (Cu-Kα$_1$ radiation) ±0.1° |
| 1 | 20.08 | 4.4 |
| 2 | 8.55 | 10.3 |
| 3 | 7.43 | 11.9 |
| 4 | 5.70 | 15.5 |
| 5 | 5.56 | 15.9 |
| 6 | 4.99 | 17.8 |
| 7 | 4.86 | 18.2 |
| 8 | 4.74 | 18.7 |
| 9 | 4.55 | 19.5 |
| 10 | 4.46 | 19.9 |
| 11 | 4.27 | 20.8 |
| 12 | 4.10 | 21.6 |
| 13 | 3.91 | 22.7 |
| 14 | 3.82 | 23.3 |
| 15 | 3.65 | 24.3 |

Crystalline modification A1 was further characterized by IR- and Raman-spectroscopy. FT-Raman and FT-IR spectra were obtained by standard techniques as described in the European Pharmacopeia 6$^{th}$ Edition chapter 2.02.24 and 2.02.48. For measurement of the FT-IR and FT-Raman-spectra a Bruker Vector 22 and a Bruker RFS 100 spectrometer were used. FT-IR spectra were base-line corrected using Bruker OPUS software. FT-Raman spectra were vector normalized using the same software.

Figure 2:
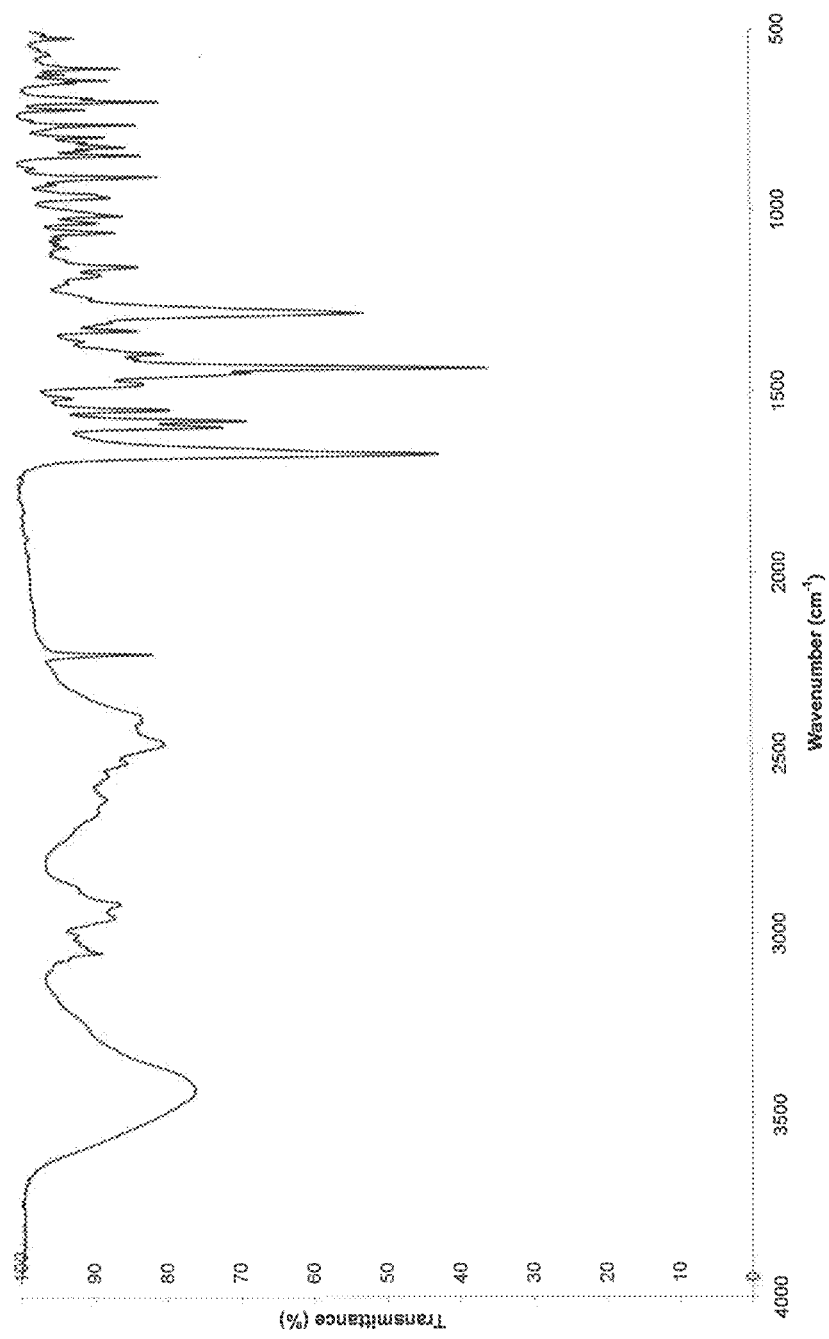
FIG. 2 depicts the FT-IR spectrum of crystalline modification A1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate.

An FT-IR spectrum was obtained using a KBr pellet as sample preparation technique. The FT-IR spectrum is depicted in FIG. 2 and the band positions are given below.

Crystalline modification A1 IR band positions ±2 cm$^{-1}$ (relative intensity*)

2951 cm$^{-1}$ (w), 2914 cm$^{-1}$ (w), 2472 cm$^{-1}$ (w), 2224 cm$^{-1}$ (w), 1671 cm$^{-1}$ (s), 1597 cm$^{-1}$ (w), 1579 cm$^{-1}$ (m), 1548 cm$^{-1}$ (w), 1433 cm$^{-1}$ (s), 1281 cm$^{-1}$ (m), 1153 cm$^{-1}$ (w), 1059 cm$^{-1}$ (w), 1012 cm$^{-1}$ (w), 905 cm$^{-1}$ (w), 846 cm$^{-1}$ (w), 822 cm$^{-1}$ (w), 761 cm$^{-1}$ (w), 697 cm$^{-1}$ (w)

*"s"=strong (transmittance≤50%), "m"=medium (50%<transmittance≤70%), "w"=weak (transmittance>70%)

Figure 3:
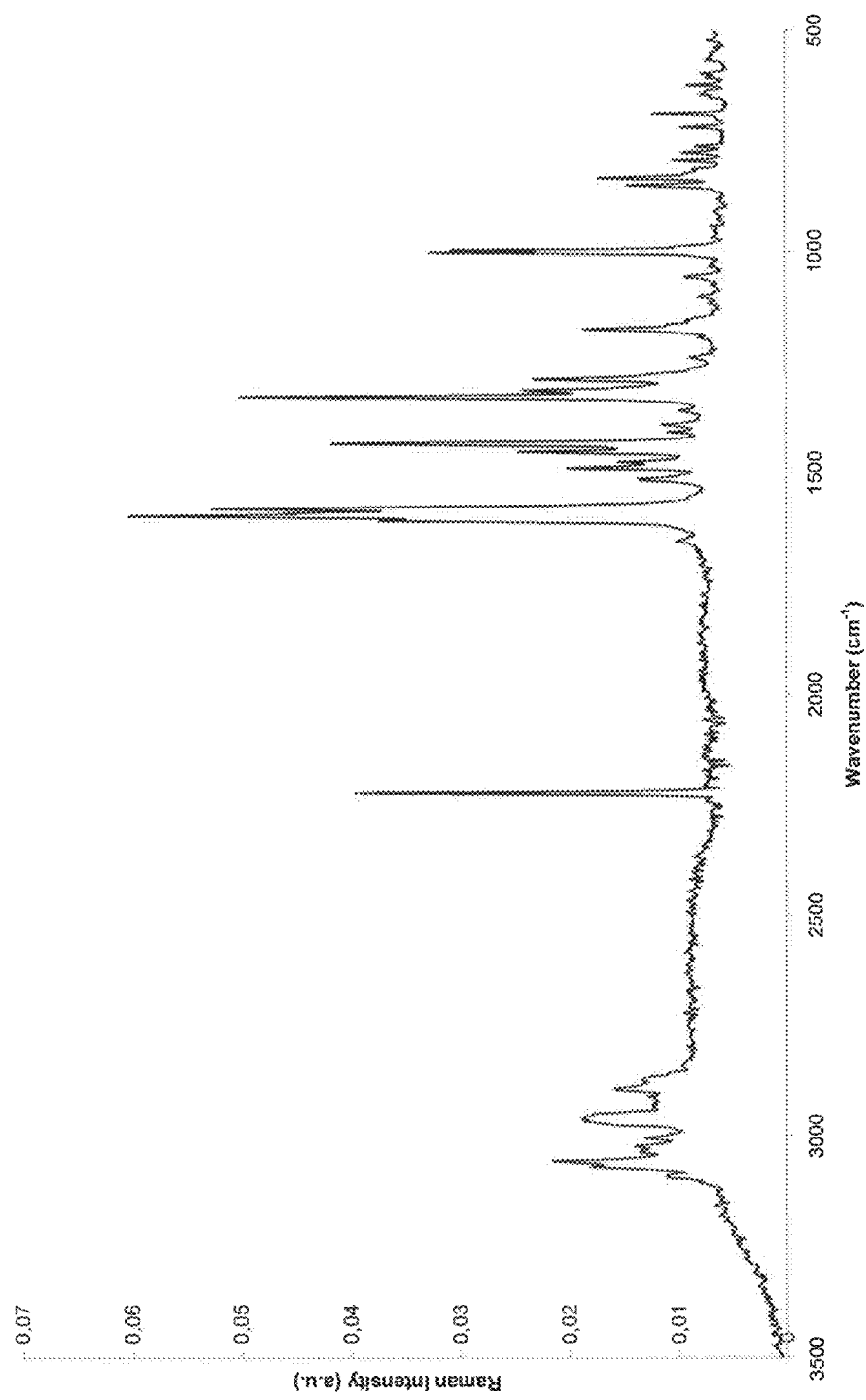
FIG. 3 depicts the FT-Raman spectrum of crystalline modification A1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate.

An FT-Raman spectrum is depicted in FIG. 3 and the band positions are given below.

Crystalline modification A1 Raman band positions+2 cm$^{-1}$ (relative intensity*):

3057 cm$^{-1}$ (m), 2960 cm$^{-1}$ (w), 2895 cm$^{-1}$ (w), 2224 cm$^{-1}$ (s), 1598 cm$^{-1}$ (s), 1582 cm$^{-1}$ (s), 1489 cm$^{-1}$ (m), 1453 cm$^{-1}$ (m), 1434 cm$^{-1}$ (s), 1328 cm$^{-1}$ (s), 1314 cm$^{-1}$ (m), 1289 cm$^{-1}$ (m), 1175 cm$^{-1}$ (w), 1002 cm$^{-1}$ (m), 996 cm$^{-1}$ (m), 849 cm$^{-1}$ (w), 833 cm$^{-1}$ (w) *"s"=strong (relative Raman intensity≥0.04), "m"=medium (0.04>relative Raman intensity≥0.02), "w"=weak (relative Raman intensity<0.02)

Figure 4:
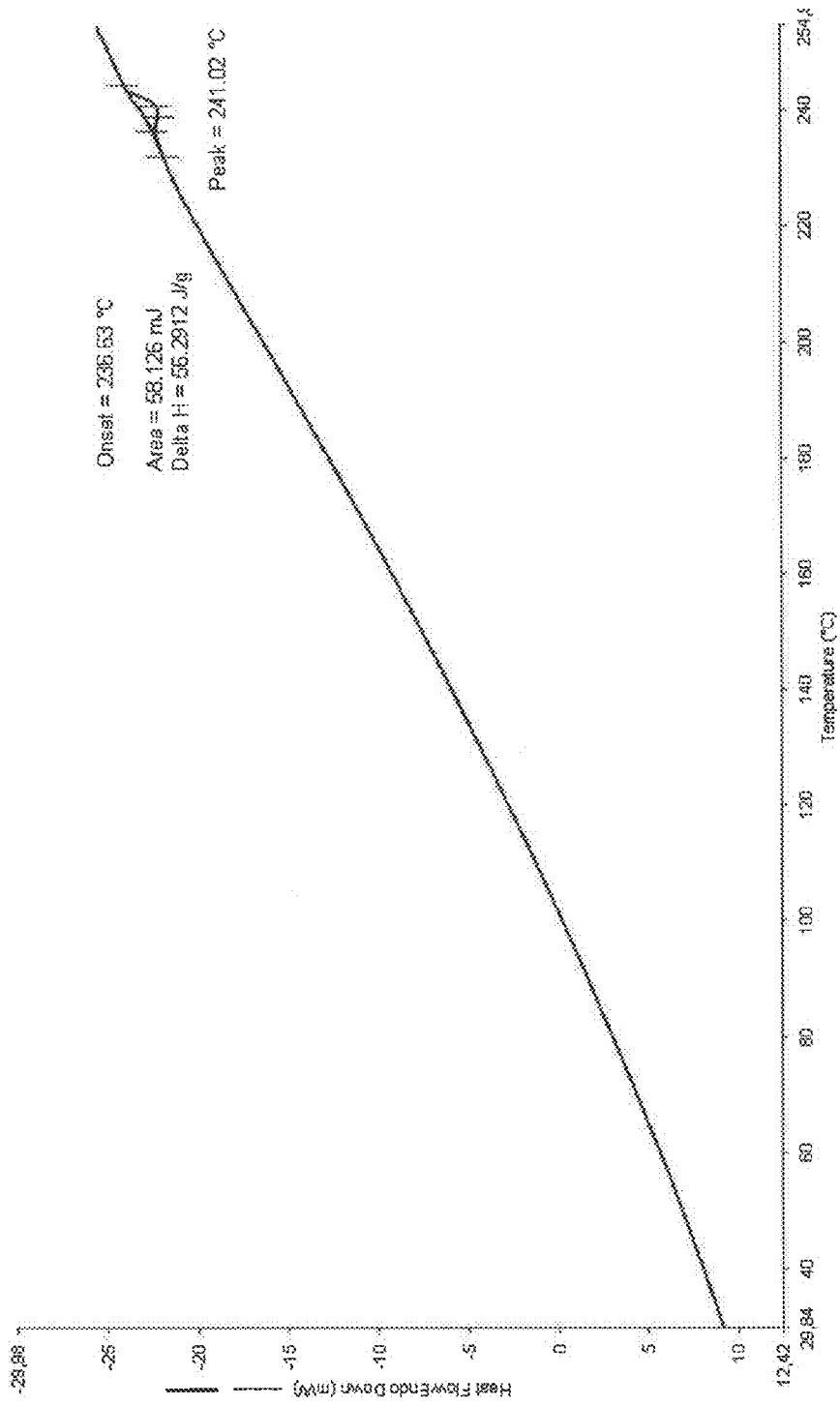
FIG. 4 depicts the DSC scan profile (Perkin-Elmer Diamond DSC, 5 K/min, nitrogen purge gas 50 mL/min) of crystalline modification A1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate.
Figure 5:
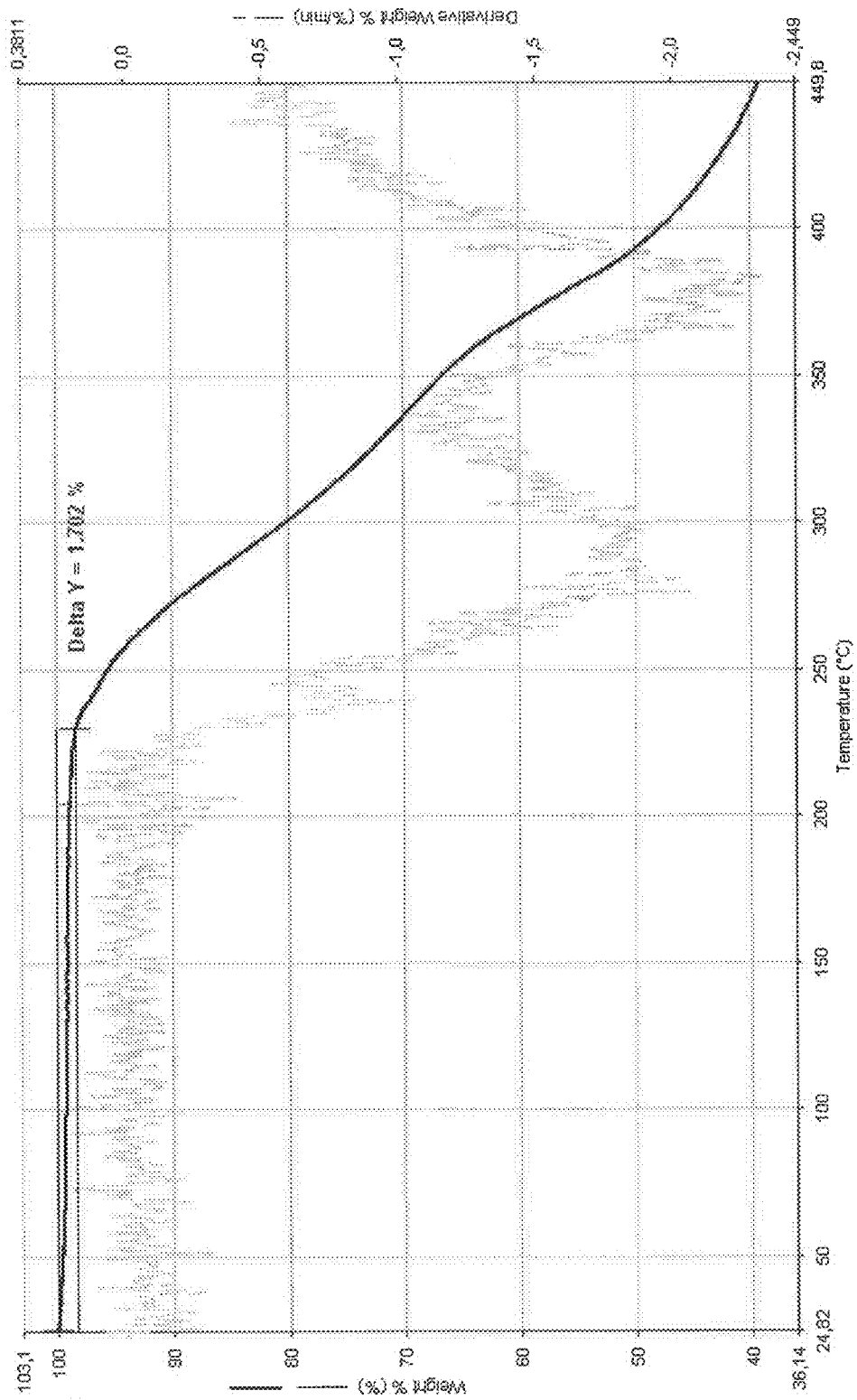
FIG. 5 depicts the TGA scan profile (Perkin-Elmer Pyris TGA1, 5 K/min, nitrogen purge gas 50 mL/min) of crystalline modification A1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate.
Figure 6:
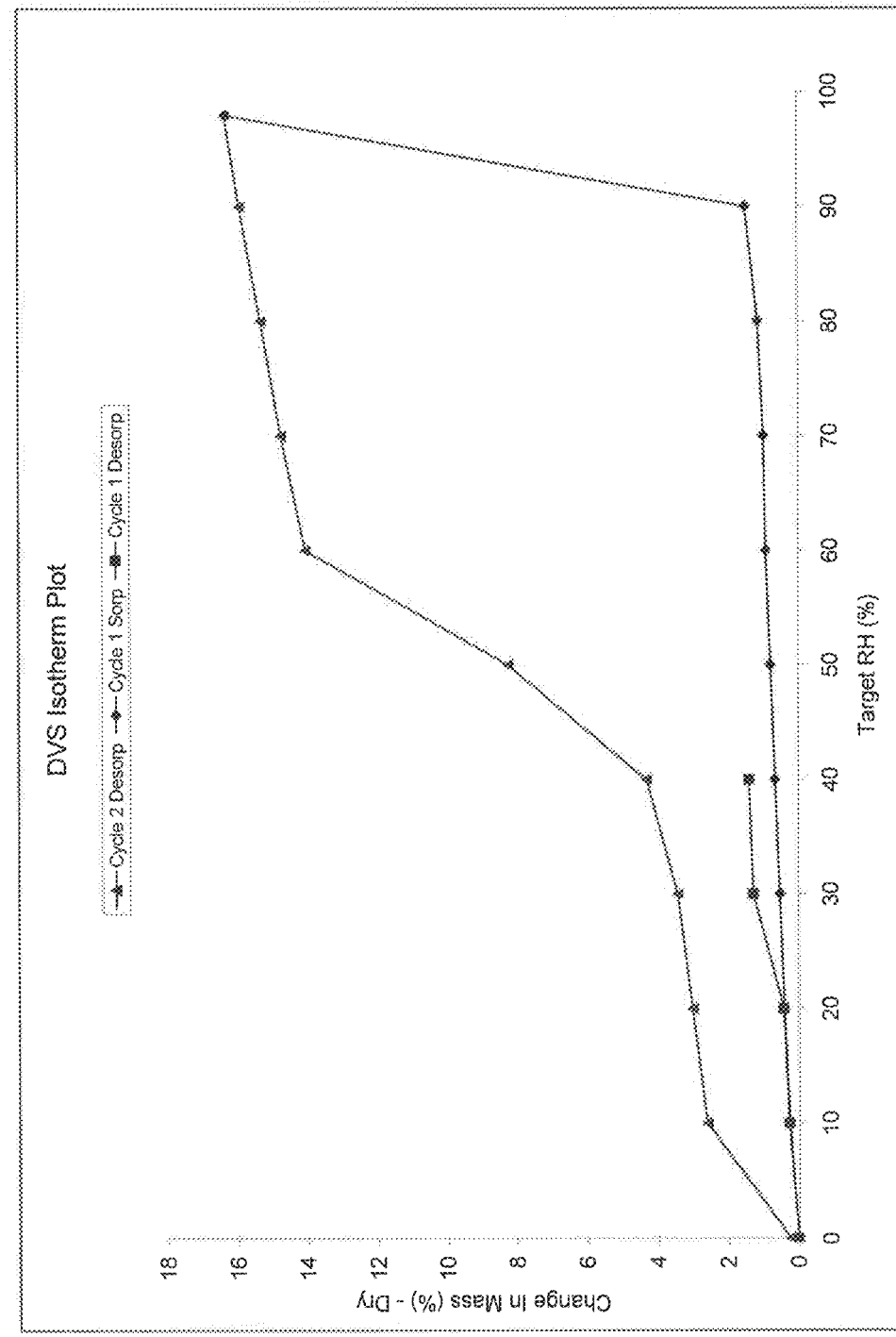
FIG. 6 depicts the Water Vapour Sorption Isotherm (25° C.) (SMS DVS 1) of crystalline modification A1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate.

Crystalline modification A1 is a crystalline anhydrous form, which is further characterized by the following physical properties:

Thermal behavior shows a melting peak at approx. 236° C., with a very small mass loss up to the melting temperature. DSC profile (Perkin-Elmer Diamond DSC, 5 K/min, nitrogen purge gas 50 mL/min) and TGA profile (Perkin-Elmer Pyris TGA1, 5 K/min, nitrogen purge gas 50 mL/min) are displayed in FIGS. 4 and 6, respectively.

Water Vapor Sorption behavior shows very small water uptake levels upon adsorption in the range 0-90% relative humidity (RH), and strongly hygroscopic behavior at 98% RH (water uptake levels >15 wt %). Water Vapor Sorption isotherm (25° C.) of crystalline modification A1 is displayed in FIG. 6.

Solubility of crystalline modification A1 in Simulated Gastric Fluid (acc. to USP) at ambient conditions (approx. 20-25° C.) was determined to be approx. 220 μg/mL.

Example 9

Structural and physico-chemical characterization of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate in its crystalline modification H1

Figure 7:
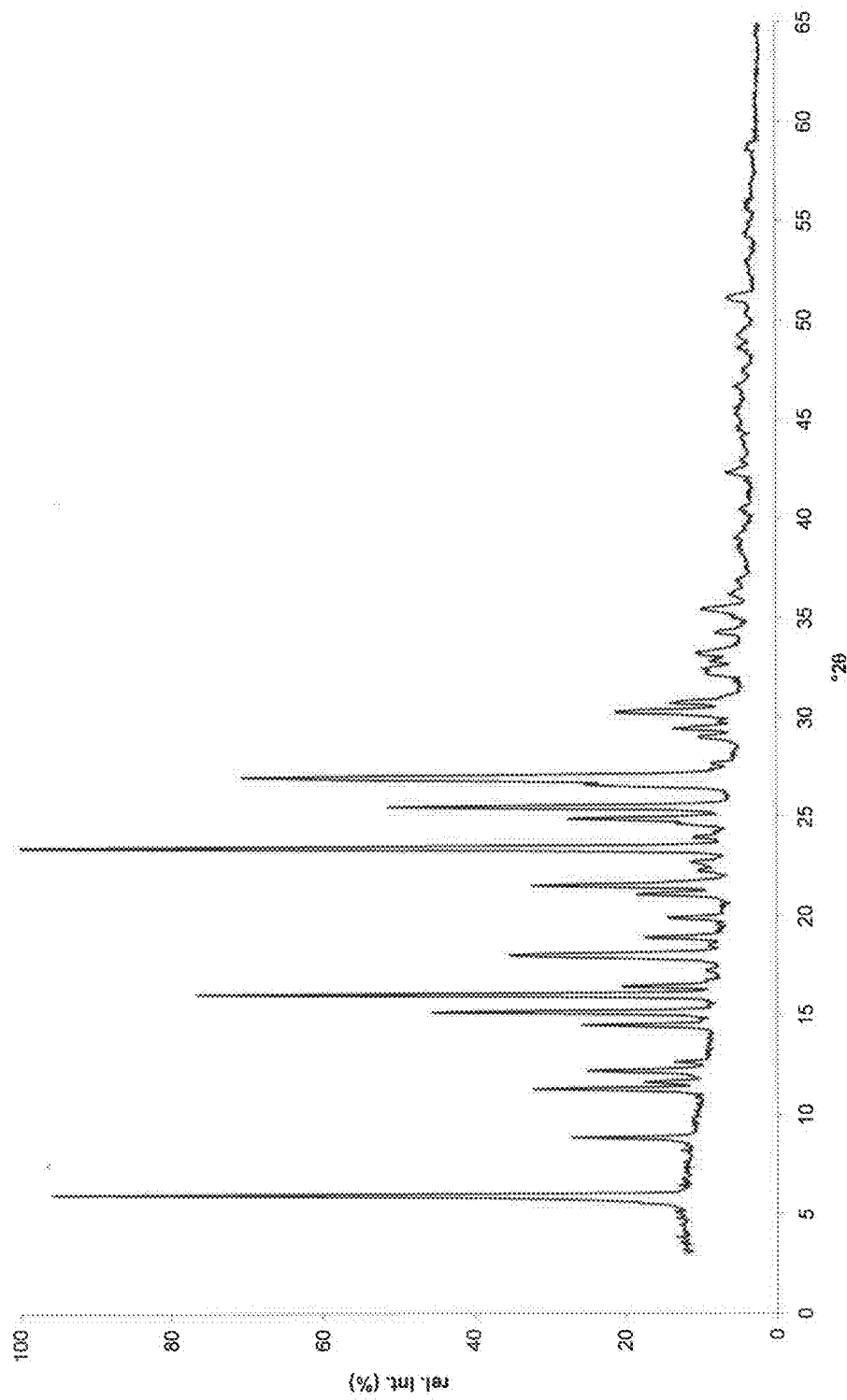
FIG. 7 depicts the powder X-ray diffractogram of crystalline modification H1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.

A Powder X-Ray Diffraction pattern of crystalline modification H1 was obtained by standard techniques as described in the European Pharmacopeia 6$^{th}$ Edition chapter 2.9.33, and is characterized by the following X-ray powder diffractogram (Cu—Kα$_1$ radiation, λ=1.5406 Å, Stoe StadiP 611 KL diffractometer) depicted in FIG. 7.

Crystalline modification H1 is characterized by the following XRD data:

| Powder X-ray diffractogram peak list: | | |
|---|---|---|
| Peak No. | d/Å | °2θ (Cu-Kα$_1$ radiation) ±0.1° |
| 1 | 14.88 | 5.9 |
| 2 | 9.99 | 8.8 |
| 3 | 7.83 | 11.3 |
| 4 | 7.25 | 12.2 |
| 5 | 6.10 | 14.5 |
| 6 | 5.84 | 15.2 |
| 7 | 5.52 | 16.0 |
| 8 | 5.38 | 16.5 |
| 9 | 4.92 | 18.0 |
| 10 | 4.12 | 21.6 |

| Powder X-ray diffractogram peak list: | | |
|---|---|---|
| Peak No. | d/Å | °2θ (Cu-Kα$_1$ radiation) ±0.1° |
| 11 | 3.80 | 23.4 |
| 12 | 3.57 | 24.9 |
| 13 | 3.49 | 25.5 |
| 14 | 3.30 | 27.0 |
| 15 | 2.95 | 30.3 |

Crystalline modification H1 was further characterized by IR- and Raman-spectroscopy. FT-Raman and FT-IR spectra were obtained by standard techniques as described in the European Pharmacopeia 6$^{th}$ Edition chapter 2.02.24 and 2.02.48. For measurement of the FT-IR and FT-Raman-spectra a Bruker Vector 22 and a Bruker RFS 100 spectrometer were used. FT-IR spectra were base-line corrected using Bruker OPUS software. FT-Raman spectra were vector normalized using the same software.

Figure 8:
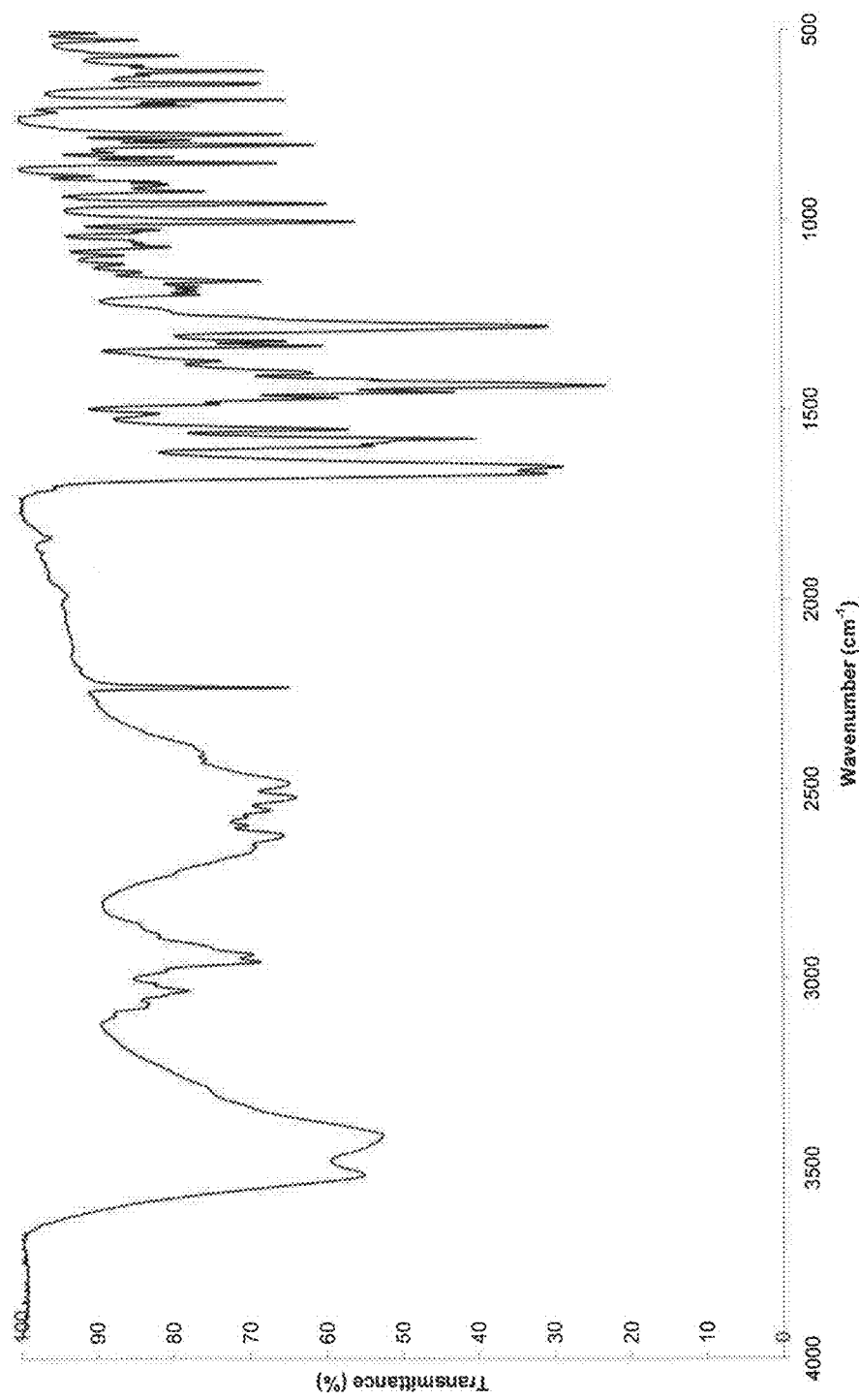
FIG. 8 depicts the FT-IR spectrum of crystalline modification H1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.

An FT-IR spectrum was obtained using a KBr pellet as sample preparation technique. The FT-IR spectrum is depicted in FIG. 8 and the band positions are given below.

Crystalline modification H1 IR band positions ±2 cm$^{-1}$ (relative intensity*)

3519 cm$^{-1}$ (m), 3415 cm$^{-1}$ (m), 3032 cm$^{-1}$ (w), 2956 cm$^{-1}$ (m), 2521 cm$^{-1}$ (m), 2232 cm$^{-1}$ (m), 1669 cm$^{-1}$ (s), 1651 cm$^{-1}$ (s), 1577 cm$^{-1}$ (s), 1551 cm$^{-1}$ (m), 1438 cm$^{-1}$ (s), 1282 cm$^{-1}$ (s), 1159 cm$^{-1}$ (m), 1070 cm$^{-1}$ (w), 1004 cm$^{-1}$ (m), 957 cm$^{-1}$ (m), 850 cm$^{-1}$ (m), 801 cm$^{-1}$ (m), 773 cm$^{-1}$ (m), 682 cm$^{-1}$ (m)

*"s"=strong (transmittance≤50%), "m"=medium (50%<transmittance≤70%), "w"=weak transmittance>70%)

Figure 9:
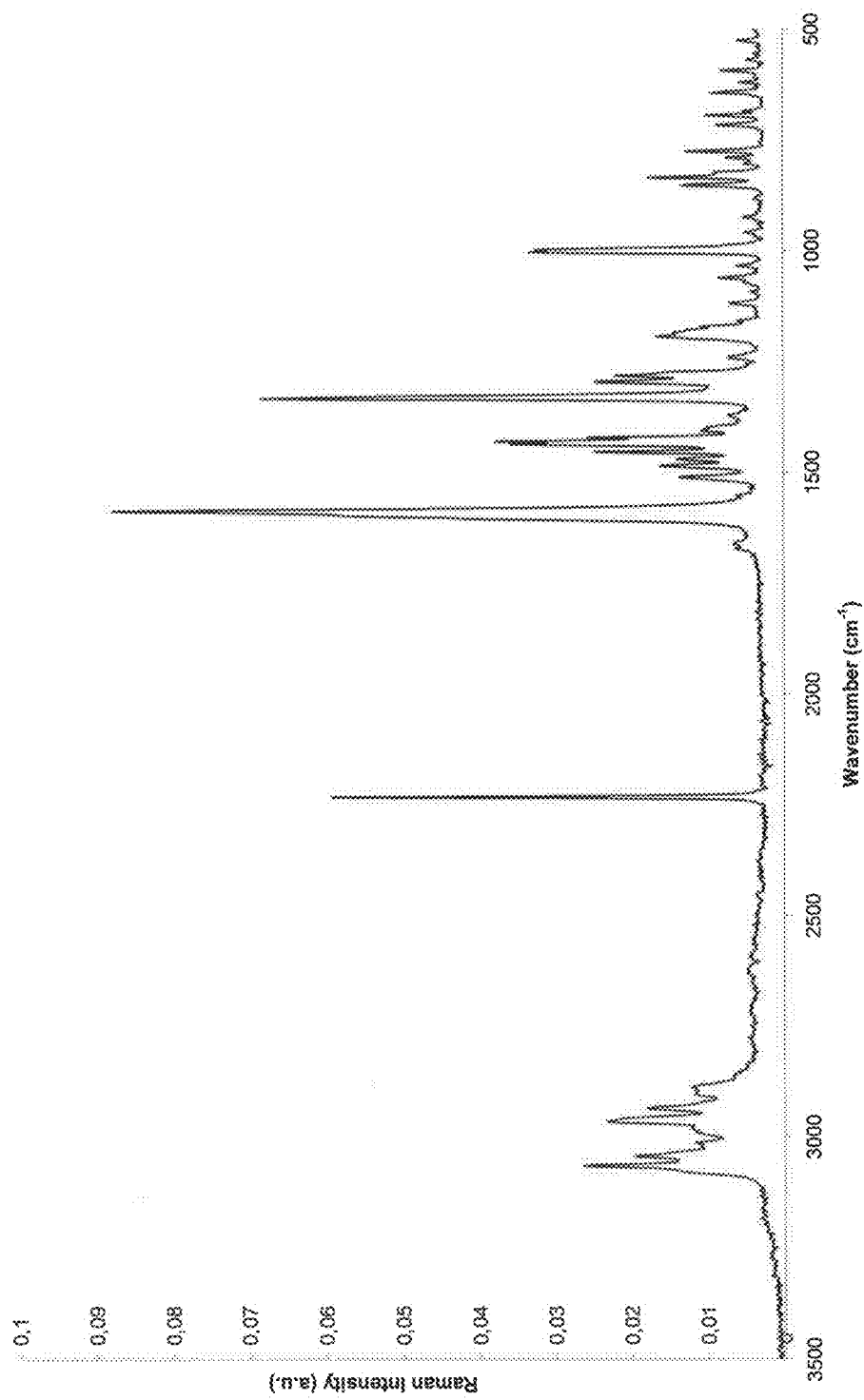
FIG. 9 depicts the FT-Raman spectrum of crystalline modification H1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.

An FT-Raman spectrum is depicted in FIG. 9 and the band positions are given below.

Crystalline modification H1 Raman band positions ±2 cm$^{-1}$ (relative intensity*):

3065 cm$^{-1}$ (m), 2965 cm$^{-1}$ (w), 2936 cm$^{-1}$ (w), 2232 cm$^{-1}$ (s), 1586 cm$^{-1}$ (s), 1485 cm$^{-1}$ (w), 1453 cm$^{-1}$ (m), 1429 cm$^{-1}$ (m), 1332 cm$^{-1}$ (s), 1295 cm$^{-1}$ (m), 1281 cm$^{-1}$ (m), 1192 cm$^{-1}$ (w), 1002 cm$^{-1}$ (m), 851 cm$^{-1}$ (w), 834 cm$^{-1}$ (w)

*"s"=strong (relative Raman intensity≥0.04), "m"=medium (0.04>relative Raman intensity≥0.02), "w"=weak (relative Raman intensity<0.02)

Figure 10:
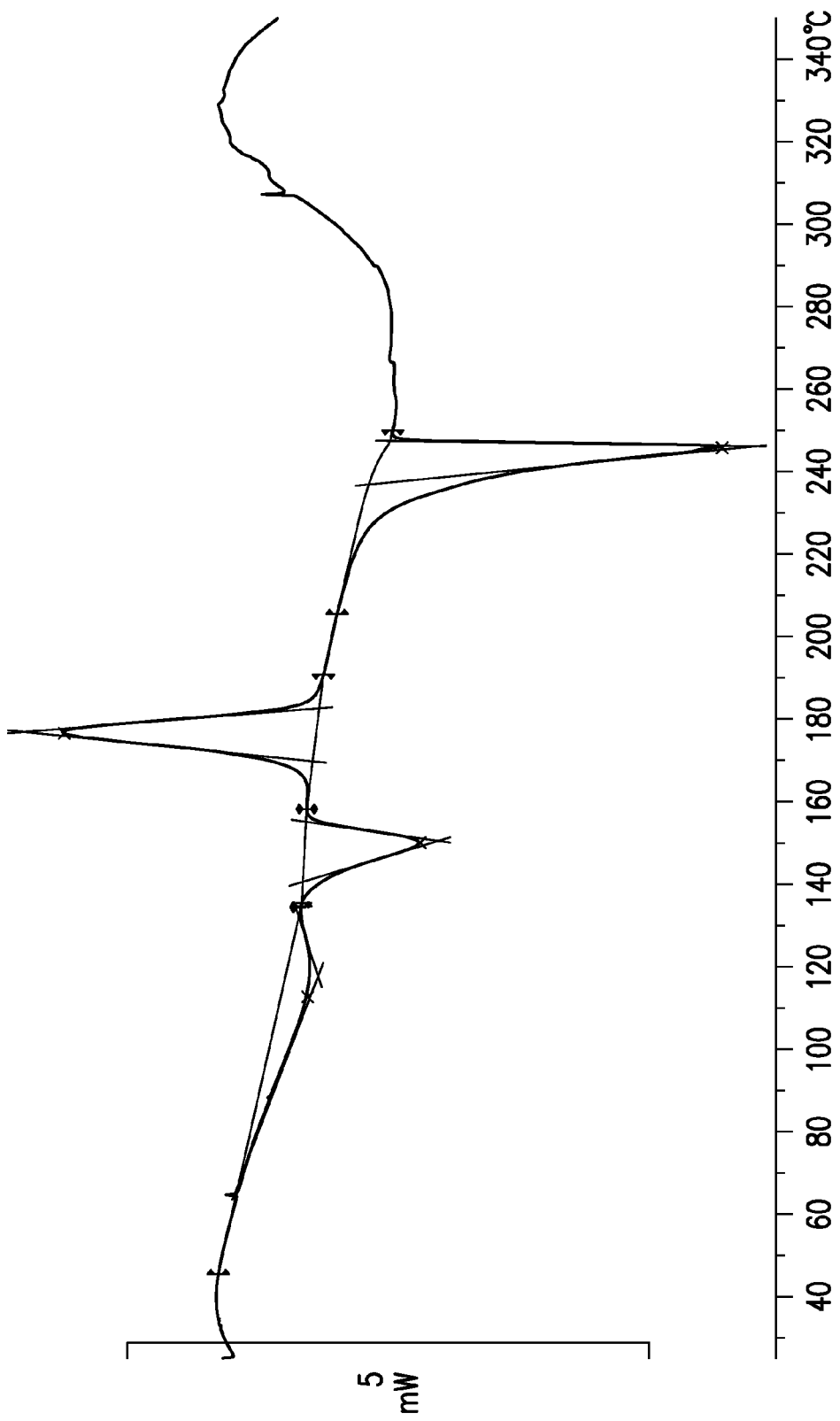
FIG. 10 depicts the DSC scan profile (Mettler-Toledo DSC 821, 5 K/min, nitrogen purge gas 50 mL/min) of crystalline modification H1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.
Figure 11:
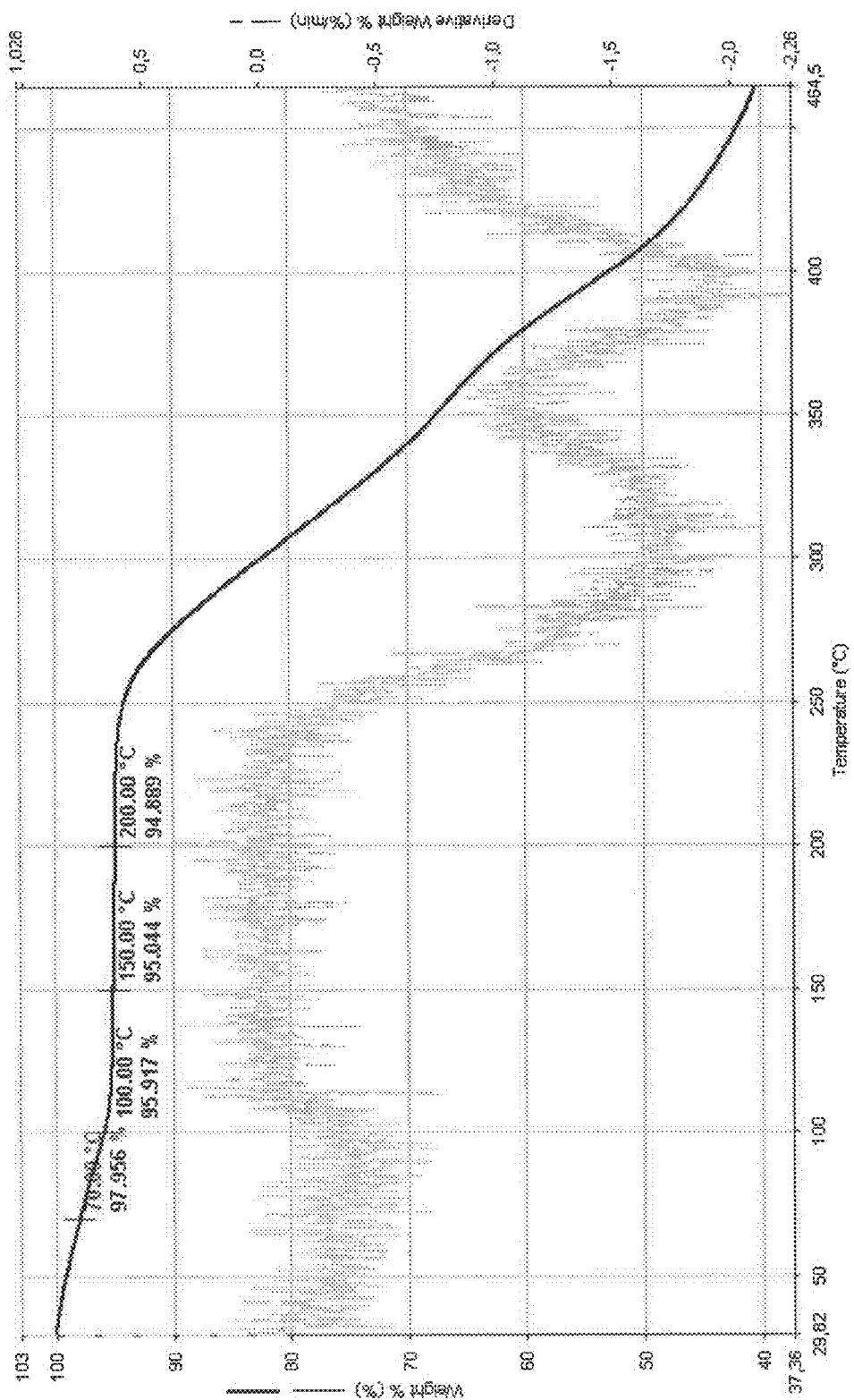
FIG. 11 depicts the TGA scan profile (Perkin-Elmer Pyris TGA1, 5 K/min, nitrogen purge gas 50 mL/min) of crystalline modification H1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.

Crystalline modification H1 is a crystalline hydrate form, which is further characterized by the following physical properties:

Thermal behavior shows dehydration of hydrate water from approx. 50-120° C. upon heating with loss of crystallinity and subsequent re-crystallisation of the anhydrous form. At approx. 230° C. melting occurs. DSC profile (Mettler-Toledo DSC 821, 5 K/min, nitrogen purge gas 50 mL/min) and TGA profile (Perkin-Elmer Pyris TGA1, 5 K/min, nitrogen purge gas 50 mL/min) are displayed in FIGS. 10 and 11, respectively.

Figure 12:
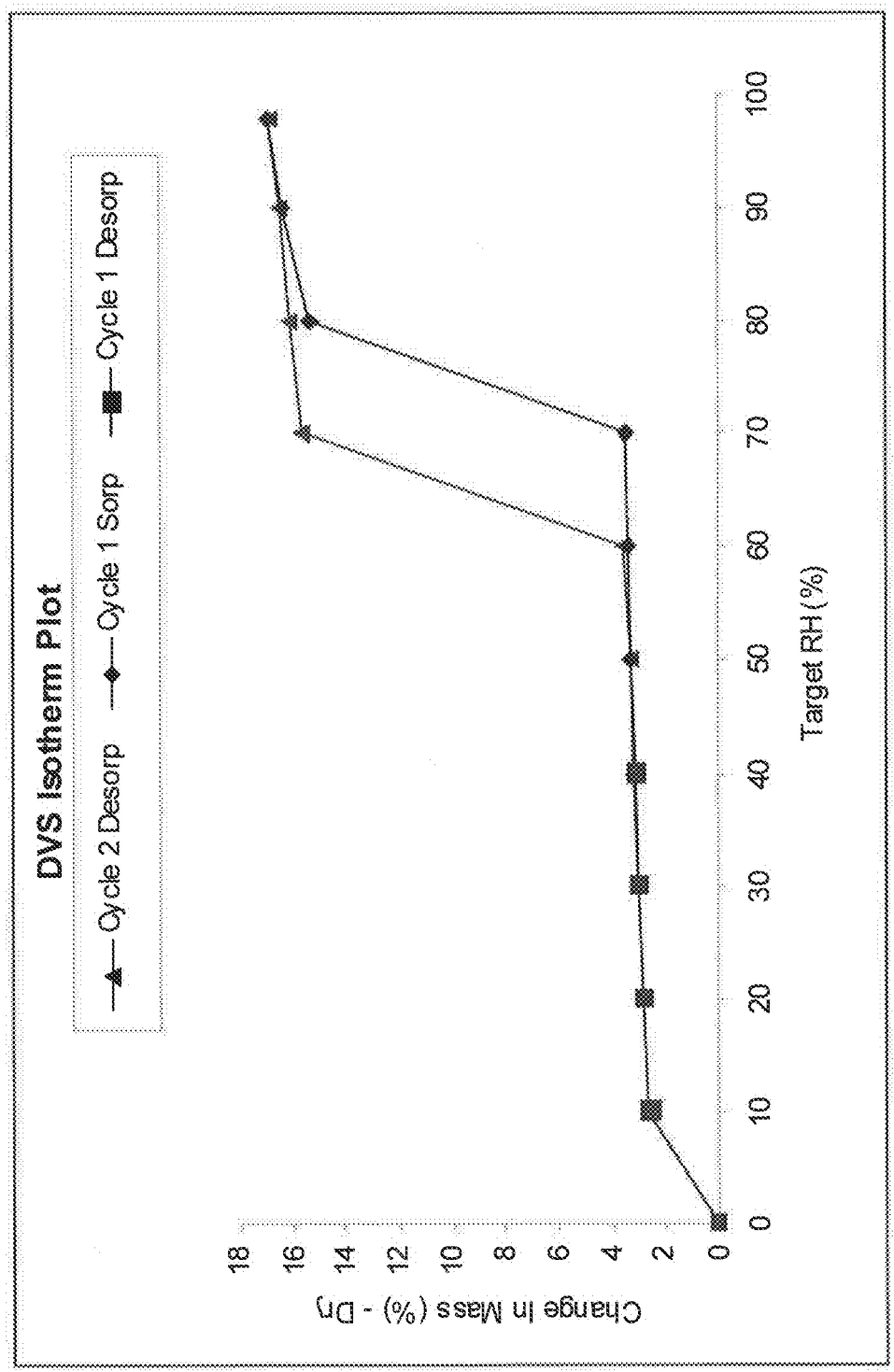
FIG. 12 depicts the Water Vapour Sorption Isotherm (25° C.) (SMS DVS Intrinsic) of crystalline modification H1 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.

Water Vapor Sorption behavior shows strongly hygroscopic behaviour at relative humidity (RH) levels >70% (with water uptake levels of >15 wt % at 80% RH). Water Vapor Sorption isotherm (25° C.) of crystalline modification H1 is displayed in FIG. 12.

Kinetic Solubility (after 60 minutes) of crystalline modification H1 in 0.1N HCl (pH 1.0) at room temperature (approx. 20-25° C.) was determined to be approx. 3 μg/mL.

Example 10

Structural and physico-chemical characterization of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate in its crystalline modification NF3

Figure 13:
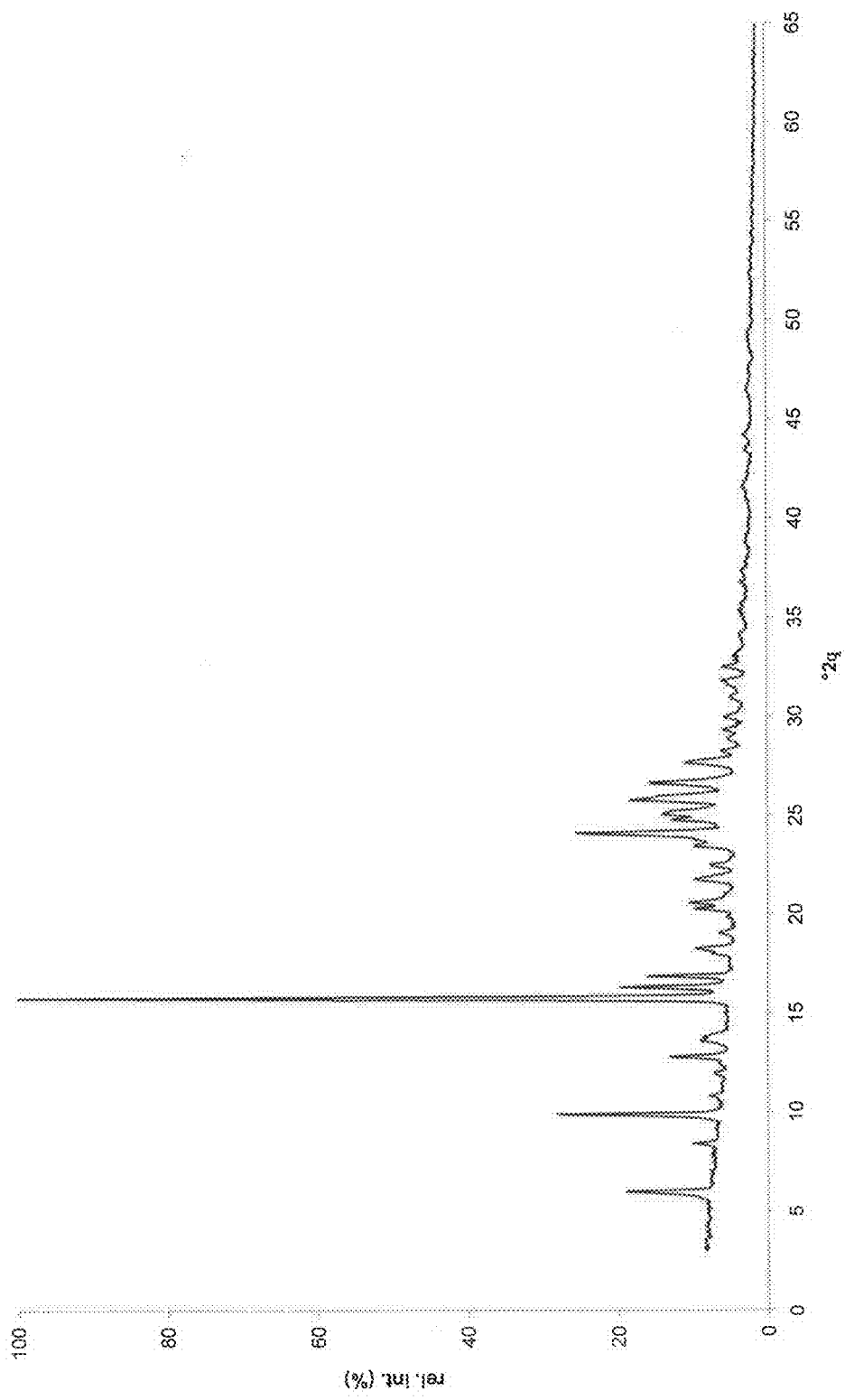
FIG. 13 depicts the powder X-ray diffractogram of crystalline modification NF3 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.

A Powder X-Ray Diffraction pattern of crystalline modification NF3 was obtained by standard techniques as described in the European Pharmacopeia 6$^{th}$ Edition chapter 2.9.33, and is characterized by the following X-ray powder diffractogram (Cu—K$\alpha_1$ radiation, $\lambda$=1.5406 Å, Stoe StadiP 611 KL diffractometer) depicted in FIG. 13.

Crystalline modification NF3 is characterized by the following XRD data:

Powder X-ray diffractogram peak list:

| Peak No. | d/Å | °2θ (Cu—K$\alpha_1$ radiation) ± 0.1° |
|---|---|---|
| 1 | 14.83 | 6.0 |
| 2 | 8.96 | 9.9 |
| 3 | 6.92 | 12.8 |
| 4 | 5.62 | 15.7 |
| 5 | 5.44 | 16.3 |
| 6 | 5.26 | 16.9 |
| 7 | 4.38 | 20.3 |
| 8 | 4.32 | 20.6 |
| 9 | 3.79 | 23.5 |
| 10 | 3.69 | 24.1 |
| 11 | 3.59 | 24.8 |
| 12 | 3.55 | 25.1 |
| 13 | 3.45 | 25.8 |
| 14 | 3.35 | 26.6 |
| 15 | 3.22 | 27.7 |

Crystalline modification NF3 was further characterized by IR- and Raman-spectroscopy. FT-Raman and FT-IR spectra were obtained by standard techniques as described in the European Pharmacopeia 6$^{th}$ Edition chapter 2.02.24 and 2.02.48. For measurement of the FT-IR and FT-Raman-spectra a Bruker Vector 22 and a Bruker RFS 100 spectrometer were used. FT-IR spectra were base-line corrected using Bruker OPUS software. FT-Raman spectra were vector normalized using the same software.

Figure 14:
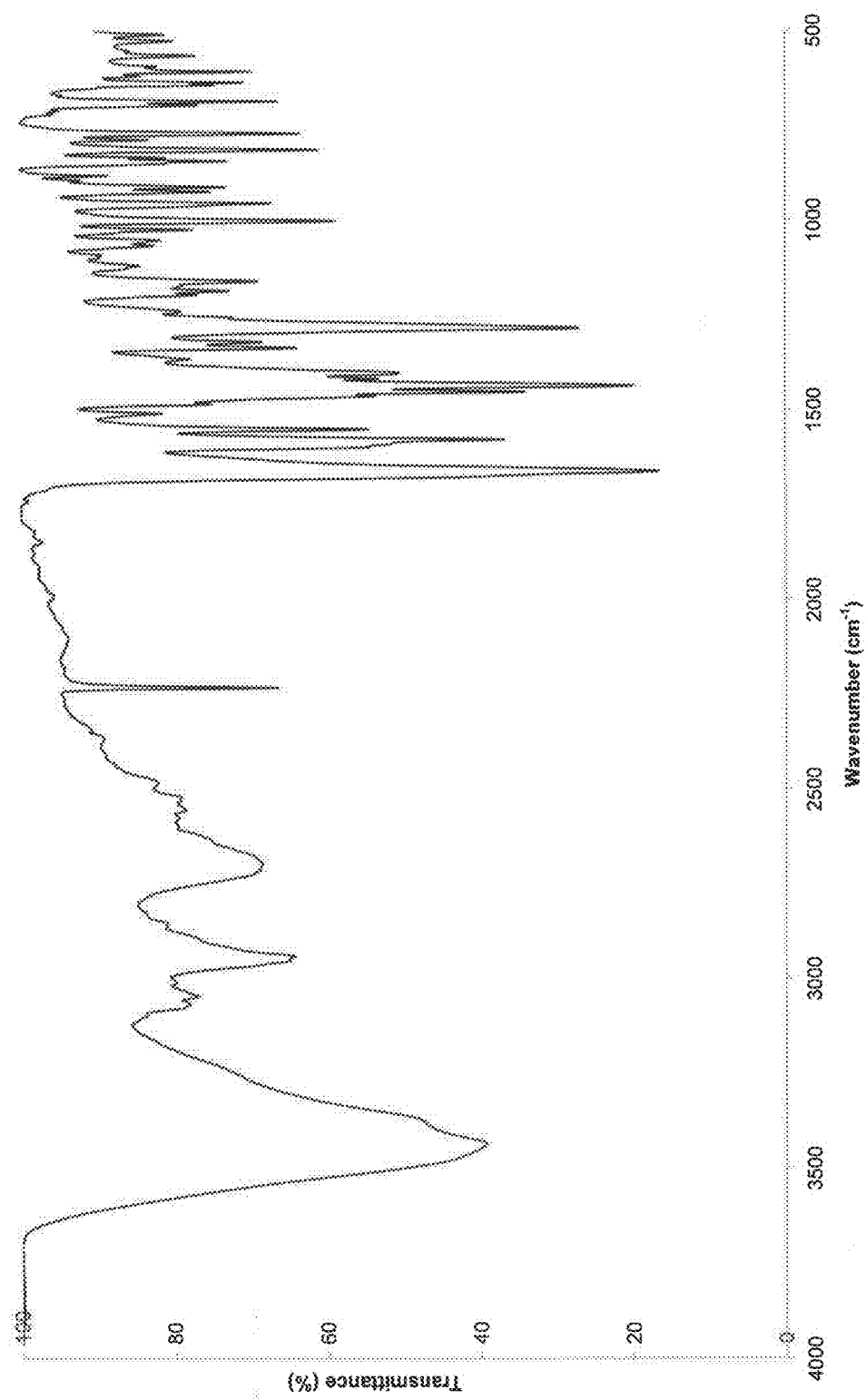
FIG. 14 depicts the FT-IR spectrum of crystalline modification NF3 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.

An FT-IR spectrum was obtained using a KBr pellet as sample preparation technique. The FT-IR spectrum is depicted in FIG. 14 and the band positions are given below.

Crystalline modification NF3 IR band positions ±2 cm$^{-1}$ (relative intensity*)

3437 cm$^{-1}$ (s), 2941 cm$^{-1}$ (m), 2697 cm$^{-1}$ (m), 2232 cm$^{-1}$ (m), 1661 cm$^{-1}$ (s), 1578 cm$^{-1}$ (s), 1551 cm$^{-1}$ (m), 1436 cm$^{-1}$ (s), 1284 cm$^{-1}$ (s), 1160 cm$^{-1}$ (m), 1001 cm$^{-1}$ (m), 954 cm$^{-1}$ (m), 842 cm$^{-1}$ (w), 813 cm$^{-1}$ (m), 770 cm$^{-1}$ (m), 685 cm$^{-1}$ (m)

*"s"=strong (transmittance≤50%), "m"=medium (50%<transmittance≤70%), "w"=weak (transmittance>70%)

Figure 15:
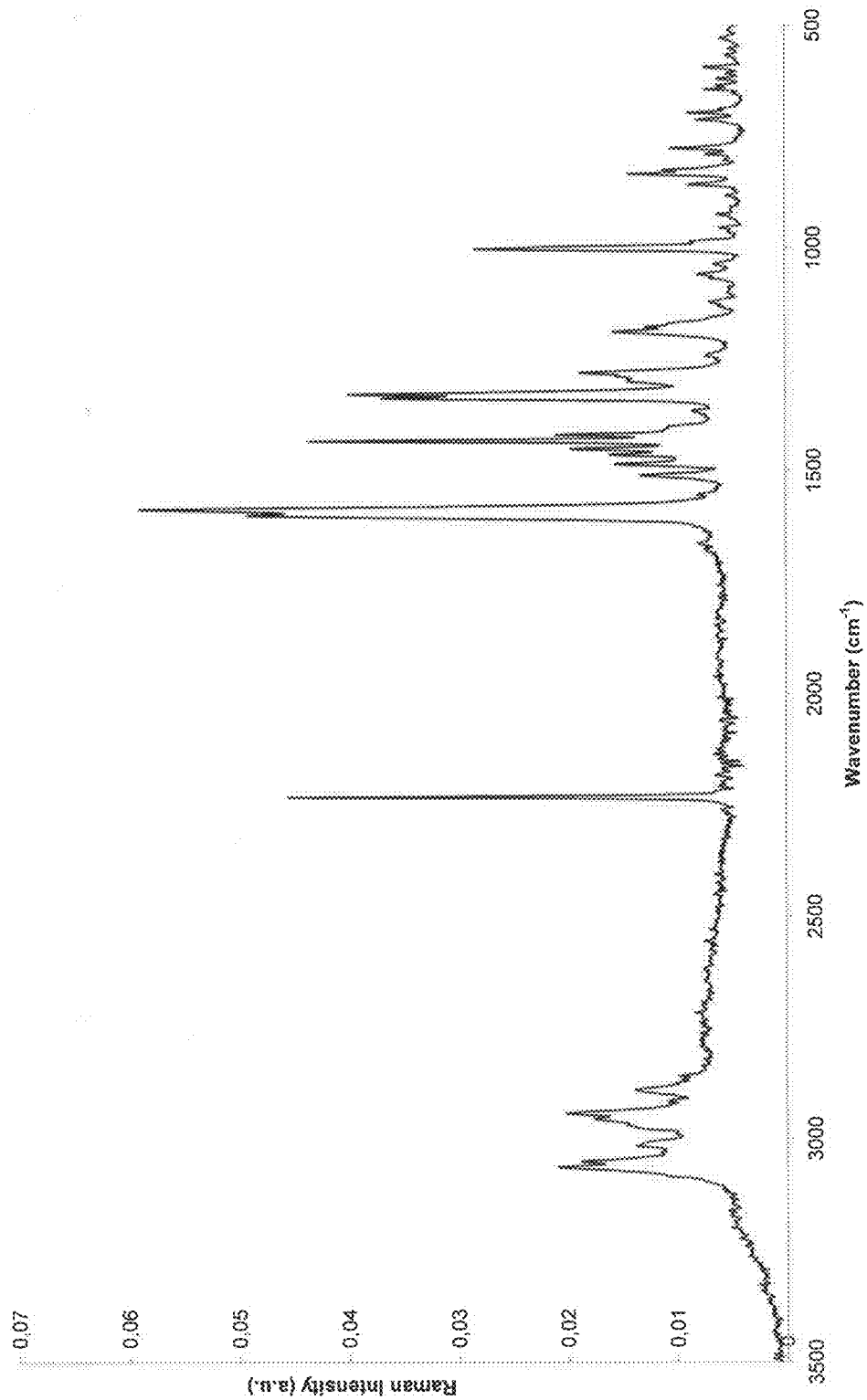
FIG. 15 depicts the FT-Raman spectrum of crystalline modification NF3 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.

An FT-Raman spectrum is depicted in FIG. 15 and the band positions are given below.

Crystalline modification NF3 Raman band positions ±2 cm$^{-1}$ (relative intensity*):

3064 cm$^{-1}$ (m), 2944 cm$^{-1}$ (m), 2891 cm$^{-1}$ (w), 2232 cm$^{-1}$ (s), 1599 cm$^{-1}$ (s), 1585 cm$^{-1}$ (s), 1484 cm$^{-1}$ (w), 1450 cm$^{-1}$ (m), 1432 cm$^{-1}$ (s), 1336 cm$^{-1}$ (m), 1328 cm$^{-1}$ (s), 1280 cm$^{-1}$ (w), 1187 cm$^{-1}$ (w), 1002 cm$^{-1}$ (m), 833 cm$^{-1}$ (w)

*"s"=strong (relative Raman intensity≥0.04), "m"=medium (0.04>relative Raman intensity≥0.02), "w"=weak (relative Raman intensity<0.02).

Figure 16:
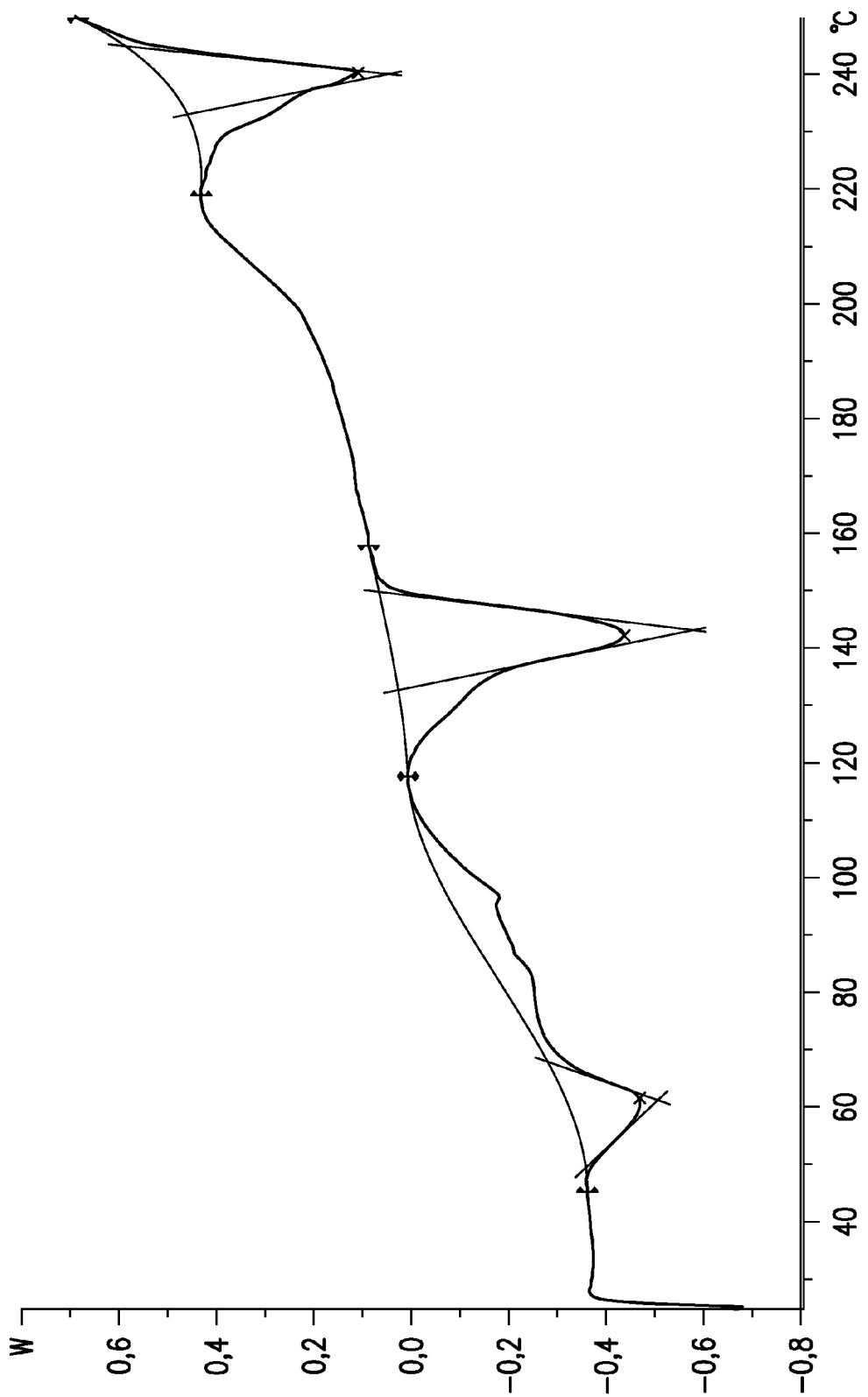
FIG. 16 depicts the DSC scan profile (Mettler-Toledo DSC 821, 5 K/min, nitrogen purge gas 50 mL/min) of crystalline modification NF3 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.
Figure 17:
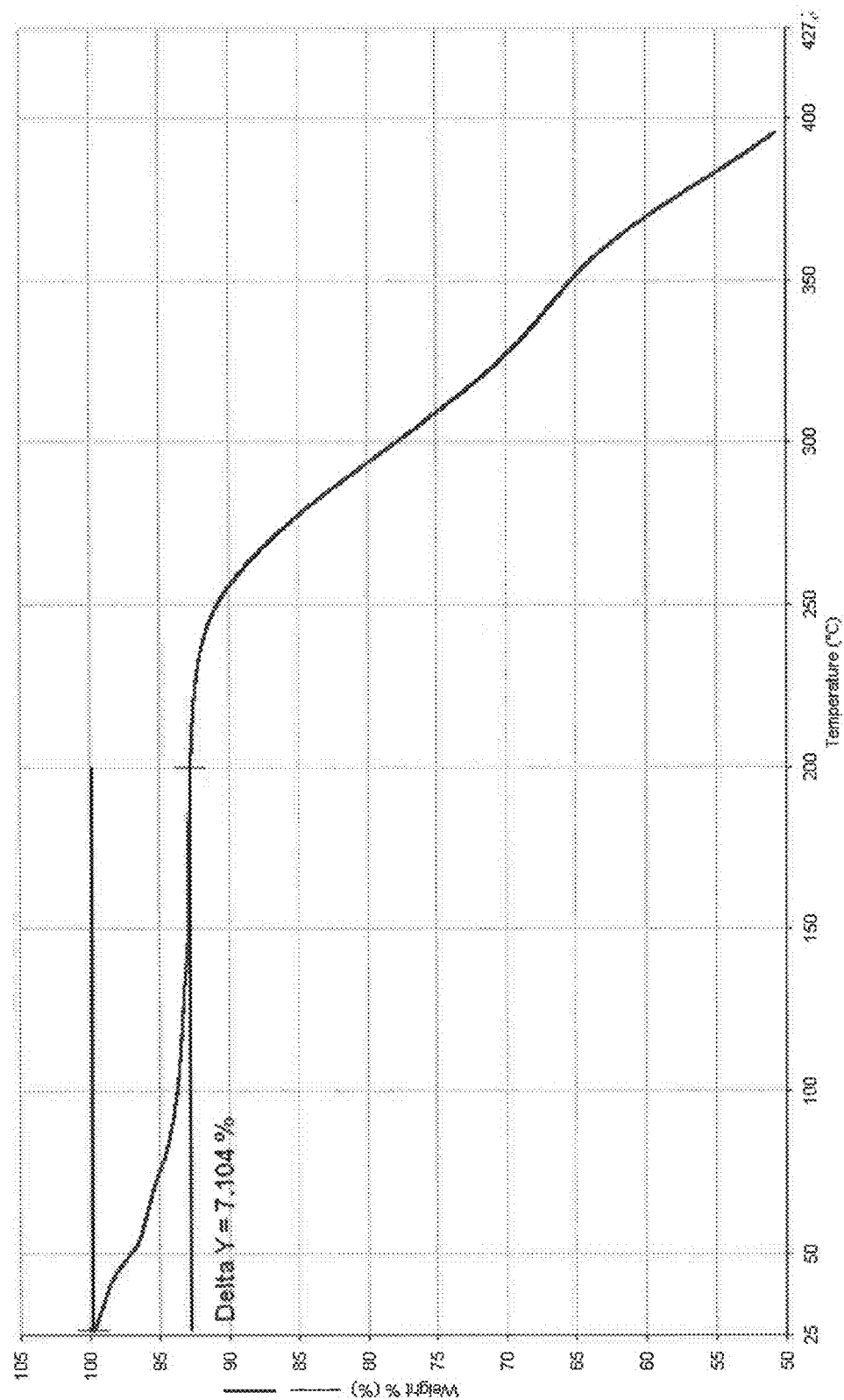
FIG. 17 depicts the TGA scan profile (Perkin-Elmer Pyris TGA1, 5 K/min, nitrogen purge gas 50 mL/min) of crystalline modification NF3 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.

Crystalline modification NF3 is a crystalline hydrate form, which is further characterized by the following physical properties:

Thermal behavior shows dehydration of hydrate water from approx. 40-120° C. upon heating with loss of crystallinity and subsequent re-crystallisation of the anhydrous form. At approx. 230° C. melting occurs. DSC profile (Mettler-Toledo DSC 821, 5 K/min, nitrogen purge gas 50 mL/min) and TGA profile (Perkin-Elmer Pyris TGA1, 5 K/min, nitrogen purge gas 50 mL/min) are displayed in FIGS. 16 and 17, respectively.

Figure 18:
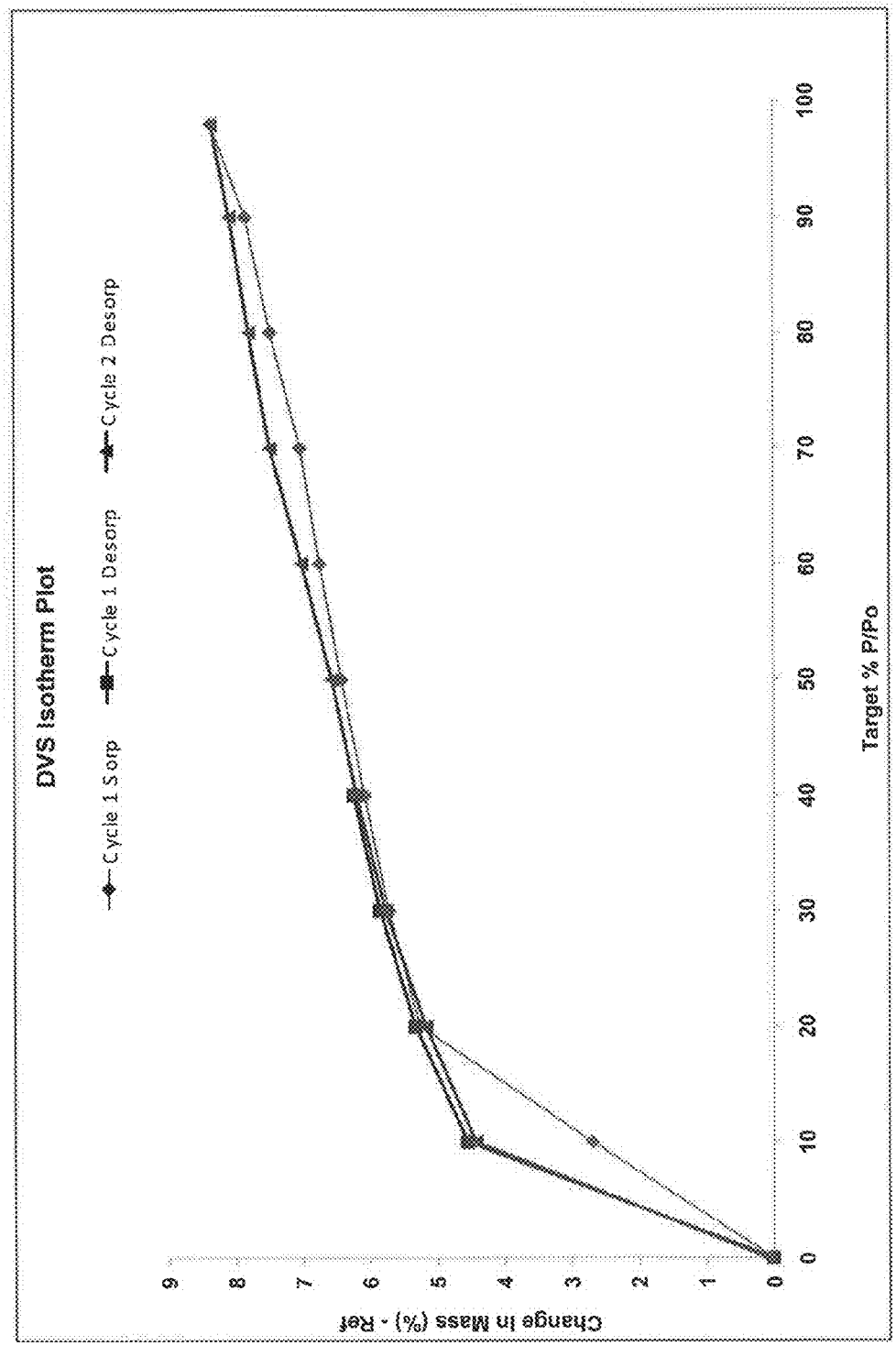
FIG. 18 depicts the Water Vapour Sorption Isotherm (25° C.) (SMS DVS Advantage) of crystalline modification NF3 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.

Water Vapor Sorption behavior shows continuous water uptake levels up to approx. 9 wt % at 98% relative humidity (RH). Acc. to Ph. Eur. criteria, Form NF3 can be classified as slightly-hygroscopic. Under dry conditions, dehydration of hydrate water occurs. Water Vapor Sorption isotherm (25° C.) of crystalline modification NF3 is displayed in FIG. 18.

Thermodynamic Solubility of crystalline modification NF3 in 0.1N HCl (pH 1.0) at 37° C. was determined to be approx. 70 µg/mL.

Example 11

Structural and physico-chemical characterization of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate in its crystalline modification H2

Figure 19:
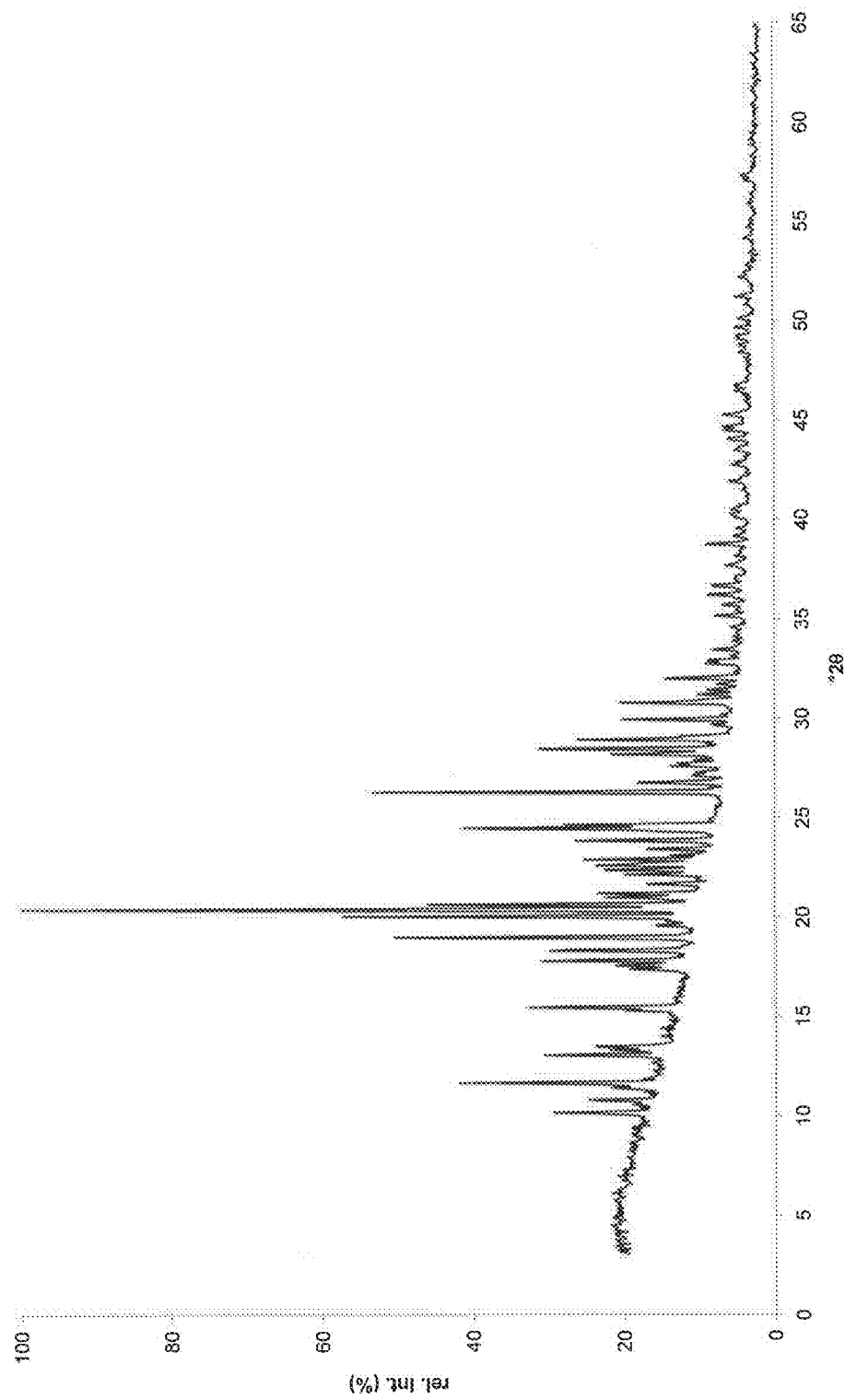
FIG. 19 depicts the powder X-ray diffractogram of crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate.

A Powder X-Ray Diffraction pattern of crystalline modification H2 was obtained by standard techniques as described in the European Pharmacopeia 6$^{th}$ Edition chapter 2.9.33, and is characterized by the following X-ray powder diffractogram (Cu—K$\alpha_1$ radiation, $\lambda$=1.5406 Å, Stoe StadiP 611 KL diffractometer) depicted in FIG. 19.

Crystalline modification H2 is characterized by the following XRD data:

Powder X-ray diffractogram peak list:

| Peak No. | d/Å | °2θ (Cu—K$\alpha_1$ radiation) ± 0.1° |
|---|---|---|
| 1 | 8.71 | 10.1 |
| 2 | 8.22 | 10.8 |
| 3 | 7.59 | 11.6 |
| 4 | 6.78 | 13.0 |
| 5 | 6.58 | 13.5 |
| 6 | 5.73 | 15.4 |
| 7 | 4.98 | 17.8 |
| 8 | 4.84 | 18.3 |
| 9 | 4.68 | 19.0 |
| 10 | 4.43 | 20.0 |
| 11 | 4.35 | 20.4 |
| 12 | 3.73 | 23.9 |
| 13 | 3.64 | 24.5 |
| 14 | 3.39 | 26.3 |
| 15 | 3.13 | 28.5 |

Figure 20:
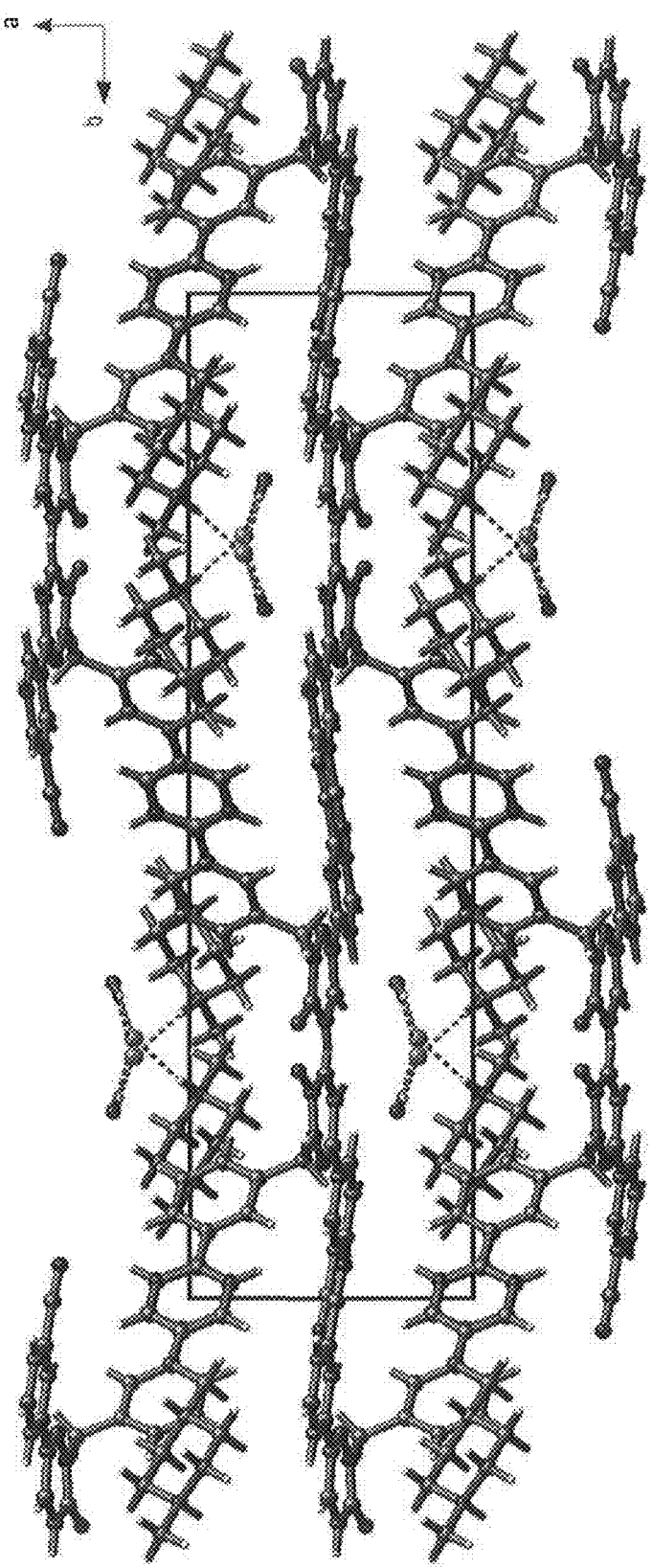
FIG. 20 depicts single crystal X-Ray Structure data of crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate viewed along c-axis.

Single crystal X-Ray Structure data were obtained on crystalline modification H2 as well (XCalibur diffractometer from Oxford Diffraction equipped with graphite monochromator and CCD Detector using Mo K$_\alpha$ radiation at 301 K). The single crystal structure of crystalline modification H2 viewed along c-axis is depicted in FIG. 20.

Crystalline modification H2 crystallizes in the monoclinic space group P2$_1$/c with the lattice parameters a=9.8 Å, b=31.0 Å, c=10.1 Å, and β=117.5° (with α=γ=90°). From the single crystal structure it is obvious that crystalline modification H2 represents a stoichiometric monohydrate.

Crystalline modification H2 was further characterized by IR- and Raman-spectroscopy. FT-Raman and FT-IR spectra were obtained by standard techniques as described in the European Pharmacopeia 6$^{th}$ Edition chapter 2.02.24 and 2.02.48. For measurement of the FT-IR and FT-Raman-spectra a Bruker Vector 22 and a Bruker RFS 100 spectrometer were used. FT-IR spectra were base-line corrected using Bruker OPUS software. FT-Raman spectra were vector normalized using the same software.

Figure 21:
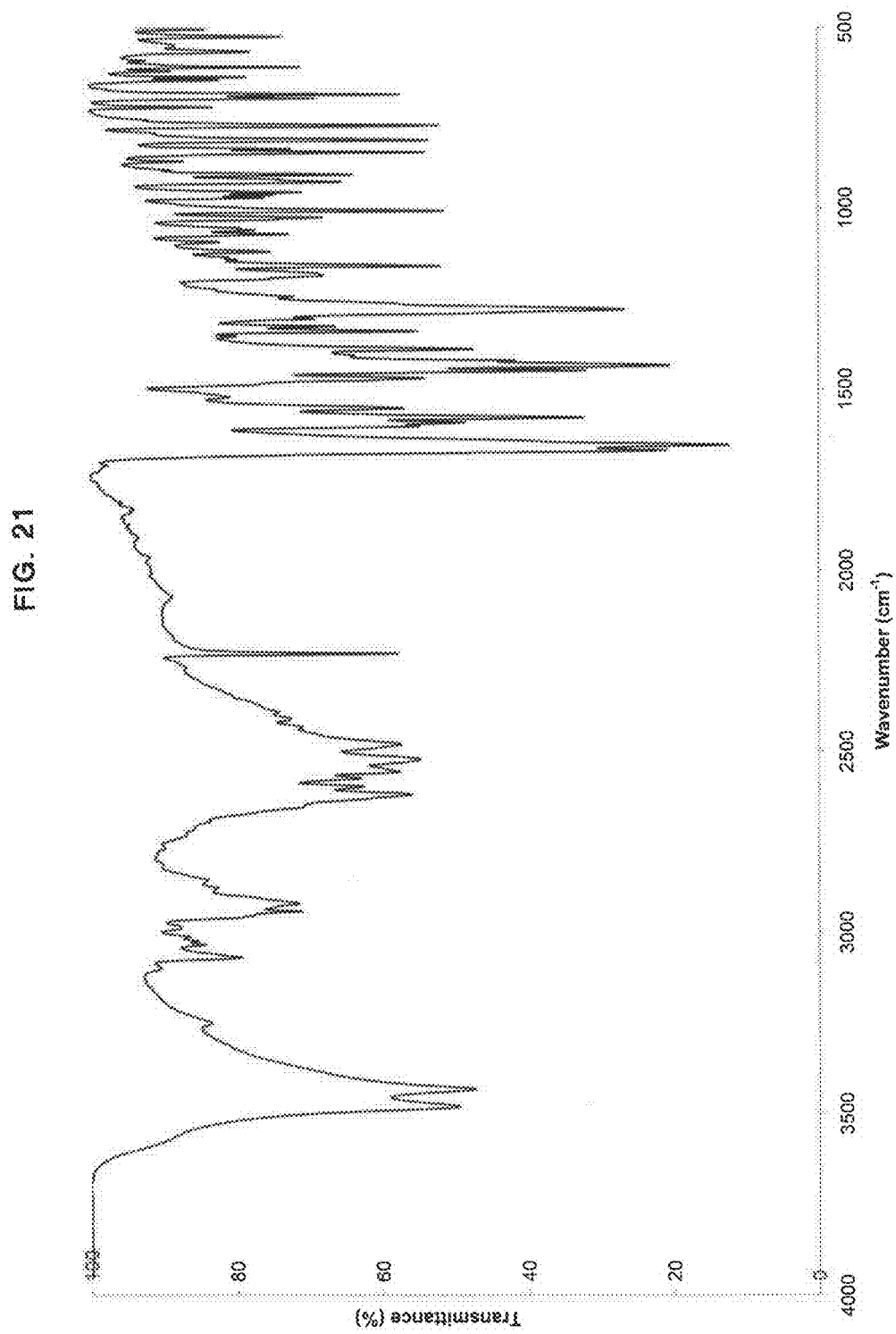
FIG. 21 depicts the FT-IR spectrum of crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate.

An FT-IR spectrum was obtained using a KBr pellet as sample preparation technique. The FT-IR spectrum is depicted in FIG. 21 and the band positions are given below.

Crystalline modification H2 IR band positions ±2 cm$^{-1}$ (relative intensity*)

3481 cm$^{-1}$ (s), 3433 cm$^{-1}$ (s), 3067 cm$^{-1}$ (w), 2919 cm$^{-1}$ (w), 2618 cm$^{-1}$ (m), 2520 cm$^{-1}$ (m), 2229 cm$^{-1}$ (m), 1669 cm$^{-1}$ (s), 1653 cm$^{-1}$ (s), 1591 cm$^{-1}$ (s), 1577 cm$^{-1}$ (s), 1551 cm$^{-1}$ (m), 1435 cm$^{-1}$ (s), 1279 cm$^{-1}$ (s), 1158 cm$^{-1}$ (m), 1070 cm$^{-1}$ (w), 1005 cm$^{-1}$ (m), 905 cm$^{-1}$ (m), 844 cm$^{-1}$ (m), 810 cm$^{-1}$ (m), 770 cm$^{-1}$ (m), 683 cm$^{-1}$ (m)

*"s"=strong (transmittance≤50%), "m"=medium (50%<transmittance≤70%), "w"=weak (transmittance>70%)

Figure 22:
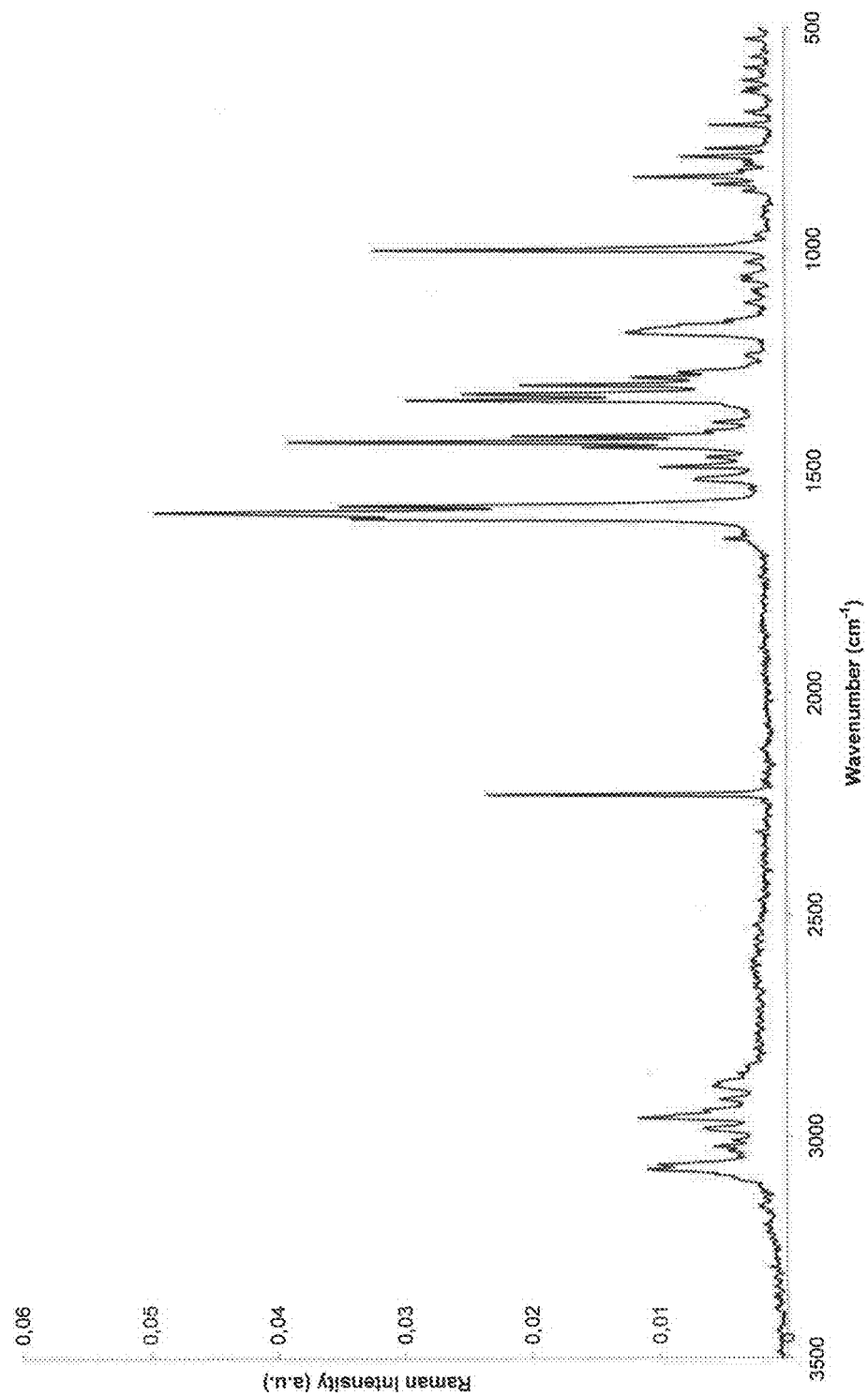
FIG. 22 depicts the FT-Raman spectrum of crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate.

An FT-Raman spectrum is depicted in FIG. 22 and the band positions are given below.

Crystalline modification H2 Raman band positions ±2 cm$^{-1}$ (relative intensity*):

3075 cm$^{-1}$ (w), 2959 cm$^{-1}$ (w), 2229 cm$^{-1}$ (m), 1592 cm$^{-1}$ (s), 1578 cm$^{-1}$ (m), 1490 cm$^{-1}$ (w), 1445 cm$^{-1}$ (w), 1434 cm$^{-1}$ (m), 1420 cm$^{-1}$ (m), 1340 cm$^{-1}$ (m), 1325 cm$^{-1}$ (m), 1306 cm$^{-1}$ (m), 1187 cm$^{-1}$ (w), 1001 cm$^{-1}$ (m), 836 cm$^{-1}$ (w)

*"s"=strong (relative Raman intensity≥0.04), "m"=medium (0.04>relative Raman intensity≥0.02), "w"=weak (relative Raman intensity<0.02)

Figure 23:
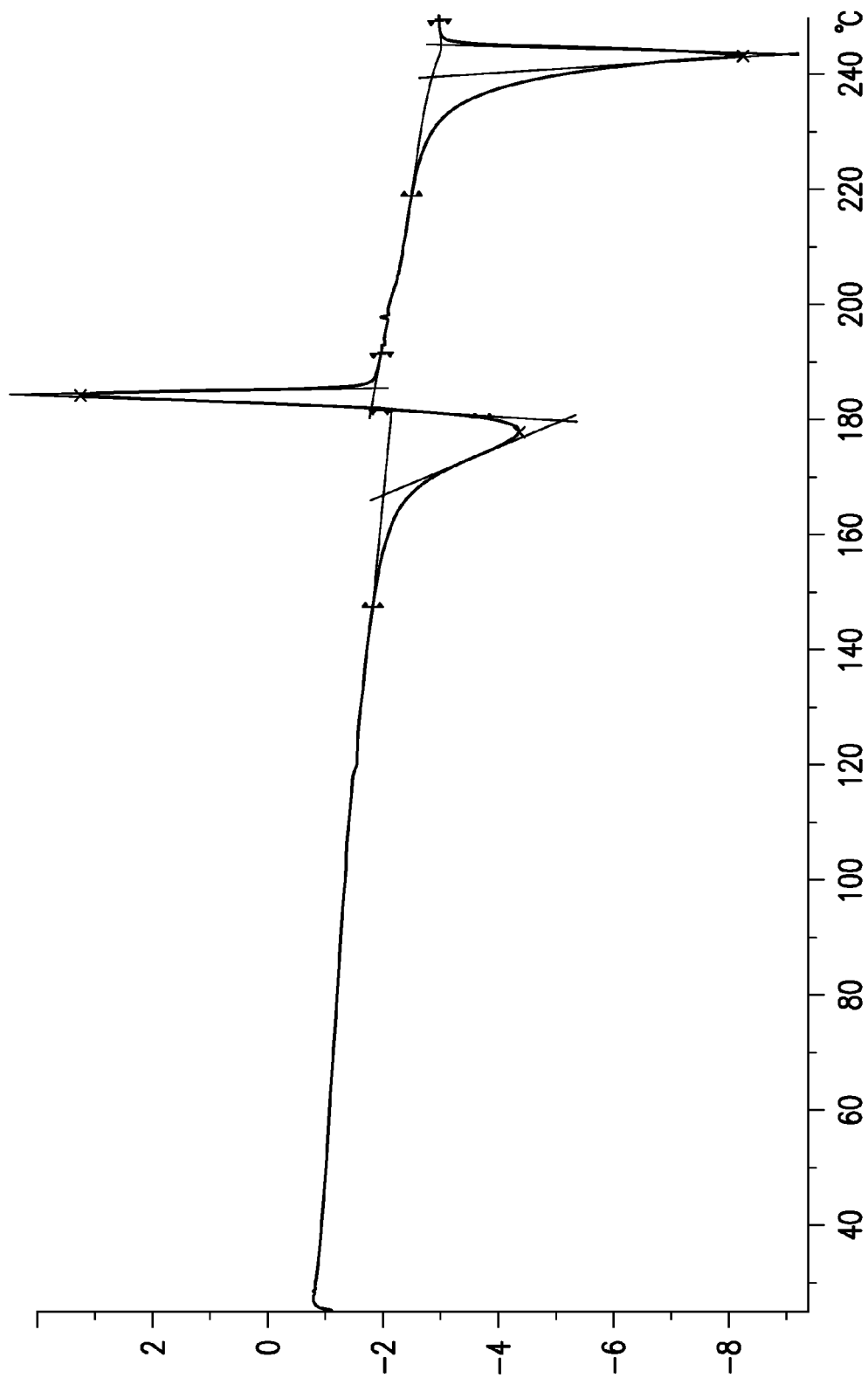
FIG. 23 depicts the DSC scan profile (Mettler-Toledo DSC 821, 5 K/min, nitrogen purge gas 50 mL/min) of crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate.
Figure 24:
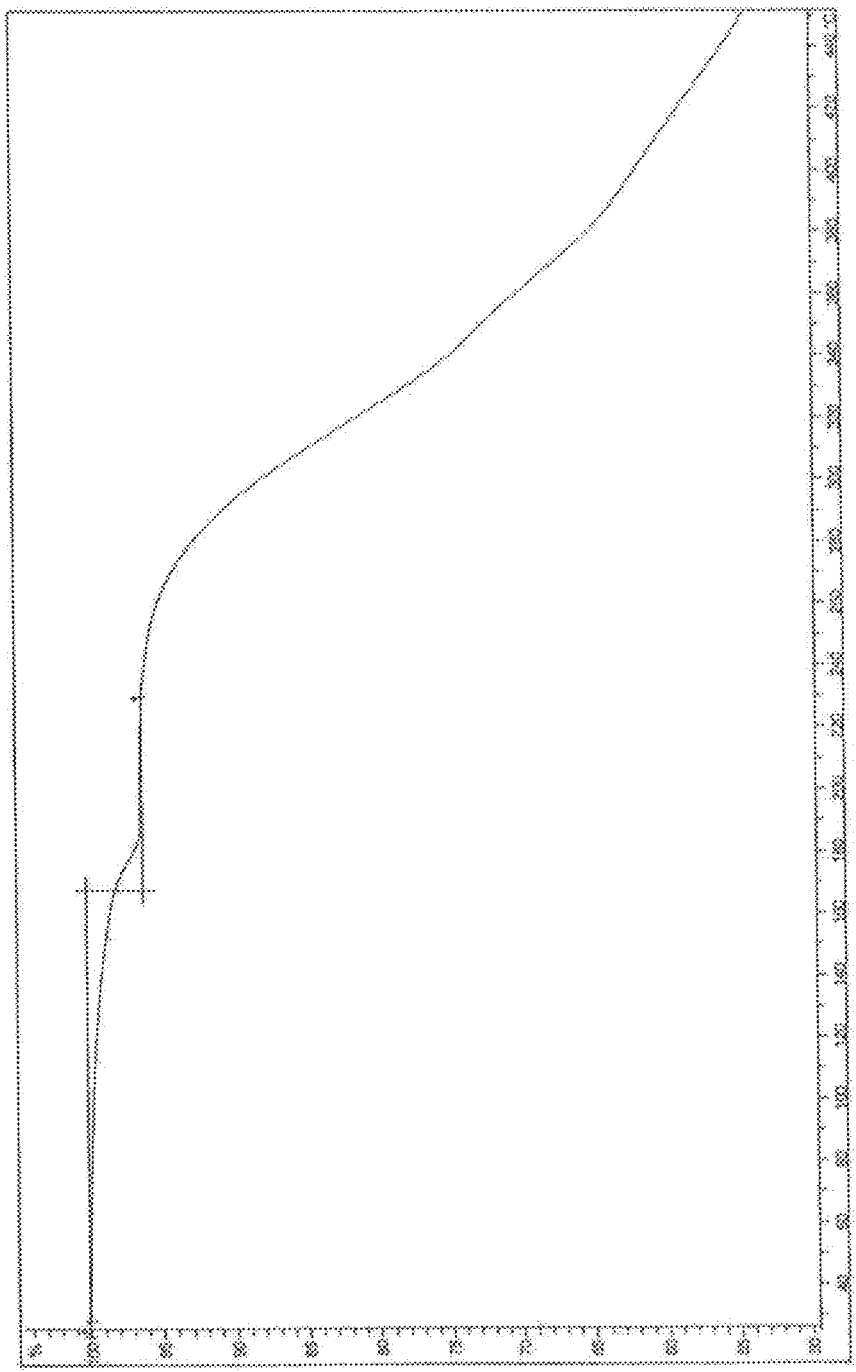
FIG. 24 depicts the TGA scan profile (Mettler-Toledo TGA 851, 5 K/min, nitrogen purge gas 50 mL/min) of crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate.

Crystalline modification H2 is a crystalline monohydrate form, which is further characterized by the following physical properties:

Thermal behaviour of crystalline modification H2 shows no loss of hydrate water ≤80° C. From approx. 80-150° C. dehydration occurs with loss of crystallinity and subsequent re-crystallisation of the anhydrous form. At approx. 230° C. melting occurs. DSC profile (Mettler-Toledo DSC 821, 5 K/min, nitrogen purge gas 50 mL/min) and TGA profile (Mettler-Toledo DSC 851, 5 K/min, nitrogen purge gas 50 mL/min) are displayed in FIGS. 23 and 24, respectively.

Figure 25:
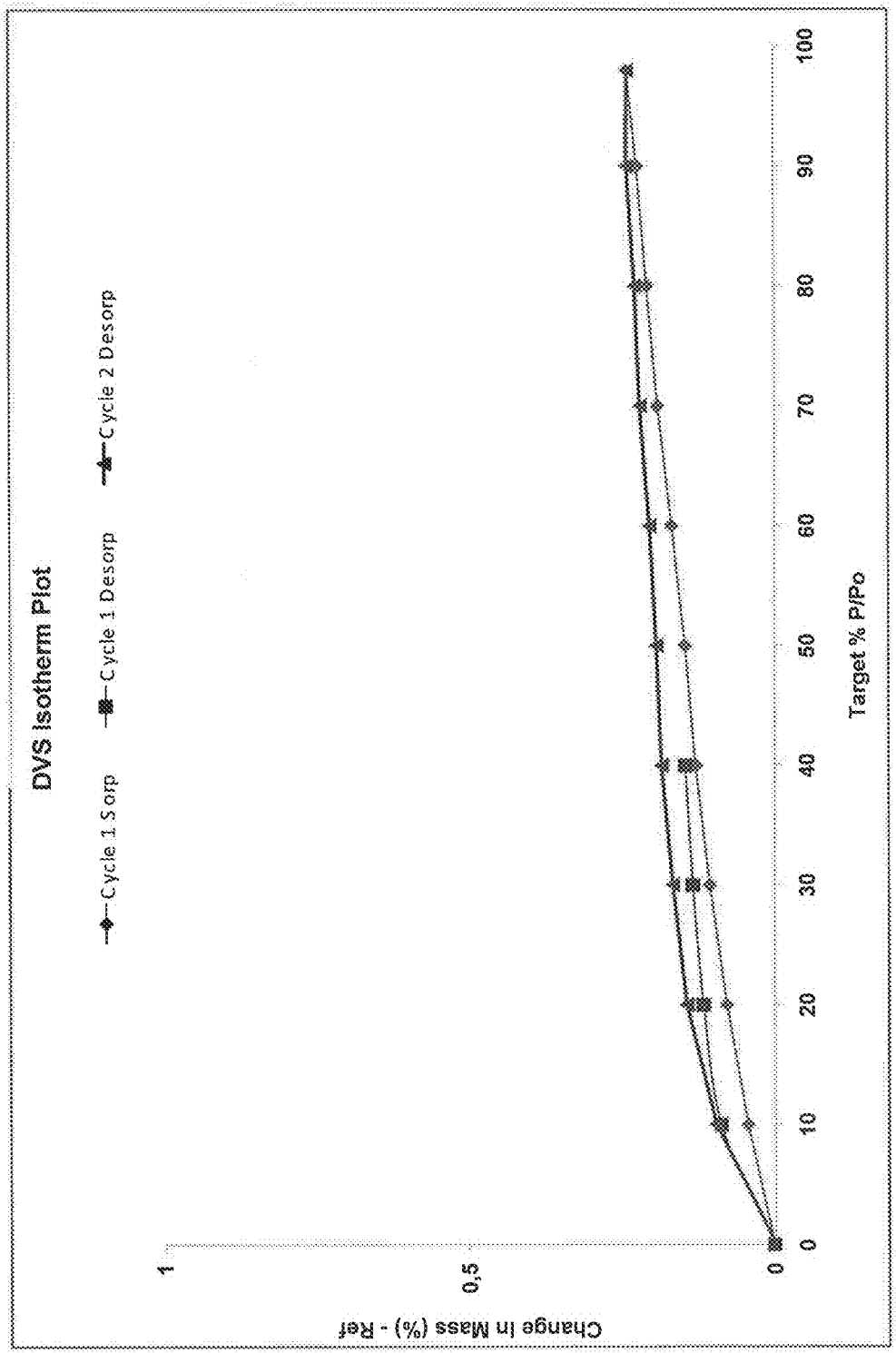
FIG. 25 depicts the Water Vapour Sorption Isotherm (25° C.) (SMS DVS Intrinsic) of crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate.

Water Vapor Sorption behavior shows small water uptake levels up to 98% relative humidity (RH), and crystalline modification H2 can be classified as non-hygroscopic acc. to Ph. Eur. criteria. At dry RH conditions, no loss of hydrate water is observed. Water Vapor Sorption isotherm (25° C.) of crystalline modification H2 is displayed in FIG. 25.

Thermodynamic solubility of crystalline modification H2 in 0.1 N HCl (pH 1.0) at 37° C. was determined to be approx. 28 μg/mL. Solubility of crystalline modification H2 in Simulated Gastric Fluid (acc. to USP) at ambient conditions (approx. 20-25° C.) was determined to be approx. 20 μg/mL.

Kinetic Solubility (after 60 minutes) of crystalline modification H2 in 0.1 N HCl (pH 1.0) at room temperature (approx. 20-25° C.) was determined to be approx. 0.3 μg/mL.

Assessment of thermodynamic stability compared to other hydrate forms H1 and NF3 by competitive binary slurry conversion experiments in a series of different solvents at 25° C. and 50° C. reveals that crystalline modification H2 is the thermodynamically stable hydrate form.

Example 12

Reproduction of Example 4 of PCT/EP2008/005508 (Manufacture of Compound "A7")

Approx. 511 mg of 3-(1-{3-[5-(1-methyl-piperidin-4-ylmethoxy)-pyrimidin-2-yl]-benzyl}-6-oxo-1,6-dihydro-pyridazin-3-yl)-benzonitrile were dispersed in 75 mL acetone, and approx. 1.12 mL of 1 N aqueous HCl solution were added (Note: in contrast to Example 4 of PCT/EP2008/005508, no clear solution was obtained. However, the remaining solid-state residue was removed by filtration to yield a clear solution afterwards). The resulting clear solution was then incubated overnight, whereupon crystals were obtained. The crystals were separated by filtration, and dried for 1 h in a vacuum drying cabinet at 65° C.

Figure 26:
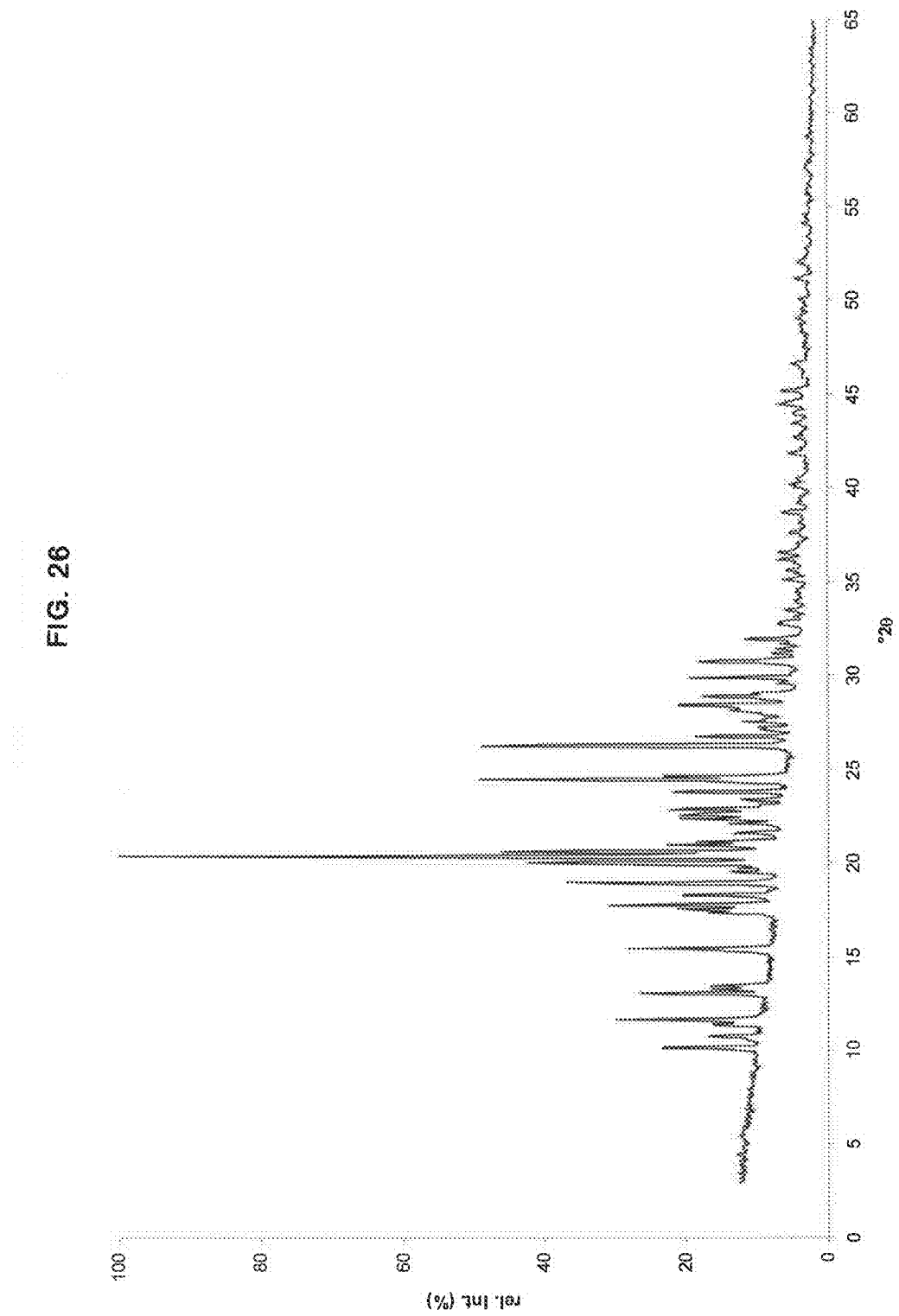
FIG. 26 depicts a powder X-ray diffractogram of compound "A7" according to Example 4 of PCT/EP2008/005508.

A Powder X-Ray Diffraction pattern of compound "A7" was obtained by standard techniques as described in the European Pharmacopeia 6$^{th}$ Edition chapter 2.9.33, and is characterized by the following X-ray powder diffractogram (Cu—Kα$_1$ radiation, λ=1.5406 Å, Stoe StadiP 611 KL diffractometer) depicted in FIG. 26.

Compound "A7" is characterized by the following XRD data:

| Powder X-ray diffractogram peak list: | | |
| --- | --- | --- |
| Peak No. | d/Å | °2θ (Cu—Kα$_1$ radiation) ± 0.1° |
| 1 | 8.74 | 10.1 |
| 2 | 8.23 | 10.7 |
| 3 | 7.62 | 11.6 |
| 4 | 6.78 | 13.0 |
| 5 | 6.58 | 13.4 |
| 6 | 5.74 | 15.4 |
| 7 | 4.99 | 17.8 |
| 8 | 4.85 | 18.3 |
| 9 | 4.68 | 18.9 |
| 10 | 4.44 | 20.0 |
| 11 | 4.36 | 20.3 |
| 12 | 3.73 | 23.8 |
| 13 | 3.64 | 24.4 |
| 14 | 3.39 | 26.3 |
| 15 | 3.14 | 28.4 |

Powder X-Ray Diffraction pattern depicted in FIG. 26 and corresponding XRD data confirm that compound "A7" is crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate.

The reproduction of Example 4 of PCT/EP2008/005508 (manufacture of compound "A7") was repeated for a second time: approx. 511 mg of 3-(1-{3-[5-(1-methyl-piperidin-4-ylmethoxy)-pyrimidin-2-yl]-benzyl}-6-oxo-1,6-dihydro-pyridazin-3-yl)-benzonitrile were dispersed in 75 mL acetone, and approx. 1.12 mL of 1 N aqueous HCl solution were added (Note: in contrast to Example 4 of PCT/EP2008/005508, no clear solution was obtained. However, the remaining solid-state residue was removed by filtration to yield a clear solution afterwards). The resulting clear solution was then agitated for 16 hours, whereupon crystals were obtained. The crystals were separated by filtration, washed with acetone, and dried in a vacuum drying cabinet.

Figure 27:
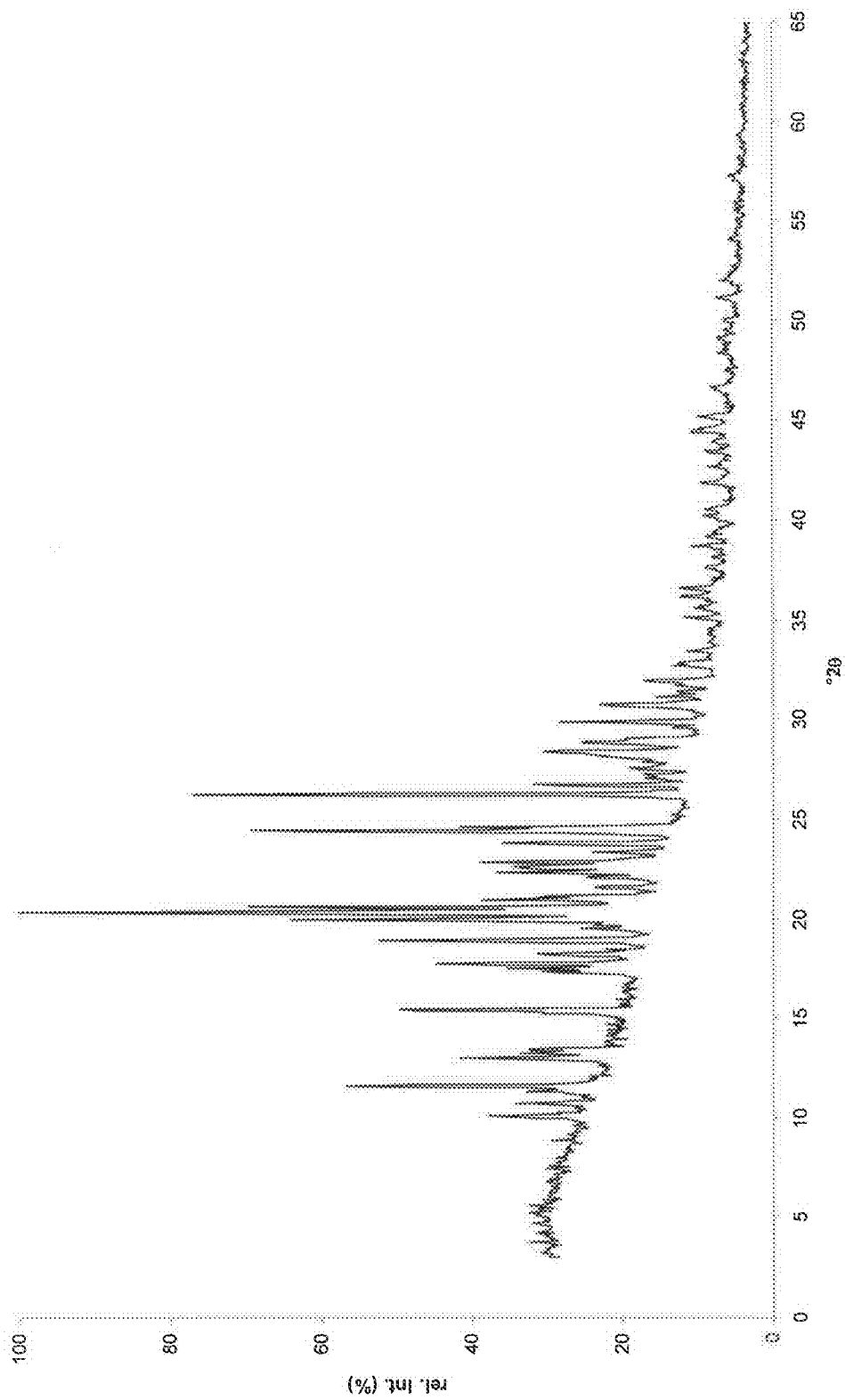
FIG. 27 depicts another powder X-ray diffractogram of compound "A7" according to Example 4 of PCT/EP2008/005508.

Another Powder X-Ray Diffraction pattern of compound "A7" was obtained by standard techniques as described in the European Pharmacopeia 6$^{th}$ Edition chapter 2.9.33, and is characterized by the following X-ray powder diffractogram (Cu—K$\alpha_1$ radiation, $\lambda$=1.5406 Å, Stoe StadiP 611 KL diffractometer) depicted in FIG. 27.

Compound "A7" is characterized by the following XRD data:

| Powder X-ray diffractogram peak list: | | |
|---|---|---|
| Peak No. | d/Å | °2θ (Cu—K$\alpha_1$ radiation) ± 0.1° |
| 1 | 8.75 | 10.1 |
| 2 | 8.23 | 10.7 |
| 3 | 7.62 | 11.6 |
| 4 | 6.80 | 13.0 |
| 5 | 6.60 | 13.4 |
| 6 | 5.75 | 15.4 |
| 7 | 4.99 | 17.7 |
| 8 | 4.86 | 18.2 |
| 9 | 4.69 | 18.9 |
| 10 | 4.44 | 20.0 |
| 11 | 4.37 | 20.3 |
| 12 | 3.74 | 23.8 |
| 13 | 3.64 | 24.4 |
| 14 | 3.39 | 26.2 |
| 15 | 3.14 | 28.4 |

Again, Powder X-Ray Diffraction pattern depicted in FIG. 27 and corresponding XRD data confirm that compound "A7" is crystalline modification H2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate.

Example 13

Structural and physico-chemical characterization of 3-(1-{3-[5-(1-methyl-pipendin-4-ylmethoxy)-pyrimidin-2-yl]-benzyl}-6-oxo-1,6-dihydro-pyridazin-3-yl)-benzonitrile hydrochloride anhydrate in its crystalline modification NF6

Figure 28:
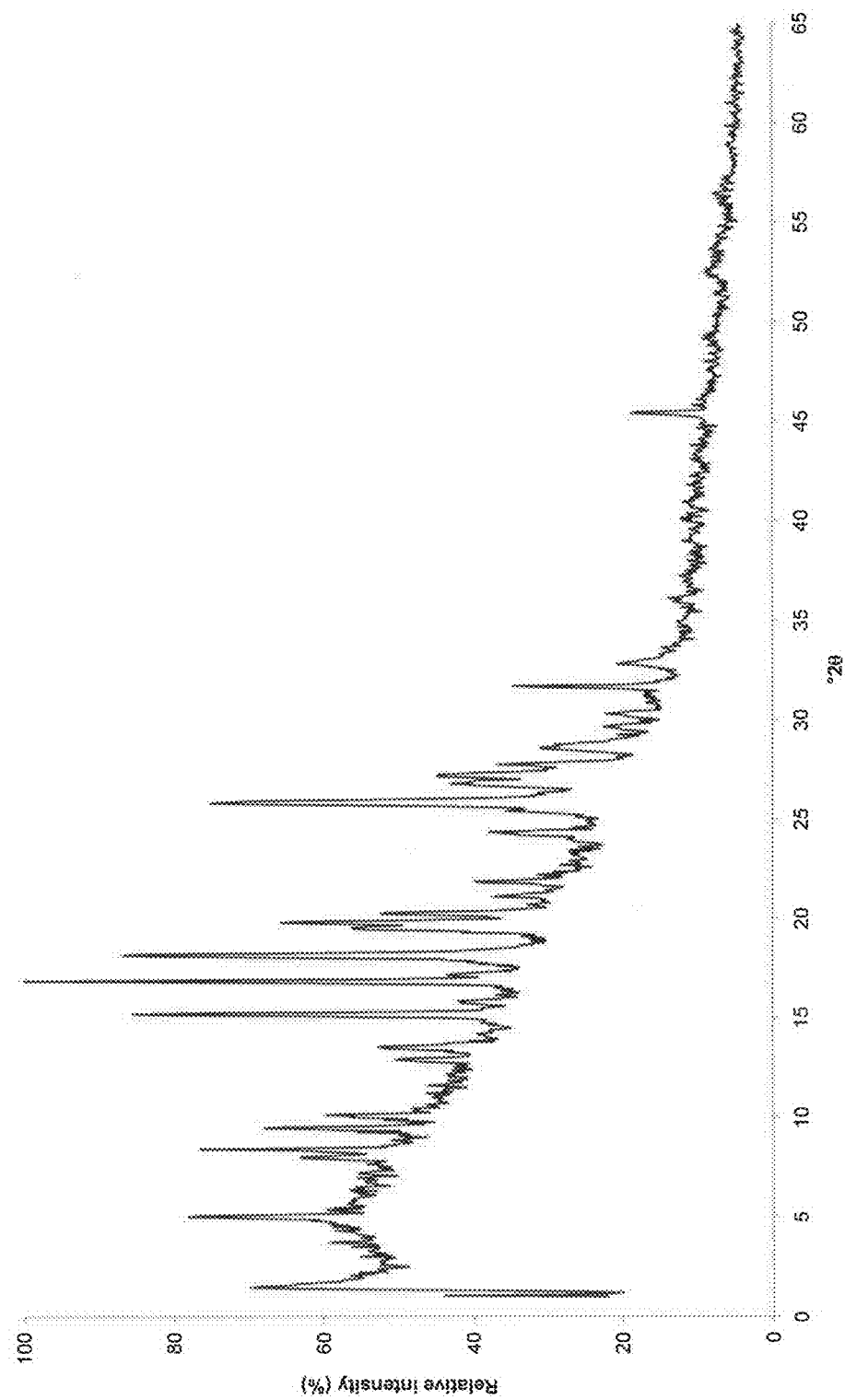
FIG. 28 depicts the powder X-ray diffractogram of crystalline modification NF6 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate.

A Powder X-Ray Diffraction pattern of crystalline modification NF6 was obtained by standard techniques as described in the European Pharmacopeia 6$^{th}$ Edition chapter 2.9.33, and is characterized by the following X-ray powder diffractogram (Cu—K$\alpha_1$ radiation, $\lambda$=1.5406 Å, Stoe StadiP 611 KL diffractometer) depicted in FIG. 28.

Crystalline modification NF6 is characterized by the following XRD data:

| Powder X-ray diffractogram peak list: | | |
|---|---|---|
| Peak No. | d/Å | °2θ (Cu—K$\alpha_1$ radiation) ± 0.1° |
| 1 | 17.66 | 5.0 |
| 2 | 11.07 | 8.0 |
| 3 | 10.53 | 8.4 |
| 4 | 9.35 | 9.4 |
| 5 | 8.77 | 10.1 |
| 6 | 6.55 | 13.5 |
| 7 | 5.83 | 15.2 |
| 8 | 5.26 | 16.8 |
| 9 | 4.88 | 18.2 |
| 10 | 4.54 | 19.5 |
| 11 | 4.48 | 19.8 |
| 12 | 4.38 | 20.3 |
| 13 | 4.06 | 21.9 |
| 14 | 3.66 | 24.3 |
| 15 | 3.50 | 25.4 |
| 16 | 3.45 | 25.8 |
| 17 | 3.32 | 26.8 |
| 18 | 3.27 | 27.2 |
| 19 | 3.21 | 27.8 |
| 20 | 3.12 | 28.6 |

Crystalline modification NF6 was further characterized by IR- and Raman-spectroscopy. FT-Raman and FT-IR spectra were obtained by standard techniques as described in the European Pharmacopeia 6$^{th}$ Edition chapter 2.02.24 and 2.02.48. For measurement of the FT-IR and FT-Raman-spectra a Bruker Vector 22 and a Bruker RFS 100 spectrometer were used. FT-IR spectra were base-line corrected using Bruker OPUS software. FT-Raman spectra were vector normalized using the same software.

Figure 29:
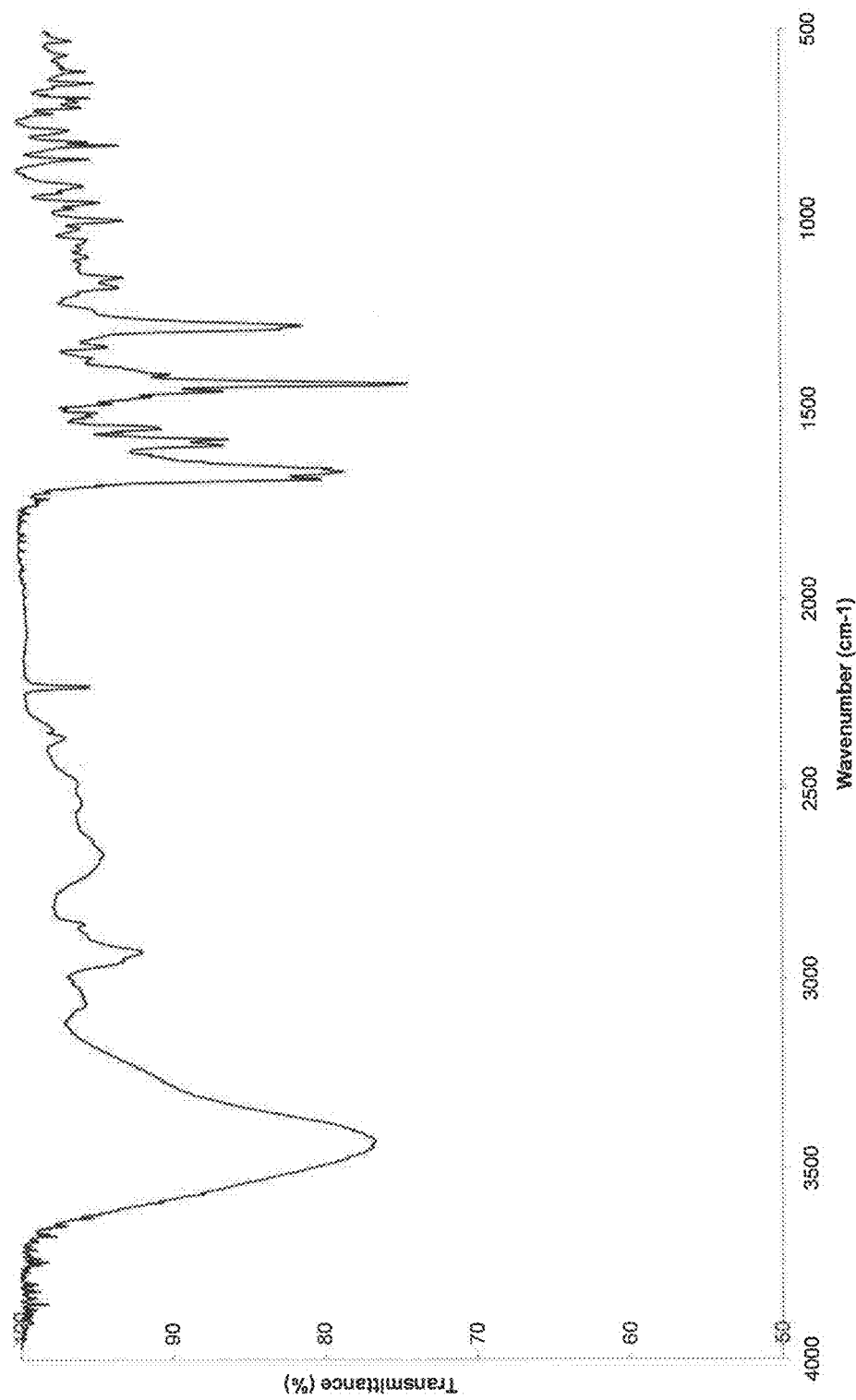
FIG. 29 depicts the FT-IR spectrum of crystalline modification NF6 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate.

An FT-IR spectrum was obtained using a KBr pellet as sample preparation technique. The FT-IR spectrum is depicted in FIG. 29 and the band positions are given below.

Crystalline modification NF6 IR band positions ±2 cm$^{-1}$ (relative intensity*)

2927 cm$^{-1}$ (w), 2671 cm$^{-1}$ (w), 2228 cm$^{-1}$ (w), 1683 cm$^{-1}$ (w), 1663 cm$^{-1}$ (w), 1593 cm$^{-1}$ (w), 1577 cm$^{-1}$ (w), 1460 cm$^{-1}$ (w), 1432 cm$^{-1}$ (w), 1278 cm$^{-1}$ (w), 1150 cm$^{-1}$ (w), 1052 cm$^{-1}$ (w), 1001 cm$^{-1}$ (w), 953 cm$^{-1}$ (w), 910 cm$^{-1}$ (w), 839 cm$^{-1}$ (w), 803 cm$^{-1}$ (w), 762 cm$^{-1}$ (w)

*"s"=strong (transmittance≤50%), "m"=medium (50%<transmittance≤70%), "w"=weak (transmittance>70%)

Figure 30:
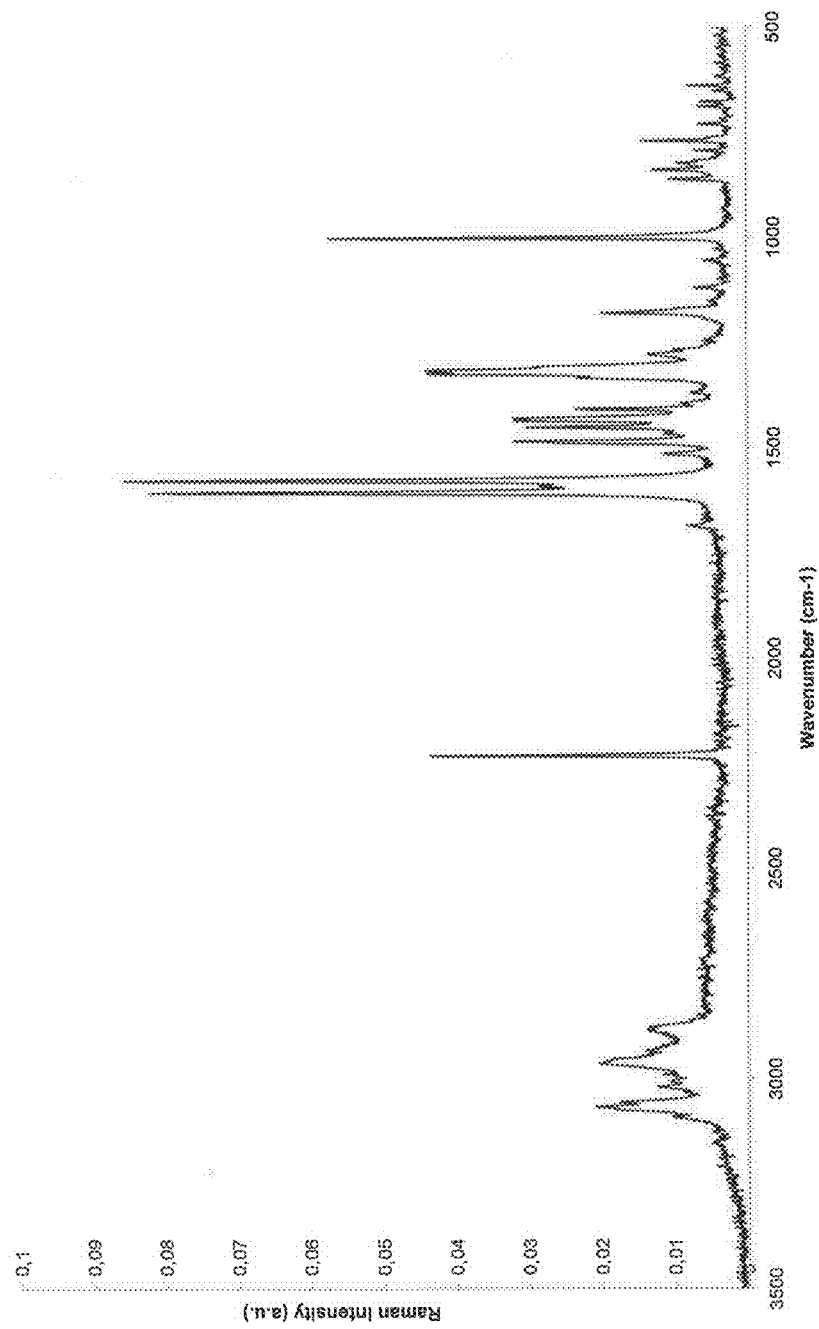
FIG. 30 depicts the FT-Raman spectrum of crystalline modification NF6 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate.

An FT-Raman spectrum is depicted in FIG. 30 and the band positions are given below.

Crystalline modification NF6 Raman band positions ±2 cm$^{-1}$ (relative intensity*):

3067 cm$^{-1}$ (m), 3056 cm$^{-1}$ (w), 2964 cm$^{-1}$ (m), 2883 cm$^{-1}$ (w), 2232 cm$^{-1}$ (s), 1606 cm$^{-1}$ (s), 1577 cm$^{-1}$ (m), 1484 cm$^{-1}$ (m), 1451 cm$^{-1}$ (m), 1436 cm$^{-1}$ (m), 1430 cm$^{-1}$ (m), 1408 cm$^{-1}$ (m), 1324 cm$^{-1}$ (s), 1316 cm$^{-1}$ (s), 1278 cm$^{-1}$ (w), 1179 cm$^{-1}$ (m), 1001 cm$^{-1}$ (s), 861 cm$^{-1}$ (w), 839 cm$^{-1}$ (w)

*"s"=strong (relative Raman intensity≥0.04), "m"=medium (0.04>relative Raman intensity≥0.02), "w"=weak (relative Raman intensity<0.02)

Figure 31:
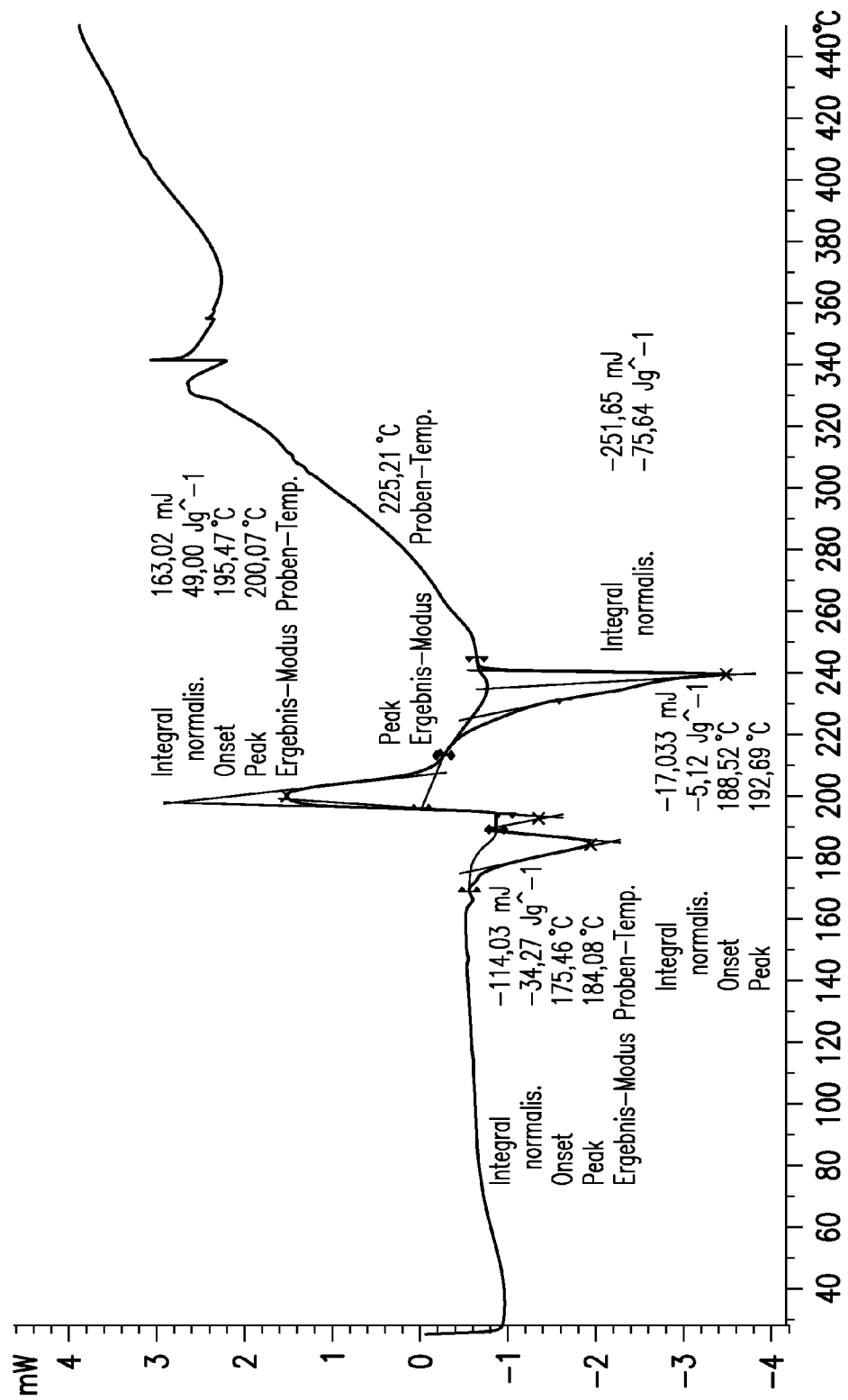
FIG. 31 depicts the DSC scan profile (Mettler-Toledo DSC821, 5 K/min, nitrogen purge gas 50 mL/min) of crystalline modification NF6 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate.
Figure 32:
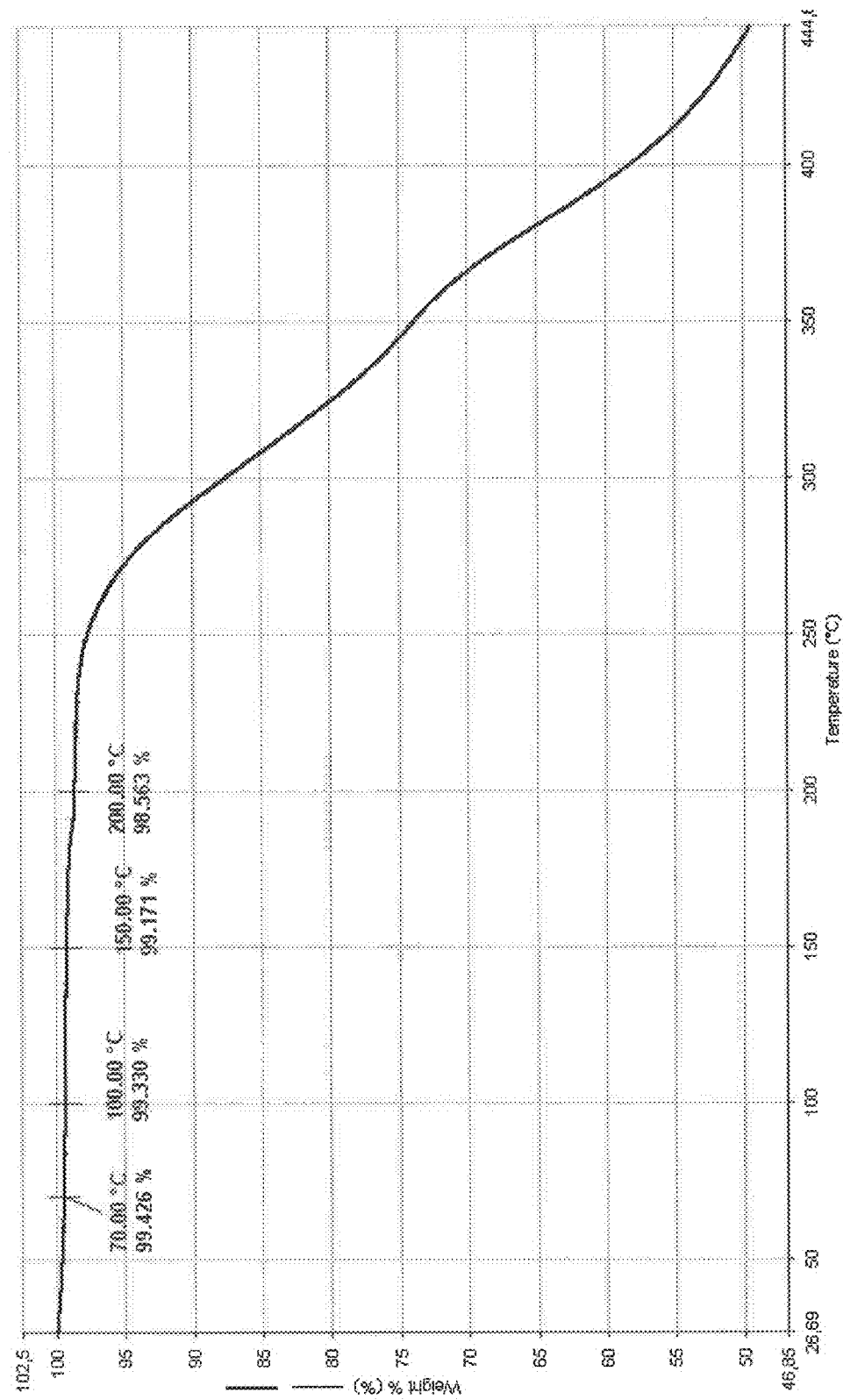
FIG. 32 depicts the TGA scan profile (Perkin-Elmer Pyris TGA1, 5 K/min, nitrogen purge gas 50 mL/min) of crystalline modification NF6 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate.

Crystalline modification NF6 is a crystalline anhydrous form, which is further characterized by the following physical properties:

Thermal behavior shows starting melting processes at approx. 175° C., with subsequent recrystallisation at approx. 195° C., and melting/decomposition of the recrystallised phase >230° C. A very small mass loss up to the melting temperature is observed. DSC profile (Mettler-Toledo DSC821, 5 K/min, nitrogen purge gas 50 mL/min) and TGA profile (Perkin-Elmer Pyris TGA1, 5 K/min, nitrogen purge gas 50 mL/min) are displayed in FIGS. 31 and 32, respectively.

Figure 33:
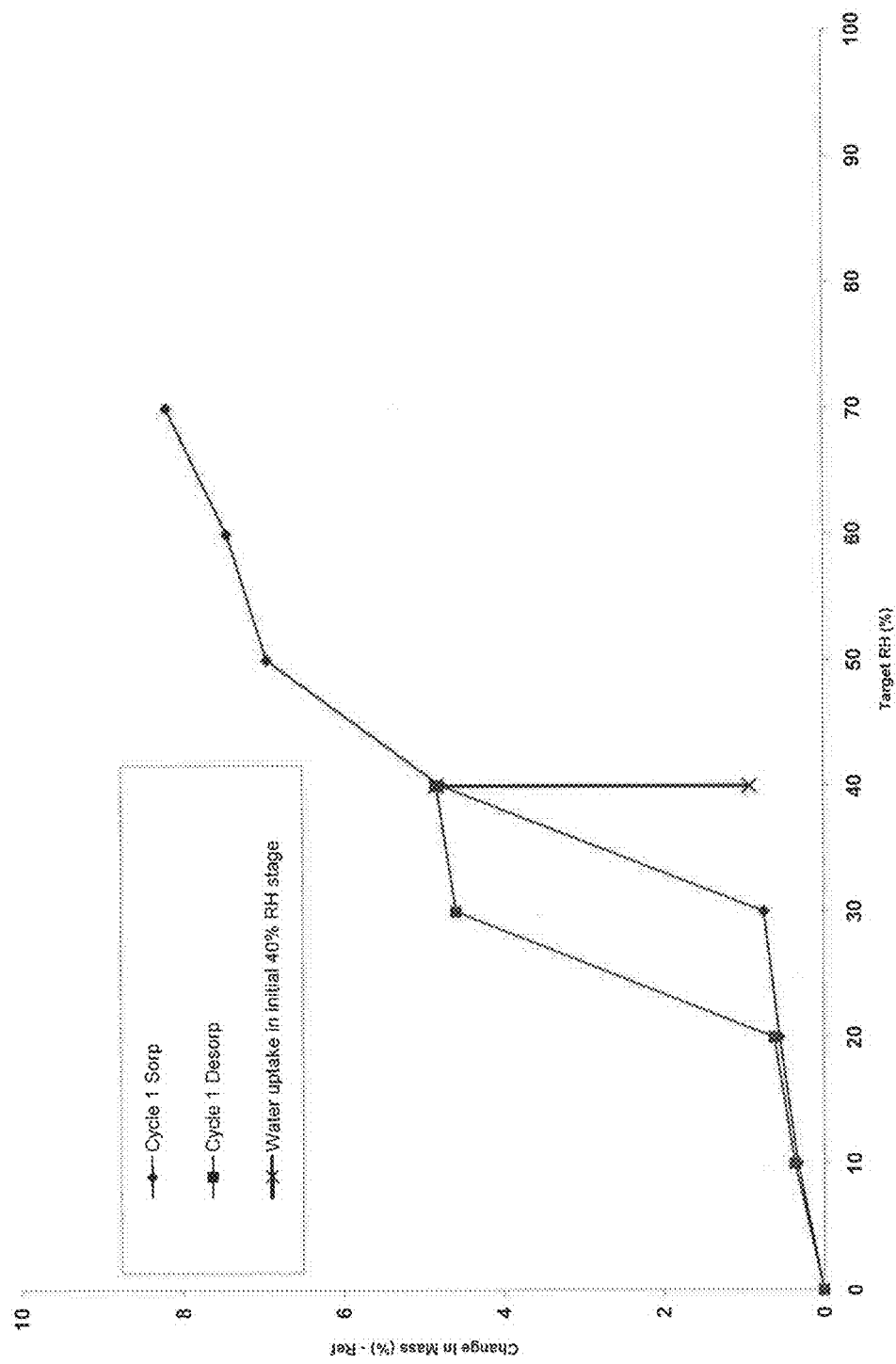
FIG. 33 depicts the Water Vapour Sorption Isotherm (25° C.) (SMS DVS Intrinsic) of crystalline modification NF6 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate.

Water Vapor Sorption behavior shows a pronounced water uptake in the initial sorption stage at 40% relative humidity (RH), with subsequent full re-desorption from 30-0%. Upon $2^{nd}$ adsorption cycle, a pronounced water uptake up to approx. 8 wt % is observed up to 70% RH. Water Vapor Sorption isotherm (25° C.) of crystalline modification NF6 is displayed in FIG. 33.

Thermodynamic Solubility of crystalline modification NF6 in 0.1N HCl (pH 1.0) at 37° C. was determined to be >200 µg/mL Example 14

Structural and physico-chemical characterization of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate in its crystalline modification NF4

Figure 34:
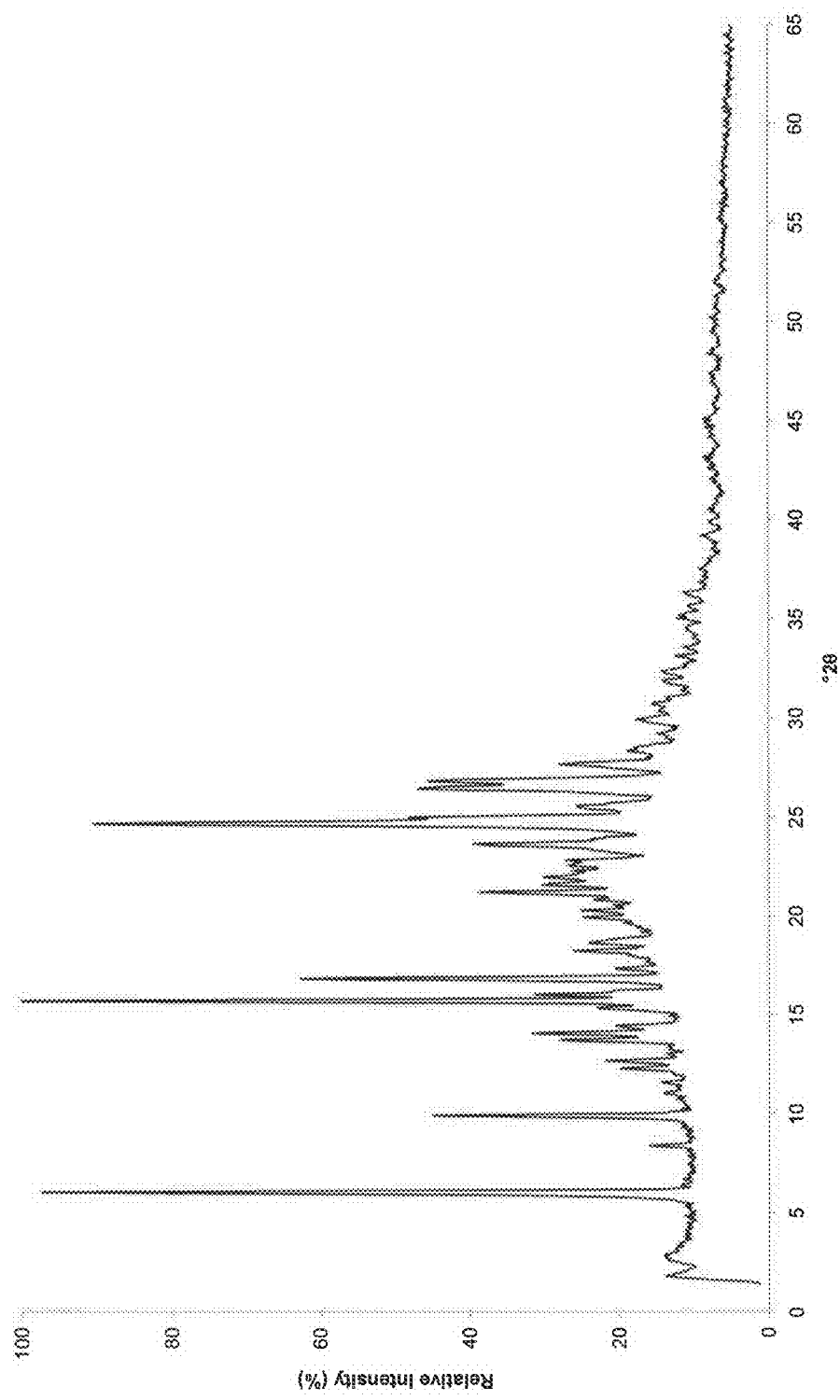
FIG. 34 depicts the powder X-ray diffractogram of crystalline modification NF4 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride anhydrate.

A Powder X-Ray Diffraction pattern of crystalline modification NF4 was obtained by standard techniques as described in the European Pharmacopeia $6^{th}$ Edition chapter 2.9.33, and is characterized by the following X-ray powder diffractogram (Cu—K$\alpha_1$ radiation, λ=1.5406 Å, Stoe StadiP 611 KL diffractometer) depicted in FIG. 34.

Crystalline modification NF4 is characterized by the following XRD data:

| Powder X-ray diffractogram peak list: | | |
|---|---|---|
| Peak No. | d/Å | °2θ (Cu—K$\alpha_1$ radiation) ± 0.1° |
| 1 | 14.61 | 6.0 |
| 2 | 8.92 | 9.9 |
| 3 | 6.45 | 13.7 |
| 4 | 6.29 | 14.1 |
| 5 | 5.63 | 15.7 |
| 6 | 5.53 | 16.0 |
| 7 | 5.28 | 16.8 |
| 8 | 4.86 | 18.2 |
| 9 | 4.19 | 21.2 |
| 10 | 4.11 | 21.6 |
| 11 | 4.04 | 22.0 |
| 12 | 3.94 | 22.6 |
| 13 | 3.89 | 22.8 |
| 14 | 3.76 | 23.6 |
| 15 | 3.60 | 24.7 |
| 16 | 3.56 | 25.0 |
| 17 | 3.49 | 25.5 |
| 18 | 3.37 | 26.5 |
| 19 | 3.32 | 26.8 |
| 20 | 3.22 | 27.7 |

Example 15

Structural and physico-chemical characterization of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate in its crystalline modification NF2

Figure 35:
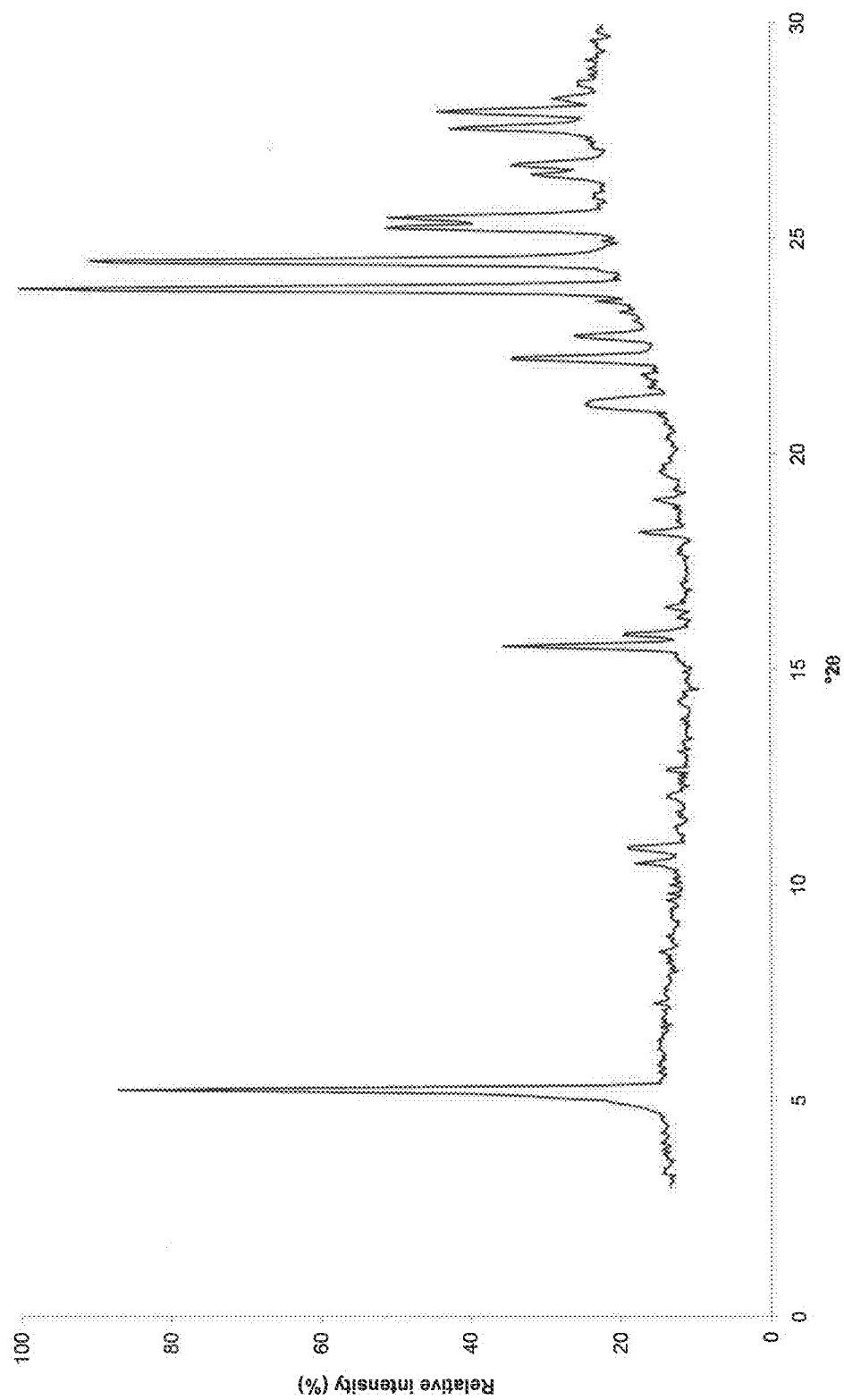
FIG. 35 depicts the powder X-ray diffractogram of crystalline modification NF2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.

A Powder X-Ray Diffraction pattern of crystalline modification NF2 was obtained by standard techniques as described in the European Pharmacopeia $6^{th}$ Edition chapter 2.9.33, and is characterized by the following X-ray powder diffractogram (Cu—K$\alpha_1$ radiation, λ=1.5406 Å, Stoe StadiP 611 KL diffractometer) depicted in FIG. 35.

Crystalline modification NF2 is characterized by the following XRD data:

| Powder X-ray diffractogram peak list: | | |
|---|---|---|
| Peak No. | d/Å | °2θ (Cu—K$\alpha_1$ radiation) ± 0.1° |
| 1 | 16.84 | 5.2 |
| 2 | 8.41 | 10.5 |
| 3 | 8.14 | 10.9 |
| 4 | 5.70 | 15.5 |
| 5 | 5.59 | 15.8 |
| 6 | 4.87 | 18.2 |
| 7 | 4.19 | 21.2 |
| 8 | 4.00 | 22.2 |
| 9 | 3.91 | 22.7 |
| 10 | 3.78 | 23.5 |
| 11 | 3.73 | 23.8 |
| 12 | 3.63 | 24.5 |
| 13 | 3.52 | 25.3 |
| 14 | 3.49 | 25.5 |
| 15 | 3.36 | 26.5 |
| 16 | 3.33 | 26.7 |
| 17 | 3.23 | 27.6 |
| 18 | 3.19 | 28.0 |
| 19 | 3.15 | 28.3 |
| 20 | 3.12 | 28.6 |

Figure 36:
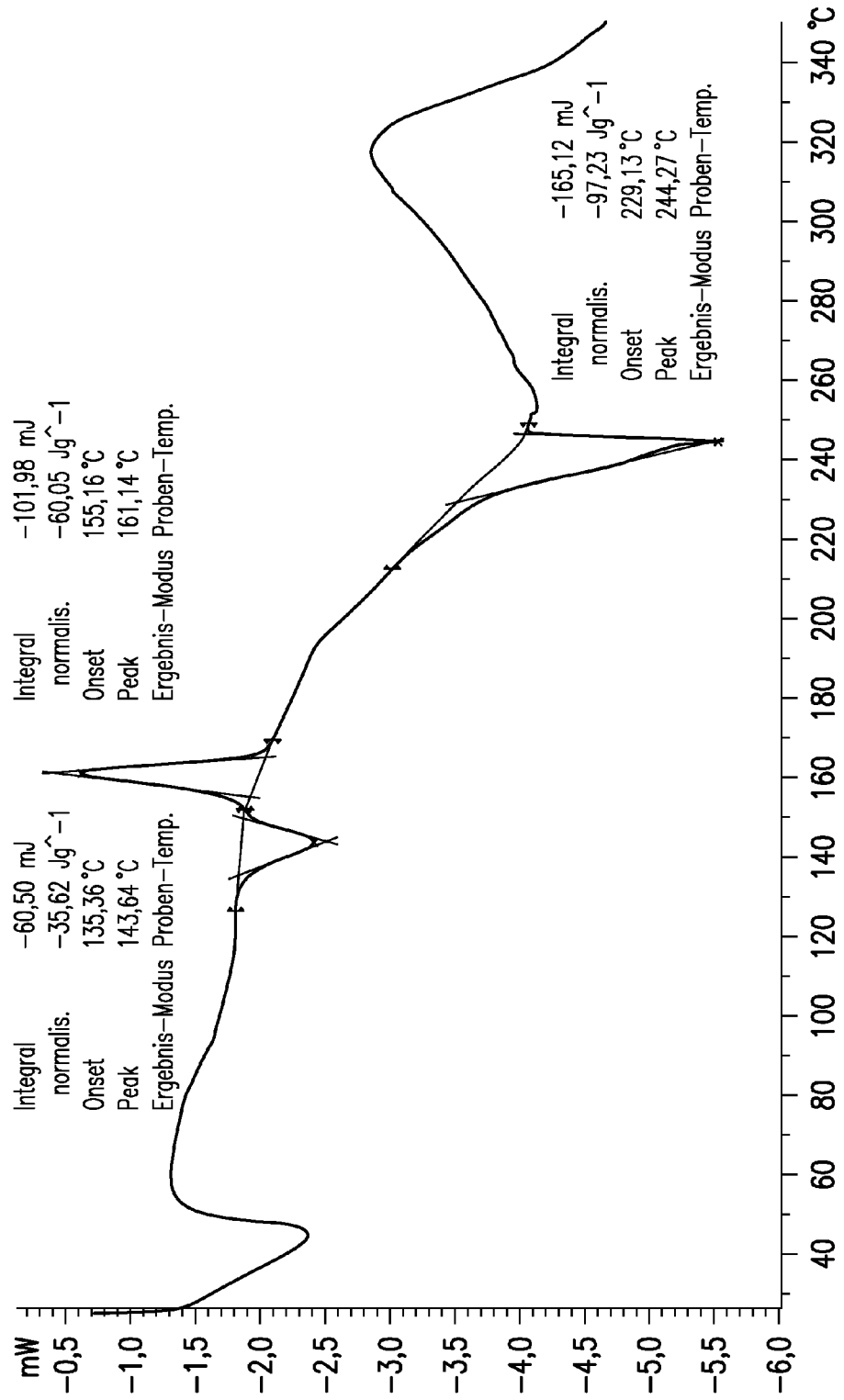
FIG. 36 depicts the DSC scan profile (Mettler-Toledo DSC821, 5 K/min, nitrogen purge gas 50 mL/min) of crystalline modification NF2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.
Figure 37:
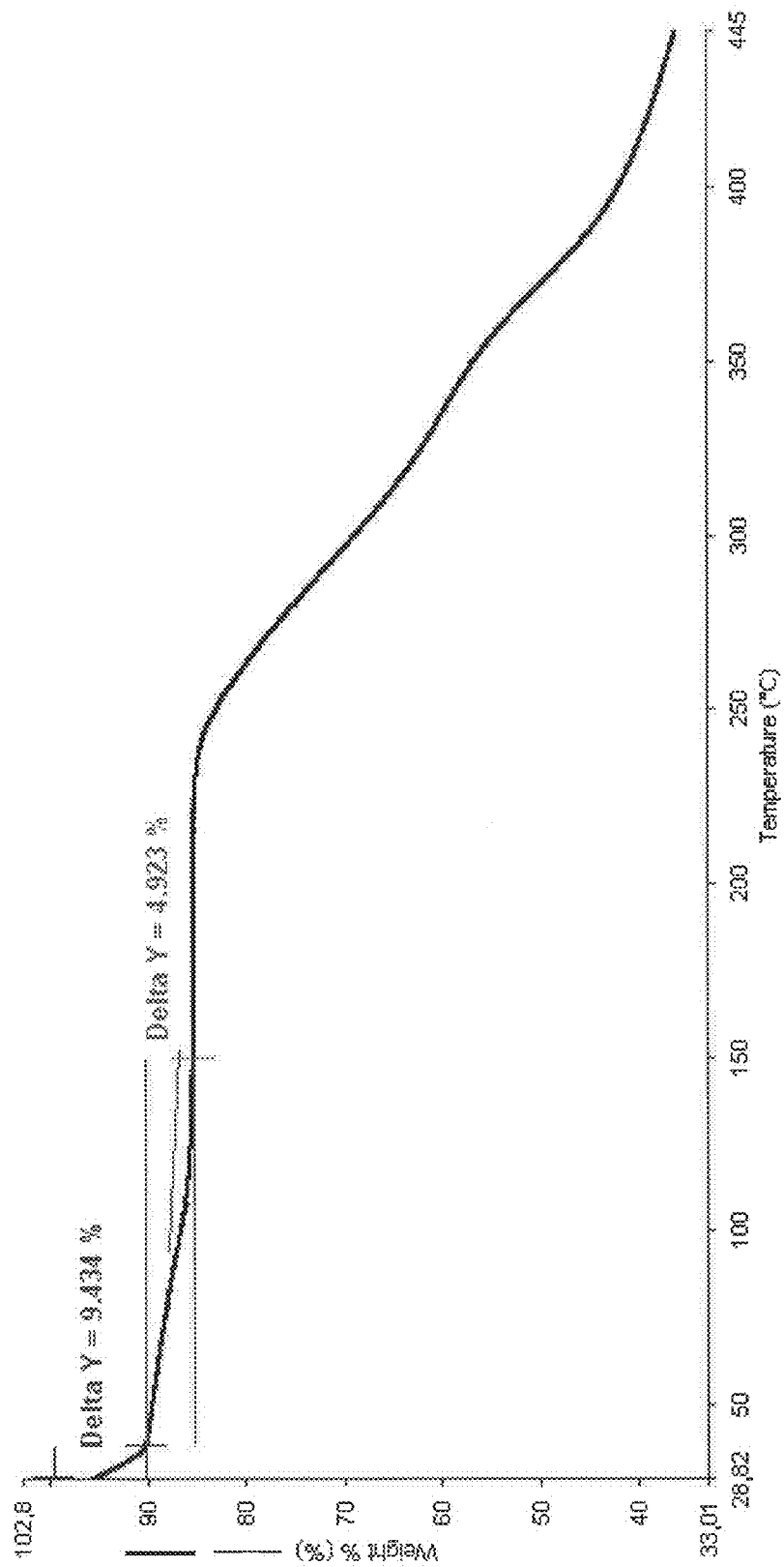
FIG. 37 depicts the TGA scan profile (Perkin-Elmer Pyris TGA1, 5 K/min, nitrogen purge gas 50 mL/min) of crystalline modification NF2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.

Crystalline modification NF2 is a crystalline hydrate form, which is further characterized by the following physical properties:

Thermal behavior shows a strong and broad endothermic event in the DSC, going along with pronounced weight loss-9-10 wt % in the TGA, at temperatures ~30-50° C. Further heating reveals melting at approx. 135° C., with immediate recrystallisation at approx. 155° C., and subsequent melting/decomposition of the recrystallised phase >230° C. Up to approx. 150° C., further weight loss is observed upon heating in the TGA scan. DSC profile (Mettler-Toledo DSC821, 5 K/min, nitrogen purge gas 50 mL/min) and TGA profile (Perkin-Elmer Pyris TGA1, 5 K/min, nitrogen purge gas 50 mL/min) are displayed in FIGS. 36 and 37, respectively.

Figure 38:
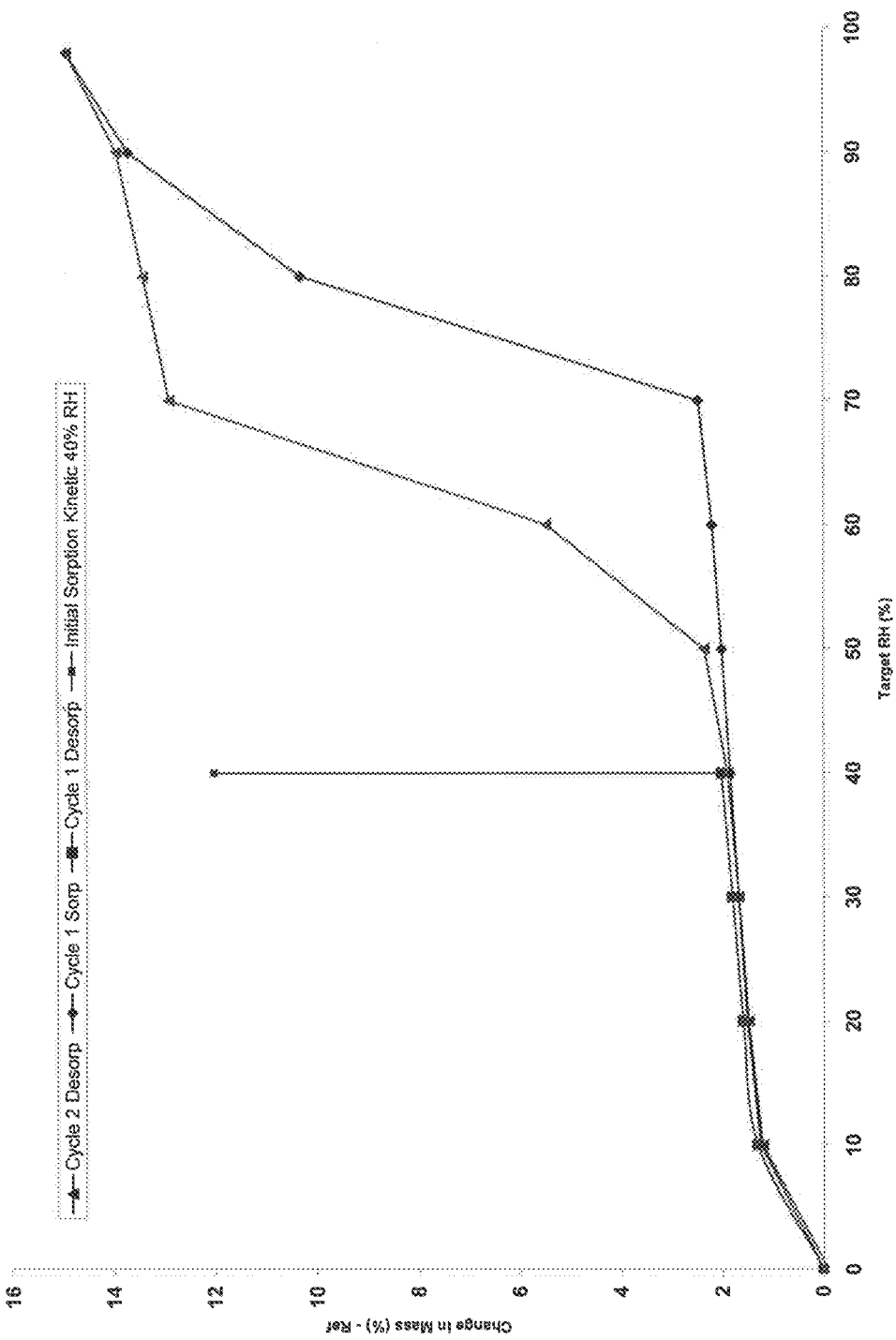
FIG. 38 depicts the Water Vapour Sorption Isotherm (25° C.) (SMS DVS Intrinsic) of crystalline modification NF2 of 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate.

Water Vapor Sorption behavior shows a pronounced weight loss in the initial 40% RH sorption stage of ~10 wt %, followed by reversible desorption/adsorption processes in the relative humidity (RH) range 40-0-70%. A strongly hygroscopic behaviour is observed at relative humidity (RH) levels >70%. Water Vapor Sorption isotherm (25° C.) of crystalline modification NF6 is displayed in FIG. 38.

The invention claimed is:

1. A method for the treatment of kidney cancer, kidney cell carcinoma, lung cancer, lung adenocarcinoma, small cell lung carcinoma, or bronchial carcinoma, which in each case is caused, mediated, or propagated by Met-kinase, said method comprising administering to a patient an effective amount of a compound selected from the following compounds:

(a) a crystalline form of a hydrochloride solvate of 3-(1-{3-[5-(1-methyl-piperidin-4-ylmethoxy)-pyrimidin-2-yl]-benzyl}-6-oxo-1,6-dihydro-pyridazin-3-yl)-benzonitrile, excluding 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate in the form of a polymorph characterized by the following XRD data:

| Peak No. | d/Å | °2θ (Cu—Kα₁ radiation) | (h, k, l) |
|---|---|---|---|
| 1 | 8.71 | 10.1 | (1, 0, 0) |
| 2 | 8.22 | 10.8 | (−1, 1, 1) |
| 3 | 7.59 | 11.6 | (1, 2, 0) |
| 4 | 6.78 | 13.0 | (0, 3, 1) |
| 5 | 6.58 | 13.5 | (−1, 3, 1) |
| 6 | 5.73 | 15.4 | (−1, 4, 1) |
| 7 | 4.98 | 17.8 | (−1, 1, 2) |
| 8 | 4.84 | 18.3 | (−2, 1, 1) |
| 9 | 4.68 | 19.0 | (−2, 2, 1) |
| 10 | 4.43 | 20.0 | (−2, 3, 1) |
| 11 | 4.35 | 20.4 | (2, 0, 0) |
| 12 | 3.73 | 23.9 | (−2, 4, 2) |
| 13 | 3.64 | 24.5 | (0, 5, 2) |
| 14 | 3.39 | 26.3 | (0, 6, 2) |
| 15 | 3.13 | 28.5 | (−3, 2, 2) | or (b) the hydrochloride anhydrate of the compound 3-(1-{3-[5-(1-methyl-piperidin-4-ylmethoxy)-pyrimidin-2-yl]-benzyl}-6-oxo-1,6-dihydro-pyridazin-3-yl)-benzonitrile.

2. A method according to claim 1, wherein said method is for the treatment of kidney cancer.

3. The method according to claim 1 wherein said compound is administered before, during, or after treatment with at least one additional pharmacologically active substance.

4. A method according to claim 1, wherein said method is for the treatment of lung adenocarcinoma, small cell lung carcinoma, or bronchial carcinomas.

5. A method according to claim 1, wherein said method is for the treatment of lung cancer.

6. The method according to claim 1, wherein said compound is a crystalline form of a hydrochloride solvate of 3-(1-{3-[5-(1-methyl-piperidin-4-ylmethoxy)-pyrimidin-2-yl]-benzyl}-6-oxo-1,6-dihydro-pyridazin-3-yl)-benzonitrile, excluding 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate in the form of a polymorph characterized by the following XRD data:

| Peak No. | d/Å | °2θ (Cu—Kα₁ radiation) + 0.1° | (h, k, l) |
|---|---|---|---|
| 1 | 8.71 | 10.1 | (1, 0, 0) |
| 2 | 8.22 | 10.8 | (−1, 1, 1) |
| 3 | 7.59 | 11.6 | (1, 2, 0) |
| 4 | 6.78 | 13.0 | (0, 3, 1) |
| 5 | 6.58 | 13.5 | (−1, 3, 1) |
| 6 | 5.73 | 15.4 | (−1, 4, 1) |
| 7 | 4.98 | 17.8 | (−1, 1, 2) |
| 8 | 4.84 | 18.3 | (−2, 1, 1) |
| 9 | 4.68 | 19.0 | (−2, 2, 1) |
| 10 | 4.43 | 20.0 | (−2, 3, 1) |
| 11 | 4.35 | 20.4 | (2, 0, 0) |
| 12 | 3.73 | 23.9 | (−2, 4, 2) |
| 13 | 3.64 | 24.5 | (0, 5, 2) |
| 14 | 3.39 | 26.3 | (0, 6, 2) |
| 15 | 3.13 | 28.5 | (−3, 2, 2). |

7. The method according to claim 1, wherein said compound is the hydrochloride anhydrate of the compound 3-(1-{3-[5-(1-methyl-piperidin-4-ylmethoxy)-pyrimidin-2-yl]-benzyl}-6-oxo-1,6-dihydro-pyridazin-3-yl)-benzonitrile.

8. The method according to claim 7, wherein said compound is in the form of a polymorph characterized by XRD peaks comprising 4.4°, 15.9° and 22.7° (in °2θ using Cu-Kα₁ radiation, ±0.1°).

9. The method according to claim 7, wherein said compound is characterized by the following XRD data:

| Peak No. | d/Å | °2θ (Cu—Kα₁ radiation) ± 0.1° |
|---|---|---|
| 1 | 20.08 | 4.4 |
| 2 | 8.55 | 10.3 |
| 3 | 7.43 | 11.9 |
| 4 | 5.70 | 15.5 |
| 5 | 5.56 | 15.9 |
| 6 | 4.99 | 17.8 |
| 7 | 4.86 | 18.2 |
| 8 | 4.74 | 18.7 |
| 9 | 4.55 | 19.5 |
| 10 | 4.46 | 19.9 |
| 11 | 4.27 | 20.8 |
| 12 | 4.10 | 21.6 |
| 13 | 3.91 | 22.7 |
| 14 | 3.82 | 23.3 |
| 15 | 3.65 | 24.3. |

10. The method according to claim 6, wherein said compound is 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride hydrate, excluding 3-(1-{3-[5-(1-methyl-piperidin-4-ylmethoxy)-pyrimidin-2-yl]-benzyl}-6-oxo-1,6-dihydro-pyridazin-3-yl)-benzonitrile hydrochloride monohydrate crystalline in the form of said polymorph.

11. The method according to claim 10, wherein said compound is in the form of a polymorph characterized by XRD peaks comprising 5.9°, 16.0° and 23.4° (in °2θ using Cu-Kα₁ radiation, ±0.1°).

12. The method according to claim 10, wherein said compound is in the form of a polymorph characterized by the following XRD data:

| Peak No. | d/Å | °2θ (Cu—Kα₁ radiation) ± 0.1° |
|---|---|---|
| 1 | 14.88 | 5.9 |
| 2 | 9.99 | 8.8 |
| 3 | 7.83 | 11.3 |
| 4 | 7.25 | 12.2 |
| 5 | 6.10 | 14.5 |
| 6 | 5.84 | 15.2 |
| 7 | 5.52 | 16.0 |
| 8 | 5.38 | 16.5 |
| 9 | 4.92 | 18.0 |
| 10 | 4.12 | 21.6 |
| 11 | 3.80 | 23.4 |
| 12 | 3.57 | 24.9 |
| 13 | 3.49 | 25.5 |
| 14 | 3.30 | 27.0 |
| 15 | 2.95 | 30.3. |

13. The method according to claim 10, wherein said compound is in the form of a polymorph characterized by XRD peaks comprising 9.9°, 15.7° and 24.1° (in °2θ using Cu-Kα₁ radiation, ±0.1°).

14. The method according to claim 10, wherein said compound is in the form of a polymorph characterized by the following XRD data:

| Peak No. | d/Å | °2θ (Cu—Kα₁ radiation) ± 0.1° |
|---|---|---|
| 1 | 14.83 | 6.0 |
| 2 | 8.96 | 9.9 |
| 3 | 6.92 | 12.8 |

| Peak No. | d/Å | °2θ (Cu—Kα₁ radiation) ± 0.1° |
|---|---|---|
| 4 | 5.62 | 15.7 |
| 5 | 5.44 | 16.3 |
| 6 | 5.26 | 16.9 |
| 7 | 4.38 | 20.3 |
| 8 | 4.32 | 20.6 |
| 9 | 3.79 | 23.5 |
| 10 | 3.69 | 24.1 |
| 11 | 3.59 | 24.8 |
| 12 | 3.55 | 25.1 |
| 13 | 3.45 | 25.8 |
| 14 | 3.35 | 26.6 |
| 15 | 3.22 | 27.7. |

15. The method according to claim 7, wherein said compound is in the form of a polymorph characterized by XRD peaks comprising 16.8°, 18.2° and 25.8° (in °2θ using Cu-Kα₁ radiation, ±0.1°).

16. The compound according to claim 7, wherein said compound is in the form of a polymorph characterized by the following XRD data:

| Peak No. | d/Å | °2θ (Cu—Kα₁ radiation) ± 0.1° |
|---|---|---|
| 1 | 17.66 | 5.0 |
| 2 | 11.07 | 8.0 |
| 3 | 10.53 | 8.4 |
| 4 | 9.35 | 9.4 |
| 5 | 8.77 | 10.1 |
| 6 | 6.55 | 13.5 |
| 7 | 5.83 | 15.2 |
| 8 | 5.26 | 16.8 |
| 9 | 4.88 | 18.2 |
| 10 | 4.54 | 19.5 |
| 11 | 4.48 | 19.8 |
| 12 | 4.38 | 20.3 |
| 13 | 4.06 | 21.9 |
| 14 | 3.66 | 24.3 |
| 15 | 3.50 | 25.4 |
| 16 | 3.45 | 25.8 |
| 17 | 3.32 | 26.8 |
| 18 | 3.27 | 27.2 |
| 19 | 3.21 | 27.8 |
| 20 | 3.12 | 28.6. |

17. The method according to claim 7, wherein said compound is in the form of a polymorph characterized by XRD peaks comprising 6.0°, 15.7° and 24.7° (in °2θ using Cu-Kα₁ radiation, ±0.1°).

18. The method according to claim 7, wherein said compound is in the form of a polymorph characterized by the following XRD data:

| Peak No. | d/Å | °2θ (Cu—Kα₁ radiation) ± 0.1° |
|---|---|---|
| 1 | 14.61 | 6.0 |
| 2 | 8.92 | 9.9 |
| 3 | 6.45 | 13.7 |
| 4 | 6.29 | 14.1 |
| 5 | 5.63 | 15.7 |
| 6 | 5.53 | 16.0 |
| 7 | 5.26 | 16.8 |
| 8 | 4.86 | 18.2 |
| 9 | 4.19 | 21.2 |
| 10 | 4.11 | 21.6 |
| 11 | 4.04 | 22.0 |
| 12 | 3.94 | 22.6 |
| 13 | 3.89 | 22.8 |
| 14 | 3.76 | 23.6 |
| 15 | 3.60 | 24.7 |
| 16 | 3.56 | 25.0 |
| 17 | 3.49 | 25.5 |
| 18 | 3.37 | 26.5 |
| 19 | 3.32 | 26.8 |
| 20 | 3.22 | 27.7. |

19. The method according to claim 10, wherein said compound is in the form of a polymorph characterized by XRD peaks comprising 5.2°, 23.8° and 24.5° (in °2θ using Cu-Kα₁ radiation, ±0.1°).

20. The method according to claim 10, wherein said compound is in the form of a polymorph characterized by the following XRD data:

| Peak No. | d/Å | °2θ (Cu—Kα₁ radiation) ± 0.1° |
|---|---|---|
| 1 | 16.84 | 5.2 |
| 2 | 8.41 | 10.5 |
| 3 | 8.14 | 10.9 |
| 4 | 5.70 | 15.5 |
| 5 | 5.59 | 15.8 |
| 6 | 4.87 | 18.2 |
| 7 | 4.19 | 21.2 |
| 8 | 4.00 | 22.2 |
| 9 | 3.91 | 22.7 |
| 10 | 3.78 | 23.5 |
| 11 | 3.73 | 23.8 |
| 12 | 3.63 | 24.5 |
| 13 | 3.52 | 25.3 |
| 14 | 3.49 | 25.5 |
| 15 | 3.36 | 26.5 |
| 16 | 3.33 | 26.7 |
| 17 | 3.23 | 27.6 |
| 18 | 3.19 | 28.0 |
| 19 | 3.15 | 28.3 |
| 20 | 3.12 | 28.6. |

21. The method according to claim 6, wherein said compound is a solvate of water, methanol, ethanol, propan-1-ol, propan-2-ol, ethyl acetate, acetonitrile, acetone, butanone, tetrahydrofuran, chloroform, n-heptane, or toluene.

22. The method according to claim 21, wherein said compound is a solvate of water, acetone, tetrahydrofuran, methanol, ethyl acetate, or n-heptane.

* * * * *